(12) United States Patent
Conn et al.

(10) Patent No.: US 8,697,691 B2
(45) Date of Patent: Apr. 15, 2014

(54) ALKYL 3-((2-AMIDOETHYL)AMINO)-8-AZABICYCLO[3.2.1]OCTANE-8-CARBOXYLATE ANALOGS AS SELECTIVE M1 AGONISTS AND METHODS OF MAKING AND USING SAME

(75) Inventors: P. Jeffrey Conn, Brentwood, TN (US); Craig W. Lindsley, Brentwood, TN (US); Michael R. Wood, Brentwood, TN (US); Rocco D. Gogliotti, Kingston Springs, TN (US); Colleen M. Niswender, Brentwood, TN (US); Bruce J. Melancon, Nashville, TN (US); Evan P. Lebois, Atlanta, GA (US)

(73) Assignee: Vanderbilt University, Nashville, TN (US)

( * ) Notice: Subject to any disclaimer, the term of this patent is extended or adjusted under 35 U.S.C. 154(b) by 423 days.

(21) Appl. No.: 12/975,331

(22) Filed: Dec. 21, 2010

(65) Prior Publication Data

US 2011/0172227 A1 Jul. 14, 2011

Related U.S. Application Data

(60) Provisional application No. 61/288,717, filed on Dec. 21, 2009.

(51) Int. Cl.
| | | |
|---|---|---|
| C07D 471/08 | (2006.01) | |
| A61K 31/439 | (2006.01) | |
| A61K 31/4545 | (2006.01) | |
| A61K 31/444 | (2006.01) | |
| A61K 31/5377 | (2006.01) | |

(52) U.S. Cl.
USPC ........ 514/233.2; 546/125; 546/132; 544/127; 514/304

(58) Field of Classification Search
USPC ............... 514/233.2, 304; 546/125, 132, 126; 544/127
See application file for complete search history.

(56) References Cited

U.S. PATENT DOCUMENTS

| | | | | |
|---|---|---|---|---|
| 5,242,927 | A | 9/1993 | Baker | 514/299 |
| 6,828,333 | B2 | 12/2004 | Marfat | 514/338 |
| 7,060,717 | B2 | 6/2006 | Balley | 514/350 |
| 7,807,704 | B2 | 10/2010 | Thomas | 514/412 |
| 2006/0100168 | A1 | 5/2006 | Ravid | 514/46 |
| 2007/0197530 | A1 | 8/2007 | Li | 546/192 |
| 2008/0261999 | A1 | 10/2008 | Martin | 514/256 |
| 2009/0304692 | A1 | 12/2009 | Venkatesan | 544/106 |

FOREIGN PATENT DOCUMENTS

| | | |
|---|---|---|
| WO | WO-2005/117883 A1 | 12/2005 |
| WO | PCT/EP2006/060406 | 3/2006 |
| WO | 2006133802 | * 12/2006 |
| WO | WO-2009/106534 A1 | 9/2009 |
| WO | PCT/US2010/061674 | 12/2010 |

OTHER PUBLICATIONS

International Search Report issued Mar. 15, 2011 by the International Searching Authority for Application PCT/US2010/061674 filed Dec. 21, 2010 and later published as WO 2011/087812 on Jul. 21, 2011 (Applicant—Vanderbilt University // Inventor—Craig W. Lindsley, et al.) (2 pages).

Written Opinion of the International Search Report issued Oct. 31, 2011 by the International Searching Authority for Application PCT/US2010/061674 filed Dec. 21, 2010 and later published as WO 2011/087812 on Jul. 21, 2011 (Applicant—Vanderbilt University // Inventor—Craig W. Lindsley, et al.) (4 pages).

International Preliminary Report on Patentability issued Sep. 21, 2012 by the International Searching Authority for Application PCT/US2010/061674 filed Dec. 21, 2010 and later published as WO 2011/087812 on Jul. 21, 2011 (Applicant—Vanderbilt University // Inventor—Craig W. Lindsley, et al.) (5 pages).

Blackburn, et al., Identification and characterization of amino-piperidinequinolones and quinazolinones as MCHr1 antagonists. *Bioorg Med Chem Lett* 2006, 16(10): 2621-2627.

Conn, et al., Subtype-selective allosteric modulators of muscarinic receptors for the treatment of CNS disorders. *Trends Pharmacol Sci* 2009, 30(3): 148-155.

May, et al., Allosteric modulation of G protein-coupled receptors. *Annu Rev Pharmacol Toxicol* 2007, 47: 1-51.

Lebois, et al. Discovery and Characterization of Novel Subtype-Selective Allosteric Agonists for the Investigation of M1 Receptor Function in the Central Nervous System. ACS Chem. Neurosci. ePub Sep. 25, 2009, 1(2): 104-121.

(Continued)

*Primary Examiner* — Niloofar Rahmani
(74) *Attorney, Agent, or Firm* — Ballard Spahr LLP

(57) ABSTRACT

In one aspect, the invention relates to compounds having a general structure:

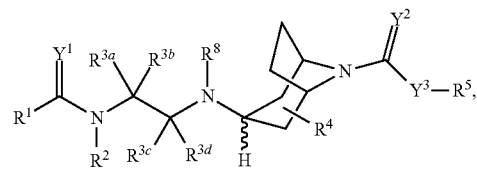

which are useful as selective allosteric or bitopic agonists of the $M_1$ muscarinic receptor; synthetic methods for making the compounds; pharmaceutical compositions comprising the compounds; and methods of using the compounds, for example, in treating neurodegenerative diseases, including Alzheimer's Disease. This abstract is intended as a scanning tool for purposes of searching in the particular art and is not intended to be limiting of the present invention.

13 Claims, 12 Drawing Sheets

(56) References Cited

OTHER PUBLICATIONS

Peng, et al. Structure and Function Prediction of Human Muscarinic acetylcholine Receptor 1, Cation-Pi Studies, and Protein Design. 2005. PhD thesis. California Institue of Technology, Pasadena, California. [Retrieved from the Internet Apr. 20, 2011; <http://thesis.library.caltech.edu/2327/1/FinalThesisJoyce.pdf>].

Verma, et al. 3D-QSAR study of 8-azabicyclos[3.2.1] octane analogs antagonists of cholinergic receptor. Bioorg Med Chem Lett. 2009, 19(11): 3108-3112.

International Search Report issued on Oct. 31, 2011 by the International Search Authority for PCT/US2011/27924 filed on Mar. 10, 2011 and published as WO 2011/112825 on Sep. 15, 2011.

* cited by examiner

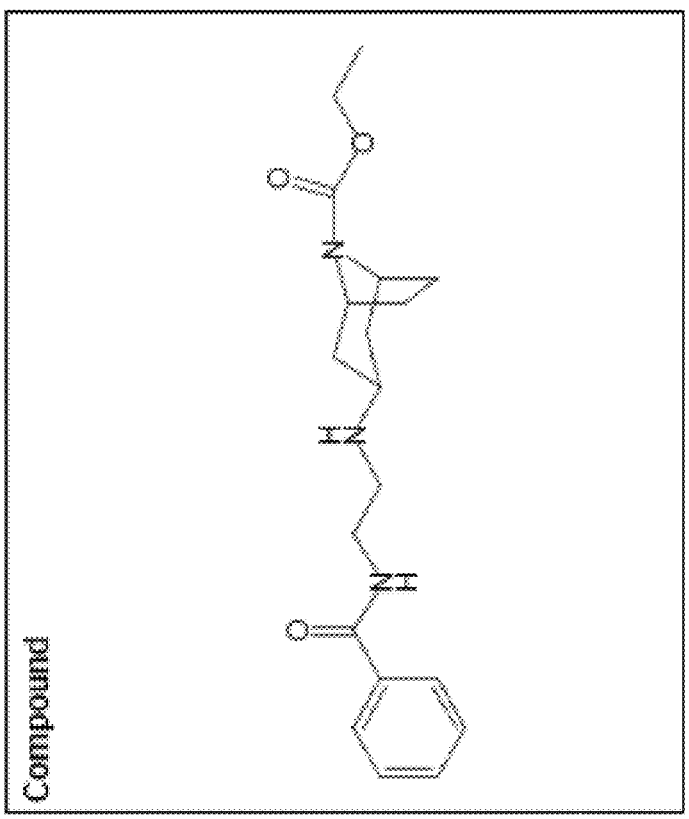
Figure 1.0

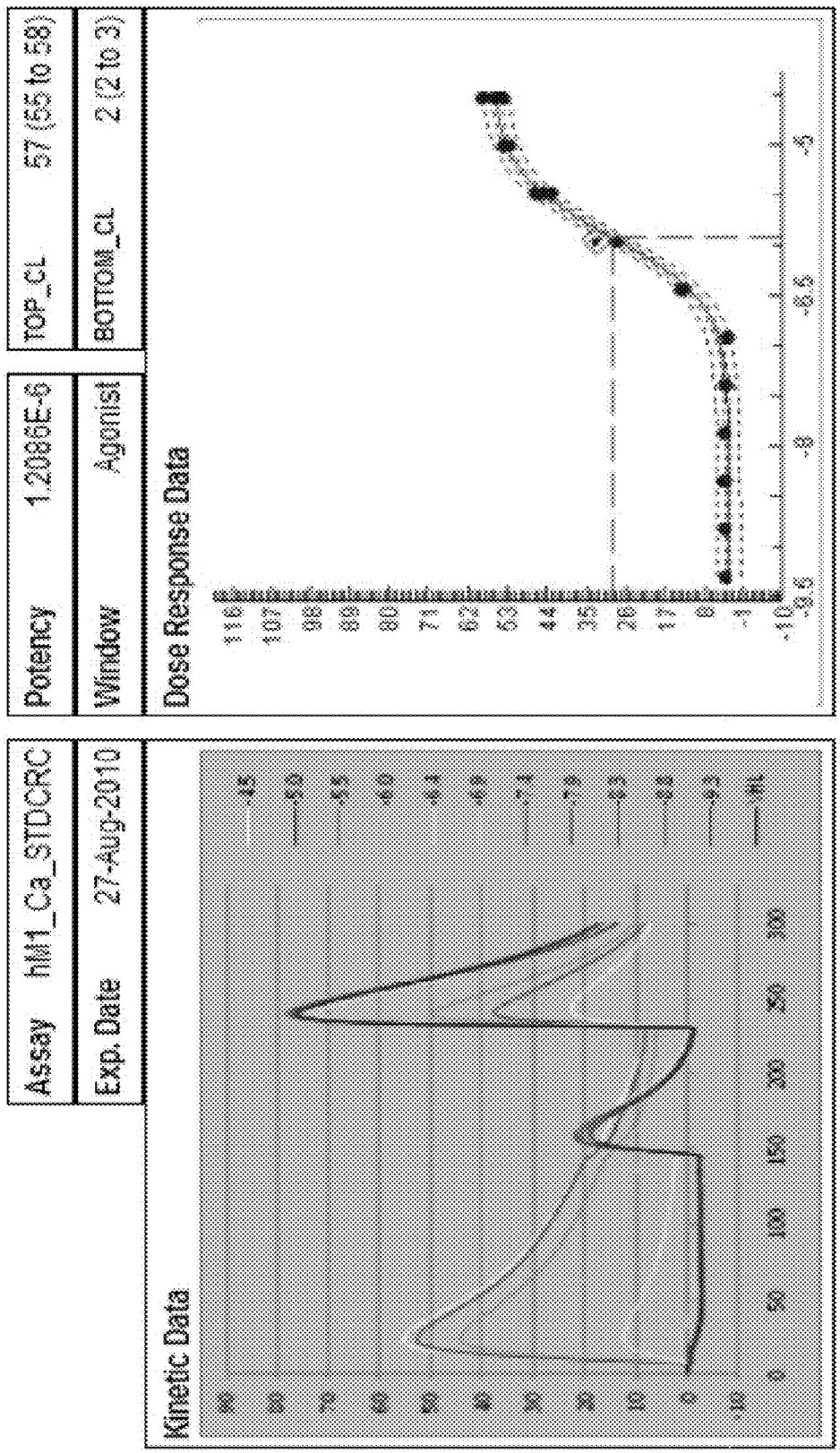
Figure 1.1

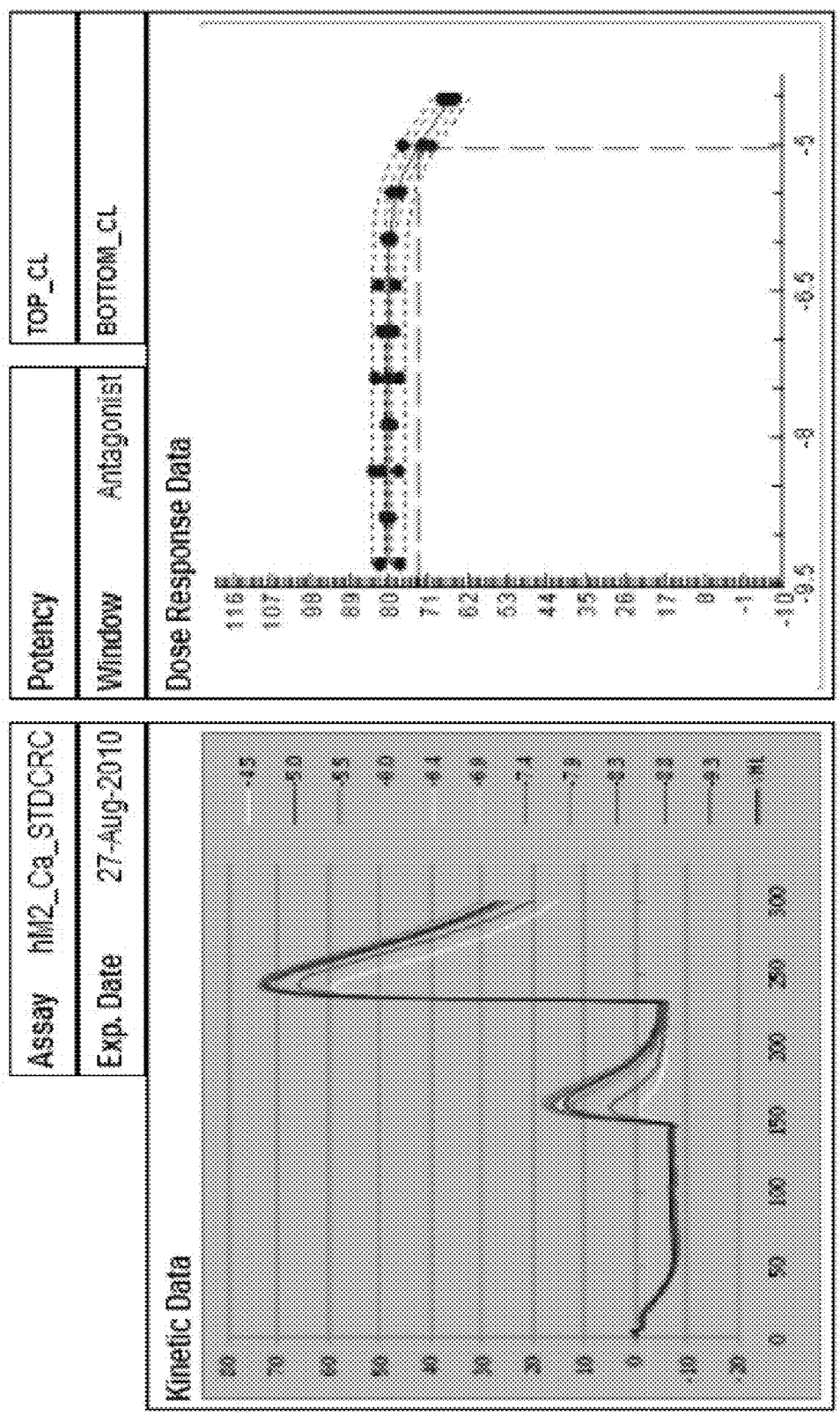
Figure 1.2

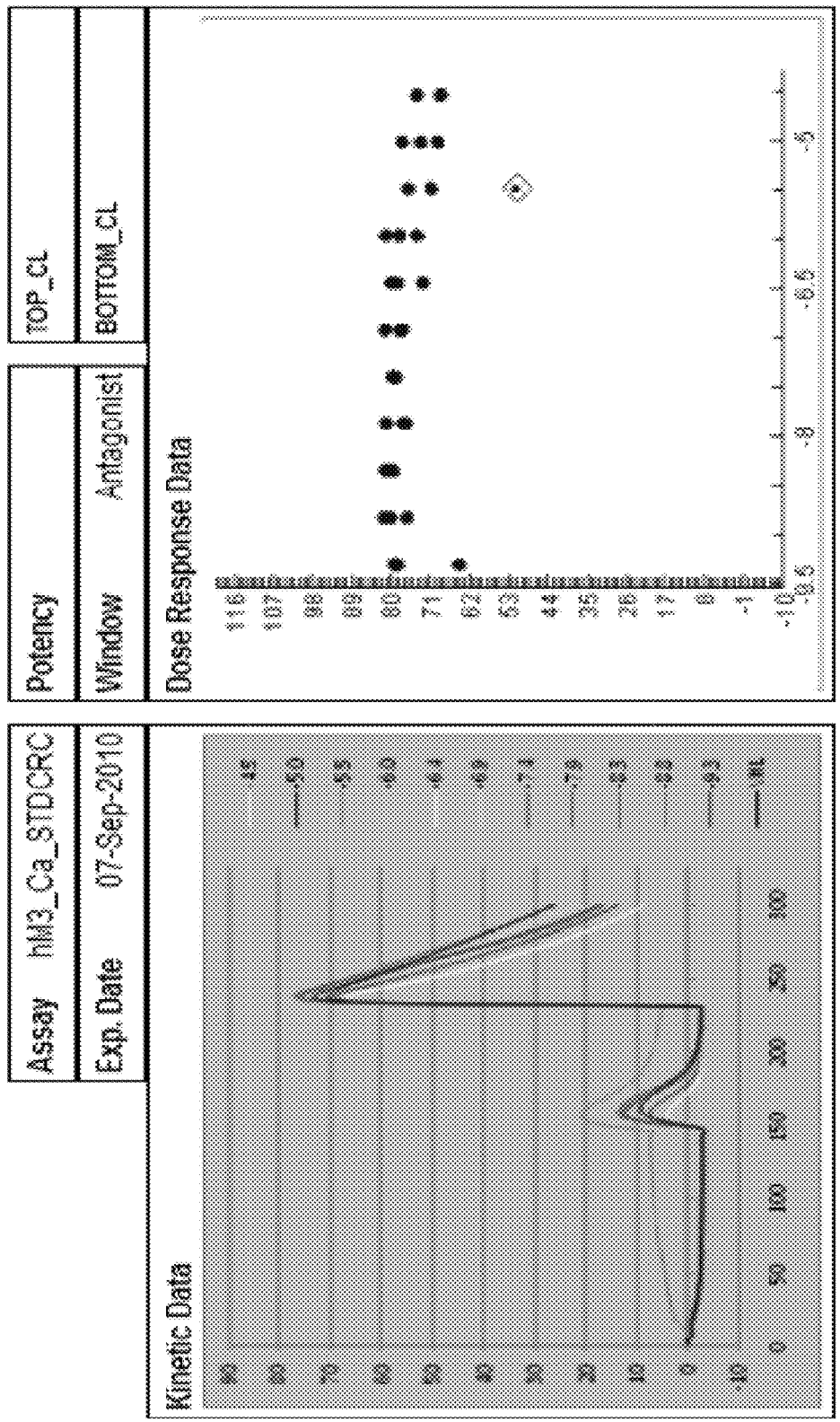
Figure 1.3

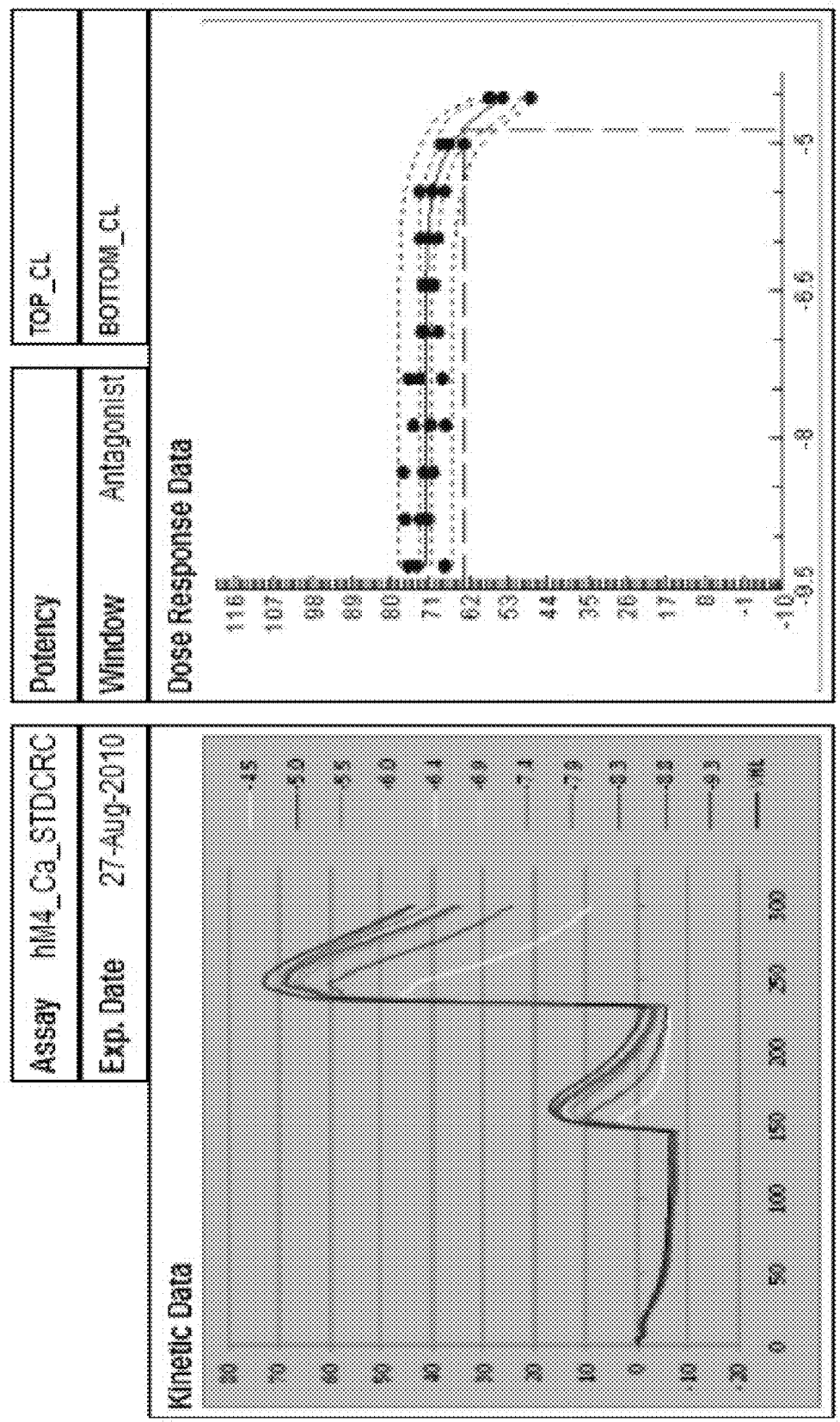
Figure 1.4

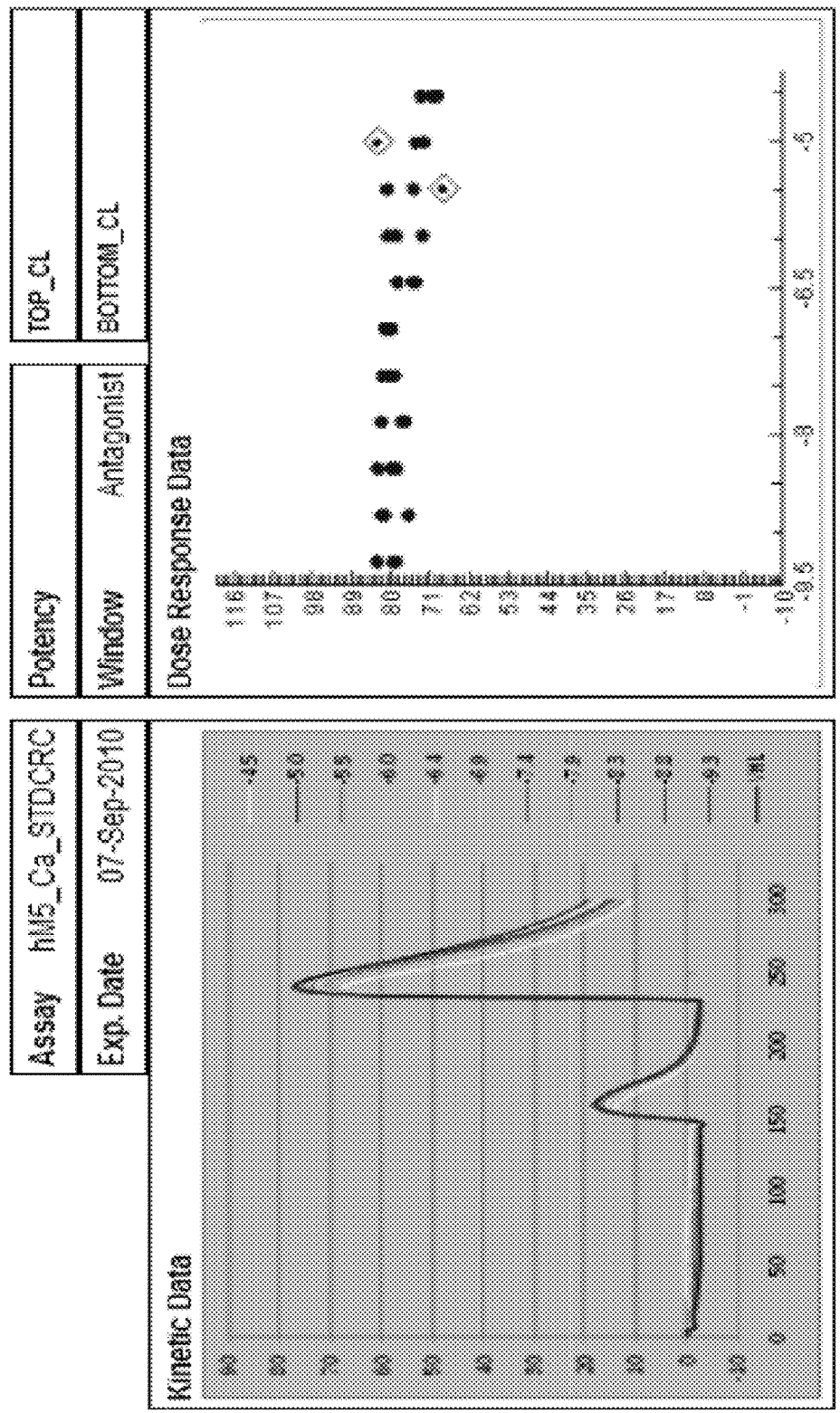
Figure 1.5

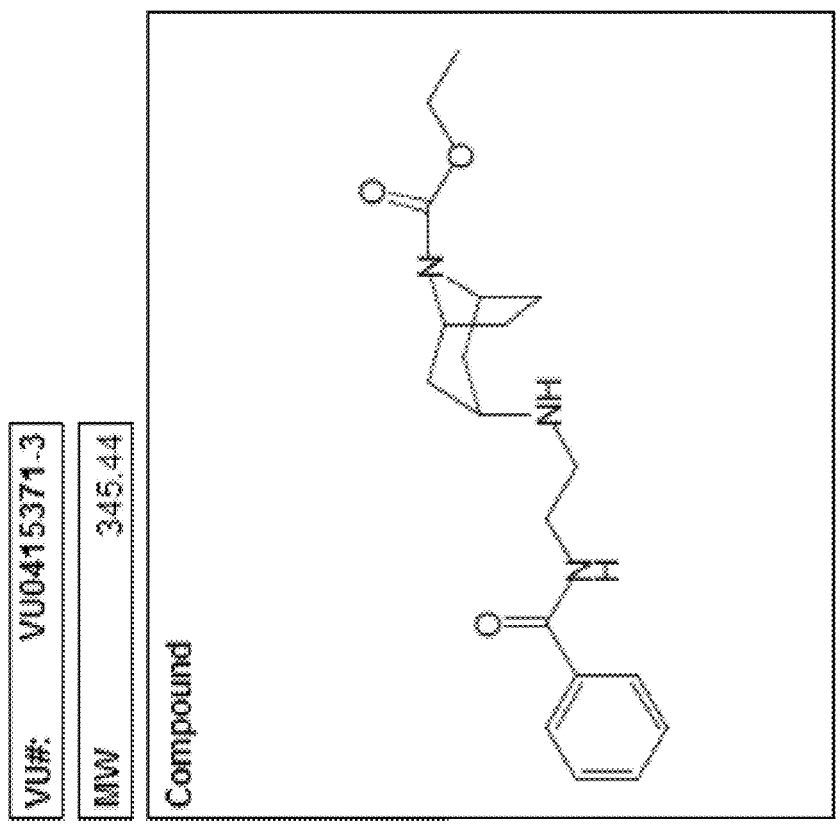
Figure 2.0

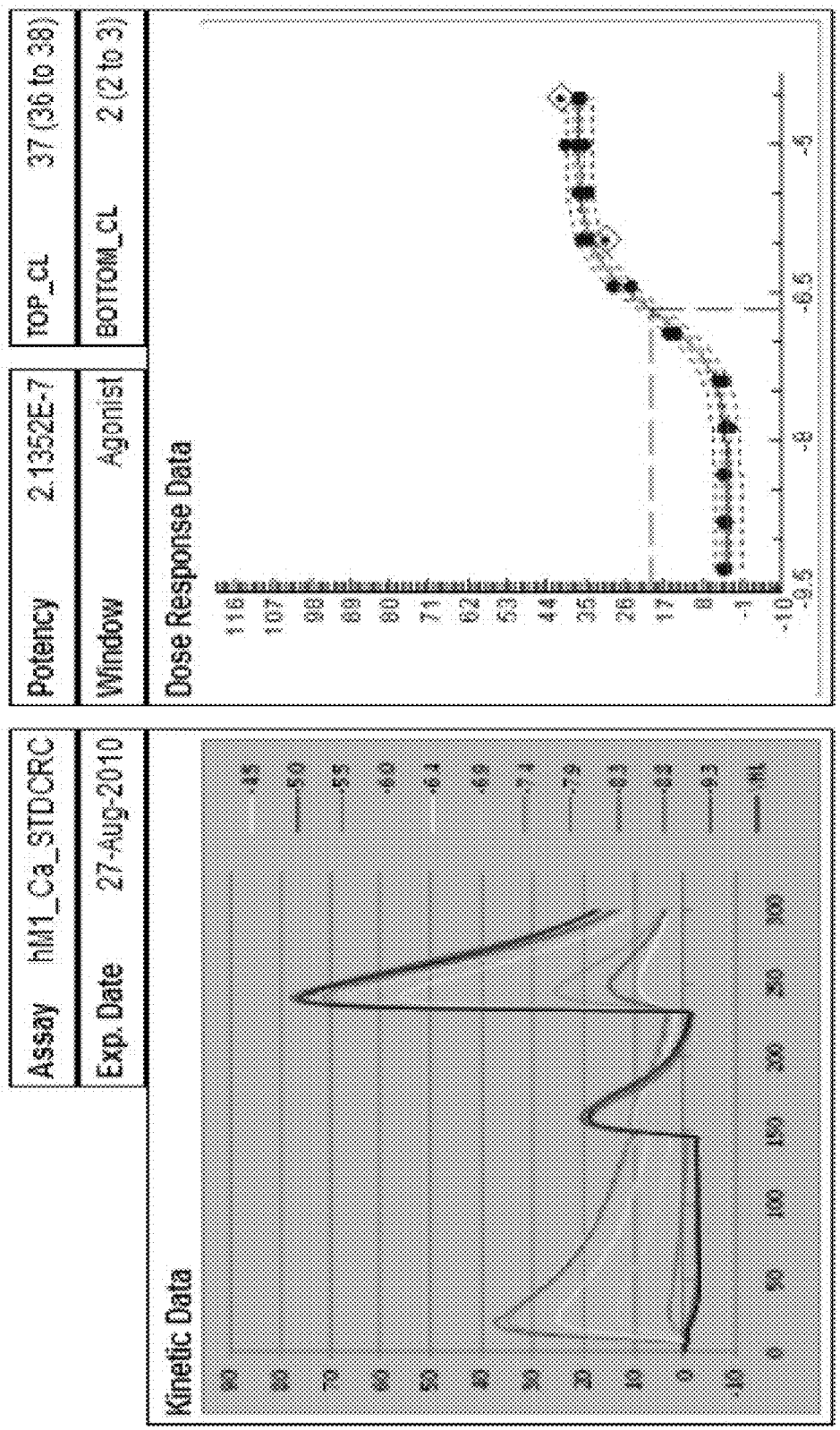
Figure 2.1

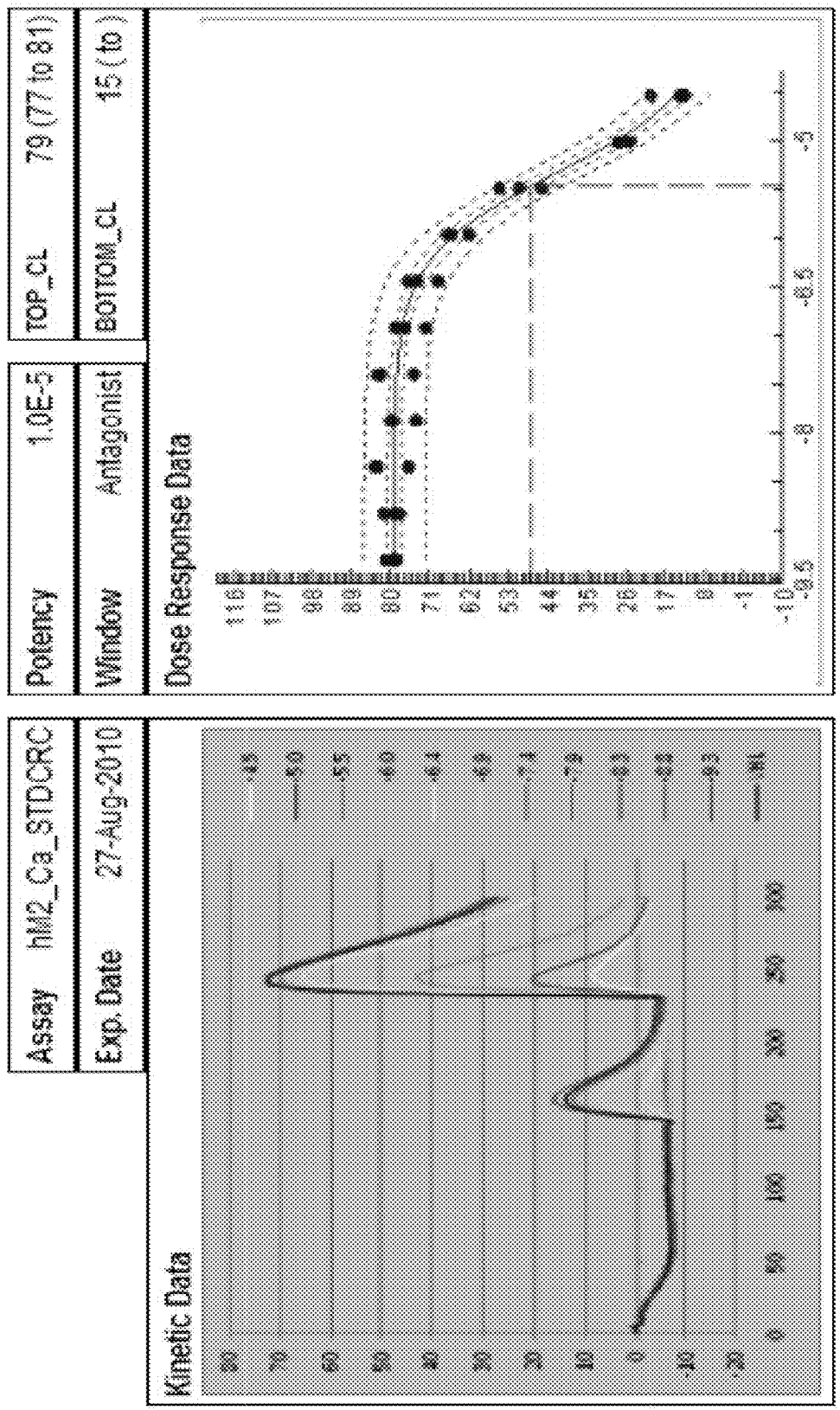
Figure 2.2

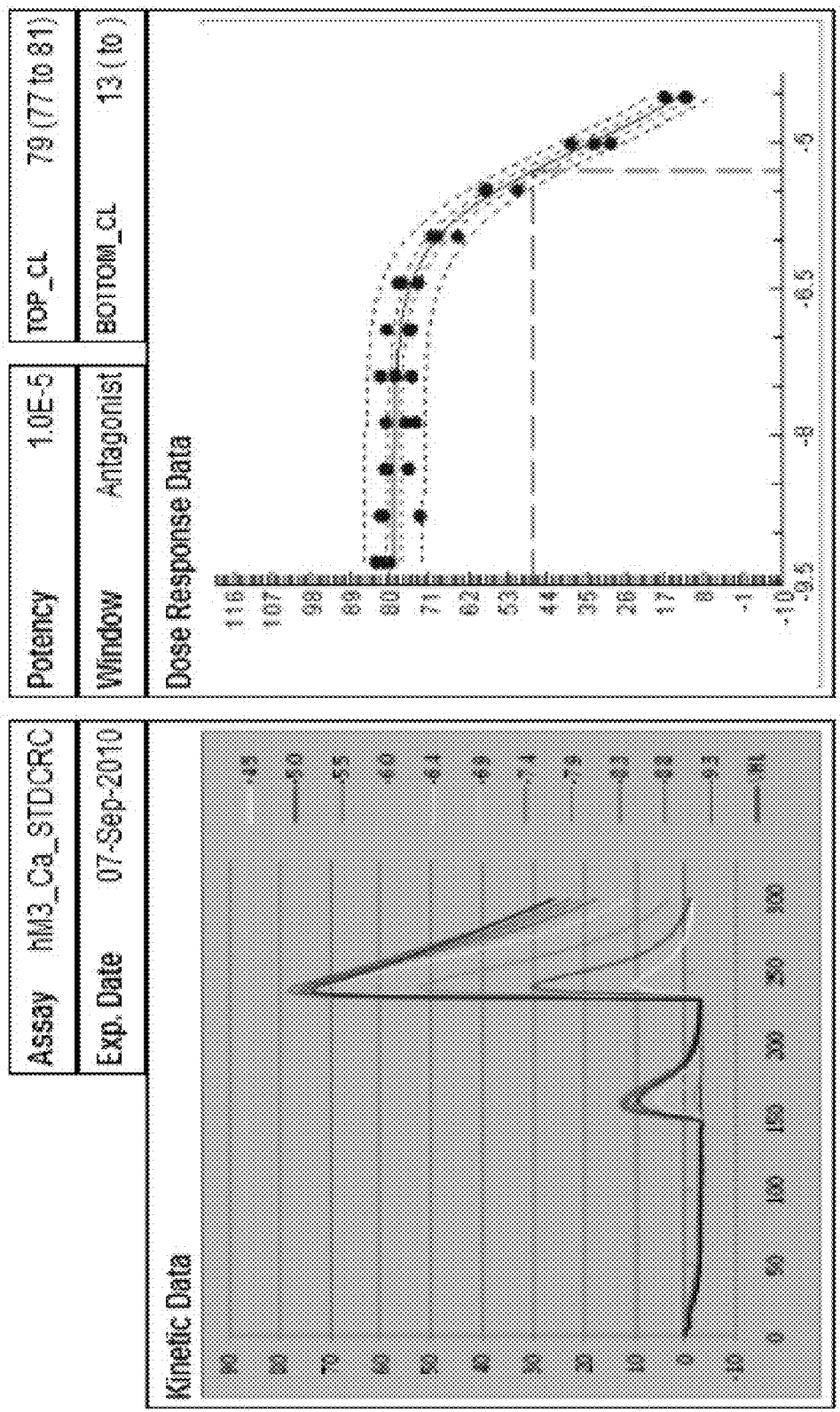
Figure 2.3

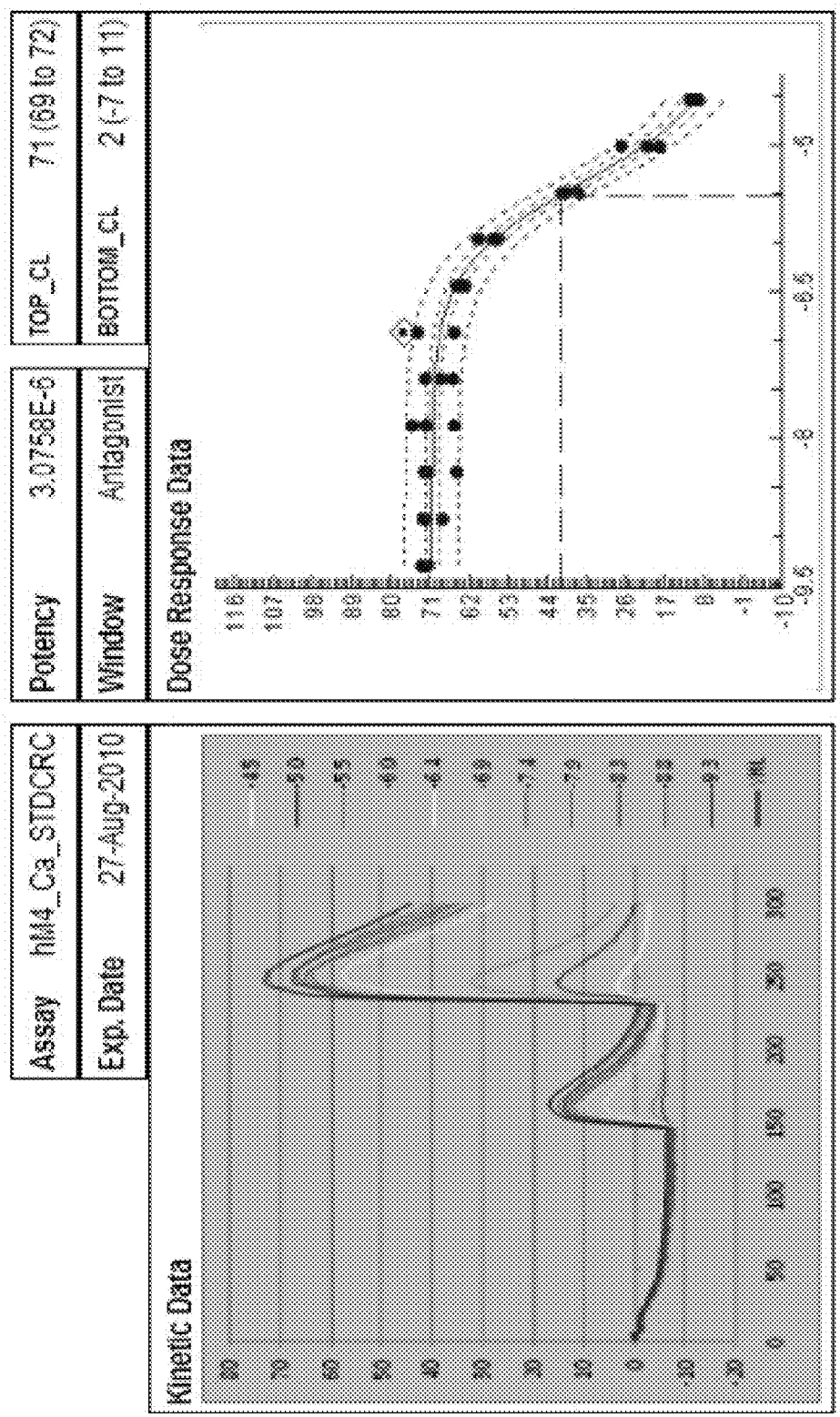
Figure 2.4

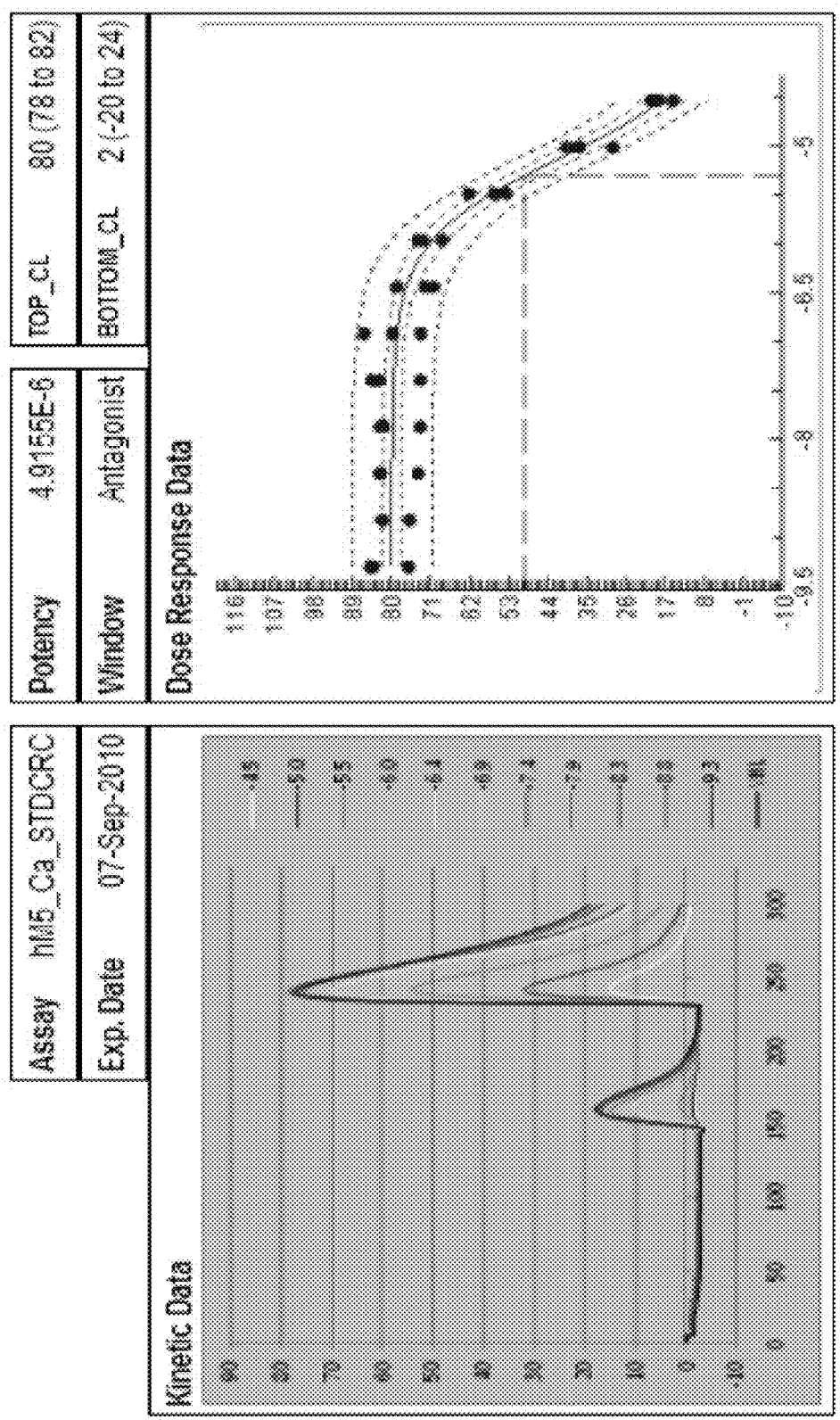
Figure 2.5

ALKYL 3-((2-AMIDOETHYL)AMINO)-8-AZABICYCLO[3.2.1]OCTANE-8-CARBOXYLATE ANALOGS AS SELECTIVE M1 AGONISTS AND METHODS OF MAKING AND USING SAME

CROSS-REFERENCE TO RELATED APPLICATIONS

This application claims the benefit of U.S. Application No. 61/288,717, filed Dec. 21, 2009, which is hereby incorporated herein by reference in its entirety.

STATEMENT REGARDING FEDERALLY SPONSORED RESEARCH

This invention was made with government support under Grant No. MH073676, MH082867 and MH084659 awarded by the National Institutes of Health. The United States government has certain rights in the invention.

BACKGROUND

Alzheimer's Disease (AD) is a neurodegenerative disease affecting the elderly, which results in progressive impairment of memory, language skills and severe behavioral deficits. Hallmarks of the disease include degeneration of cholinergic neurons in the cerebral cortex, hippocampus, basal forebrain and other regions of the brain important for memory and cognition. Other hallmarks of AD include neurofibrillary tangles composed of hyperphosphorylated tau and accumulation of amyloid β peptide (Aβ). Aβ is a 39-43 amino acid peptide produced in the brain by proteolytic processing of β-amyloid precursor protein (APP) by the β-amyloid cleaving enzyme (BACE) and gamma secretase which leads to accumulation of Aβ in the brain, where Aβ 1-40 and 1-42 are the principal aggregate-forming species of Aβ.

Schizophrenia is a debilitating psychiatric disorder characterized by a combination of negative (blunted affect, withdrawal, anhedonia) and positive (paranoia, hallucinations, delusions) symptoms as well as marked cognitive deficits. While schizophrenia remains an idiopathic disorder, it appears to be produced by a complex interaction of biological, environmental, and genetic factors. Over 40 years ago it was found that phencyclidine (PCP) induces a psychotic state in humans that is very similar to that observed in schizophrenic patients. The finding that the main mode of action of PCP is that of a non-competitive antagonist of the N-methyl-D-aspartate (NMDA) subtype of ionotropic glutamate receptor stimulated a series of studies that have led to the development of the NMDA receptor hypofunction model of schizophrenia. Besides schizophrenia, dysfunction of glutamatergic pathways has been implicated in a number of disease states in the human central nervous system (CNS) including cognitive deficits, dementias, Parkinson's disease, Alzheimer's disease and bipolar disorder.

NMDA receptor function can be modulated by activation of G Protein-Coupled Receptors (GPCRs) that are known to physically and/or functionally interact with the NMDA receptor. The NMDA receptor hypofunction hypothesis is a proposal to explain the underlying cause of schizophrenia. According to this hypothesis, any agent that can potentiate NMDA receptor currents, either directly by action on modulatory sites on the NMDA receptor (e.g., the glycine co-agonist binding site) or indirectly by activation of GPCRs known to potentiate NMDA receptor function (e.g. the $M_1$ mAChR), has the potential to ameliorate the symptoms of schizophrenia. In both preclinical and in clinical studies, Xanomeline, an $M_1/M_4$ preferring orthosteric agonist has proved efficacious with regard to positive, negative and cognitive symptoms, indicating that $M_1$ activation is a reasonable approach to the treatment of schizophrenia. More recently, the selective $M_1$ allosteric agonist TBPB demonstrated efficacy in multiple preclinical models of schizophrenia.

Cholinergic neurotransmission involves the activation of nictonic acetylcholine receptors (nAChRs) or the muscarinic acetylcholine receptors (mAChRs) by the binding of the endogenous orthosteric agonist acetylcholine (ACh). Clinical data supports that cholinergic hypofunction contributes to the cognitive deficits of patients suffering from AD and schizophrenia. As a result, acetylcholinesterase inhibitors, which inhibit the hydrolysis of ACh, have been approved in the United States for use in the palliative, but not disease-modifying, treatment of the cognitive deficits in AD patients. An alternative approach to pharmacologically target cholinergic hypofunction is the activation of mAChRs. mAChRs are widely expressed throughout the body. The mAChRs are members of the family A GPCRs and include five subtypes, designated $M_1$-$M_5$. $M_1$, $M_3$ and $M_5$ mainly couple to $G_q$ and activate phospholipase C whereas $M_2$ and $M_4$ mainly couple to $G_{i/o}$ and associated effector systems. These five distinct mAChR subtypes have been identified in the mammalian central nervous system where they are prevalent and differentially expressed. $M_1$-$M_5$ have varying roles in cognitive, sensory, motor and autonomic functions. Thus, without wishing to be bound by theory, it is believed that selective agonists of mAChR subtypes that regulate processes involved in cognitive function could prove superior to AChE inhibitors for treatment of AD and related disorders. The muscarinic $M_1$ receptor has been shown to have a major role in cognitive processing and is believed to have a major role in the pathophysiology of AD.

Evidence suggests that the most prominent adverse effects of AChE inhibitors and other cholinergic agents are mediated by activation of peripheral $M_2$ and $M_3$ mAChRs and include bradycardia, GI distress, excessive salivation, and sweating. In contrast, $M_1$ has been viewed as the most likely subtype for mediating the effects on cognition, attention mechanisms, and sensory processing. Because of this, considerable effort has been focused on developing selective $M_1$ agonists for treatment of AD. Unfortunately, these efforts have been largely unsuccessful because of an inability to develop compounds that are highly selective for the $M_1$ mAChR. Because of this, mAChR agonists that have been tested in clinical studies induce the same adverse effects of AChE inhibitors by activation of peripheral mAChRs. To fully understand the physiological roles of individual mAChR subtypes and to further explore the therapeutic utility of mAChR ligands in AD and other disorders, it can be important to develop compounds that are highly selective activators of $M_1$ and other individual mAChR subtypes.

Previous attempts to develop agonists that are highly selective for individual mAChR subtypes have failed because of the high conservation of the orthosteric ACh binding site. To circumvent problems associated with targeting the highly conserved orthosteric ACh site, a number of groups have shifted their focus to developing compounds that act at allosteric sites on mAChRs that are removed from the orthosteric site and are less highly conserved. This approach is proving to be highly successful in developing selective ligands for multiple GPCR subtypes. In the case of mAChRs, a major goal has been to develop allosteric ligands that selectively increase activity of $M_1$ or other mAChR subtypes. Allosteric activators can include allosteric agonists, that act at a site removed from the orthosteric site to directly activate the receptor in the absence of ACh as well as positive allosteric modulators (PAMs), which do not activate the receptor directly but potentiate activation of the receptor by the endogenous othosteric agonist ACh. Also, it is possible for a single molecule to have both allosteric potentiator and allosteric agonist activity (Conn et al 2009; May et al 2007). Additionally, muscarinic subtype selectivity can be achieved by binding to an allosteric site while at the same time partially or completely overlapping with the orthosteric site. This type of receptor interaction can be referred to as bitopic binding, partially allosteric binding or partially orthosteric binding.

Phase III trials have shown that orthosteric mAChR activators can have efficacy in improving cognitive performance in AD patients. Moreover, data indicate that administration of $M_1$ activators decreases behavioral disturbances, including delusions, hallucinations, outbursts, and other symptoms in patients suffering from neurodegenerative diseases such as Alzheimer's disease. However, dose limiting adverse effects that may be due to lack of $M_1$ mAChR selectivity led to failed launches of previous $M_1$ agonists. In some cases, evidence suggests that mAChR activation also has the potential to be disease-modifying in that these agents may lower Aβ in AD patients. Interestingly, the $M_1$-selective allosteric agonist TBPB was found to display effects on the processing of APP toward the non-amyloidogenic pathway and decrease Aβ 1-40 and 1-42 production in vitro. These data suggest that selective activation of $M_1$ may provide a novel approach for both symptomatic and disease modifying the treatment of Alzheimer's disease.

Despite advances in muscarinic receptor (mAChR) research, there is still a scarcity of compounds that are potent, efficacious and selective activators of the $M_1$ mAChR that are also effective in the treatment of neurological and psychiatric disorders associated with cholinergic dysfunction and diseases in which the muscarinic $M_1$ receptor is involved. These needs and other needs are addressed by the present invention.

SUMMARY

In accordance with the purpose(s) of the invention, as embodied and broadly described herein, the invention, in one aspect, relates to compounds useful as selective agonists of the $M_1$ receptor, which elicit receptor activation by binding at an allosteric site or bitopic site on the $M_1$ receptor, methods of making same, pharmaceutical compositions comprising same, and methods of treating disorders where selective $M_1$ activation would have a therapeutic benefit.

In one aspect, the invention relates to alkyl 3-(2-amidoethyl)amino)-8-azabicyclo[3.2.1]octane-8-carboxylate analogs as selective $M_1$ agonists and methods of making and using same (e.g., a class of 3-(2-amidoethyl)amino)-8-azabicyclo[3.2.1]octane-8-carboxylate analogs and their salts, pharmaceutical compositions comprising them, and their use in therapy of the human body). In a further aspect, the invention relates to a class of compounds that are selective muscarinic $M_1$ receptor agonists and therefore are useful in the treatment of Alzheimer's disease, schizophrenia, sleep disorders, and other diseases in which selective activation of the muscarinic $M_1$ receptor would provide a therapeutic benefit.

Disclosed are compounds having a structure represented by a formula:

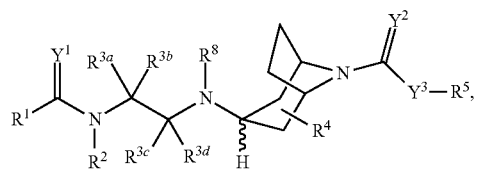

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof.

Also disclosed are compounds having an endo-configured nitrogen substituted bicyclic structure represented by a formula:

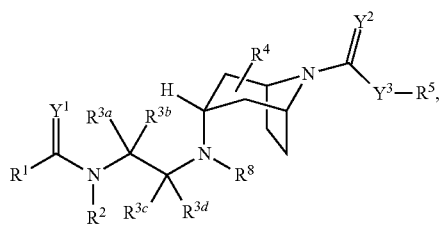

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof.

Also disclosed are compounds having an exo-configured nitrogen substituted bicyclic structure represented by a formula:

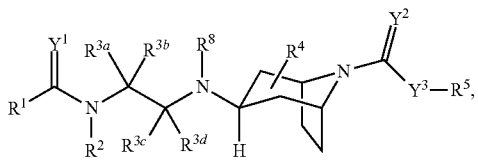

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof.

Also disclosed are methods for preparing a compound comprising the steps of: a. providing an amino compound having a structure represented by a formula:

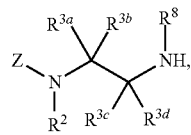

wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^2$ and $R^8$ are independently selected from hydrogen, a hydrolysable residue, or an optionally substituted organic residue comprising 1 to 6 carbons; and wherein Z is hydrogen, a protecting group, or a group having a structure represented by a formula:

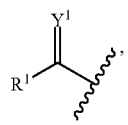

wherein $Y^1$ is O or S; wherein $R^1$ is an optionally substituted organic residue comprising from 1 to 12 carbons, and b. reacting the amino compound with a carboxyl compound having a structure represented by a formula:

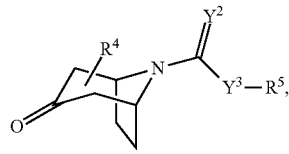

wherein $Y^2$ is O or S; wherein $Y^3$ is a covalent bond, O, S, or N—$R^6$; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; and wherein $R^6$, when present, is independently selected from hydrogen, a hydrolysable residue, and optionally substituted organic residue comprising from 1 to 6 carbons.

Also disclosed are methods for preparing a compound comprising the steps of: a. providing carboxyl compound having a structure represented by a formula:

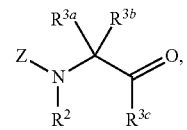

wherein $R^{3a}$, $R^{3b}$, and $R^{3c}$, comprise three substituents independently selected from hydrogen or an optionally substituted organic residue comprising from 1 to 6 carbons; wherein $R^2$ is independently selected from hydrogen, a hydrolysable residue, or an optionally substituted organic residue comprising 1 to 6 carbons; and wherein Z is a protecting group, or a group having a structure represented by a formula:

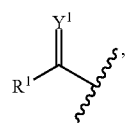

wherein $Y^1$ is O or S; wherein $R^1$ is an optionally substituted organic residue comprising from 1 to 12 carbons, b. reacting the carboxyl compound with an amine compound having a structure represented by a formula:

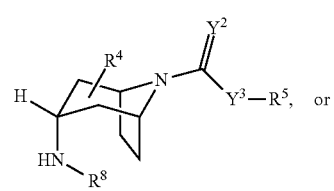

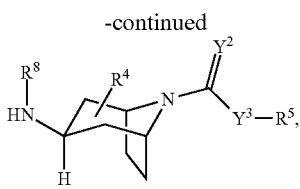

or an endo/exo mixture of the two formulas, wherein $Y^2$ is O or S; wherein $Y^3$ is a covalent bond, O, S, or N—$R^6$; wherein $R^4$ comprises ten substituents independently selected from hydrogen, halogen, hydroxyl, nitrile, nitro, thiol, optionally substituted amino, and optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and optionally substituted organic residue comprising from 1 to 6 carbons; and wherein $R^8$ is hydrogen, or an optionally substituted organic residue comprising 1 to 6 carbons, and c. when Z represents a protecting group, and $R^8$ does not represent hydrogen, the subsequent steps of removing the protecting group and allowing the introduction of an appropriate electrophile to allow the full spectrum of $R^1$ and $Y^1$; wherein $Y^1$ is O or S; wherein $R^1$ is an optionally substituted organic residue comprising from 1 to 12 carbons, or d. when Z represents a protecting group and $R^8$ is hydrogen the subsequent steps of protecting the internal nitrogen with an orthogonal protecting group relative to Z, followed by removal of the protecting group Z, introduction of an appropriate electrophile to allow the full spectrum of $R^1$ and Y'; wherein $Y^1$ is O or S; wherein $R^1$ is an optionally substituted organic residue comprising from 1 to 12 carbons and then deprotection of the internal nitrogen (such that $R^8$ equals hydrogen), with the optional introduction of appropriate electrophiles to allow the full spectrum of $R^8$; wherein $R^8$ is hydrogen, a hydrolysable residue, or an optionally substituted organic residue comprising 1 to 6 carbons.

Also disclosed are the products of the disclosed methods.

Also disclosed are pharmaceutical compositions comprising the disclosed compounds and/or the disclosed products and a pharmaceutically acceptable carrier.

Also disclosed are methods for activating $M_1$ activity in at least one cell, comprising the step of contacting the at least one cell with at least one compound having a structure represented by a formula:

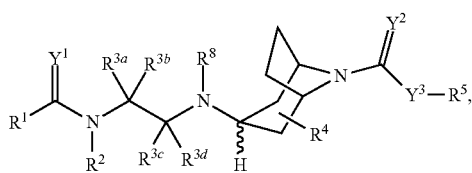

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof, in an amount effective to activate $M_1$ activity response in the at least one cell.

Also disclosed are methods for activating $M_1$ activity in a subject comprising the step of administering to the subject at least one compound having a structure represented by a formula:

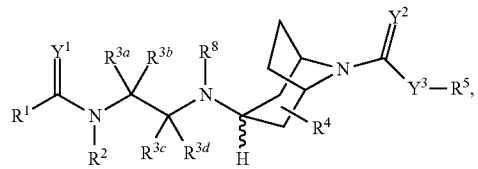

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof, in a dosage and amount effective to activate $M_1$ activity in the subject.

Also disclosed are methods for the treatment of a disorder associated with cholinergic dysfunction in a mammal comprising the step of administering to the mammal at least one compound having a structure represented by a formula:

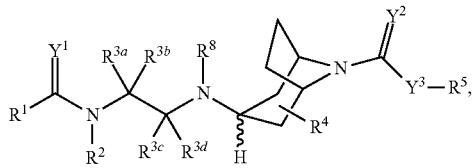

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof, in a dosage and amount effective to treat the disorder in the mammal.

Also disclosed are uses of a compound for $M_1$ receptor activation, the compound having a structure represented by a formula:

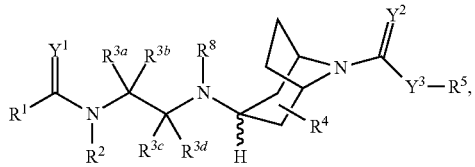

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof.

Also disclosed are methods for manufacturing a medicament comprising combining at least one compound having a structure represented by a formula:

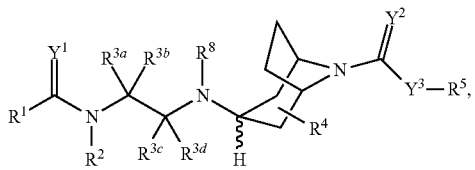

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, with a pharmaceutically acceptable carrier or diluent.

Also disclosed are kits comprising at least one compound having a structure represented by a formula:

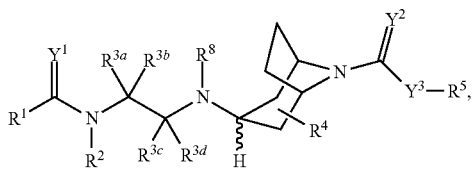

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof, and one or more of: a. at least one agent known to increase $M_1$ receptor activity; b. at least one agent known to decrease $M_1$ receptor activity; c. at least one agent known to treat a cholinergic dysfunction; or d. instructions for treating a disorder associated with cholinergic dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 1.0 describes selectivity of ethyl 3-((3-exo)-(2-benzamidoethyl)amino)-8-azabicyclo[3.2.1]octane-8-carboxylate (see Example 26) for the $hM_1$ receptor vis-à-vis $hM_2$-$hM_5$ receptors. This compound shows $EC_{50}$ of 1.2 µM for $hM_1$, whereas $EC_{50}$ for each of $hM_2$-$hM_5$ is greater than 10 µM.

FIG. 1.1 shows kinetic data and dose response data for the $hM_1$ receptor for ethyl 3((3-exo)-(2-benzamidoethyl)amino)-8-azabicyclo[3.2.1]octane-8-carboxylate (see Example 26). $EC_{50}$ is 1.2 µM for $hM_1$.

FIG. 1.2 shows kinetic data and dose response data for the $hM_1$, receptor for ethyl 3((3-exo)-(2-benzamidoethyl)amino)-8-azabicyclo[3.2.1]octane-8-carboxylate (see Example 26). $EC_{50}$>10 µM for $hM_2$.

FIG. 1.3 shows kinetic data and dose response data for the $hM_3$ receptor for ethyl 3((3-exo)-(2-benzamidoethyl)amino)-8-azabicyclo[3.2.1]octane-8-carboxylate (see Example 26). $EC_{50}$>10 µM for $hM_3$.

FIG. 1.4 shows kinetic data and dose response data for the $hM_4$ receptor for ethyl 3((3-exo)-(2-benzamidoethyl)amino)-8-azabicyclo[3.2.1]octane-8-carboxylate (see Example 26). $EC_{50}$>10 µM for $hM_4$.

FIG. 1.5 shows kinetic data and dose response data for the $hM_5$ receptor for ethyl 3((3-exo)-(2-benzamidoethyl)amino)-8-azabicyclo[3.2.1]octane-8-carboxylate (see Example 26). $EC_{50}$>10 µM for the $hM_5$.

FIG. 2.0 describes selectivity of ethyl 3-((3-endo)-(2-benzamidoethyl)amino)-8-azabicyclo[3.2.1]octane-8-carboxylate (see Example 27) for the $hM_1$ receptor vis-à-vis $hM_2$-$hM_5$ receptors. This compound shows $EC_{50}$ of 214 nM for $hM_1$, whereas $EC_{50}$ for each of $hM_2$-$hM_5$ is much greater.

FIG. 2.1 shows kinetic data and dose response data for the $hM_1$ receptor for ethyl 3-((3-endo)-(2-benzamidoethyl)amino)-8-azabicyclo[3.2.1]octane-8-carboxylate (see Example 27). $EC_{50}$ is 214 nM for $hM_1$.

FIG. 2.2 shows kinetic data and dose response data for the $hM_2$ receptor for ethyl 3-((3-endo)-(2-benzamidoethyl)amino)-8-azabicyclo[3.2.1]octane-8-carboxylate (see Example 27). $EC_{50}$ is about 3 µM for $hM_2$.

FIG. 2.3 shows kinetic data and dose response data for the $hM_3$ receptor for ethyl 3-((3-endo)-(2-benzamidoethyl)amino)-8-azabicyclo[3.2.1]octane-8-carboxylate (see Example 27). $EC_{50}$ is about 10 µM for $hM_3$.

FIG. 2.4 shows kinetic data and dose response data for the $hM_4$ receptor for ethyl 3-((3-endo)-(2-benzamidoethyl)amino)-8-azabicyclo[3.2.1]octane-8-carboxylate (see Example 27). $EC_{50}$ is about 3 µM for $hM_4$.

FIG. 2.5 shows kinetic data and dose response data for the $hM_5$ receptor for ethyl 3-((3-endo)-(2-benzamidoethyl)amino)-8-azabicyclo[3.2.1]octane-8-carboxylate (see Example 27). $EC_{50}$ is about 10 µM for $hM_5$.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance may or may not occur, and that the description includes instances where said event or circumstance occurs and instances where it does not.

As used herein, the term "orthosteric site" refers to the primary binding site on a receptor that is recognized by the endogenous ligand or agonist for that receptor. For example, the orthosteric site in the $M_1$ receptor is the site that acetylcholine binds.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by selective activation of the $M_1$ receptor" means having been subjected to a physical examination by a person of skill, for example, a physician, and found to have a condition that can be diagnosed or treated by a compound or composition that can favorably activate the $M_1$ receptor. As a further example, "diagnosed with a need for selective activation of the $M_1$ receptor" refers to having been subjected to a physical examination by a person of skill, for example, a physician, and found to have a condition characterized by a deficit of $M_1$ receptor function. Such a diagnosis can be in reference to a disorder, such as a neurological and/or psychiatric disorder, obesity, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to $M_1$ receptor activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response. In a yet further aspect, the response is in vitro.

As used herein, "$EC_{50}$" refers to the concentration of a substance (e.g., a compound or a drug) that is required to achieve 50% maximal response of a biological process, or component of a process, including a protein, subunit, organelle, ribonucleoprotein, etc., be it activation (agonist), inactivation (antagonist) or positive allosteric modulation (PAM). In one aspect, an $EC_{50}$ can refer to the concentration of a substance (e.g., a compound or a drug) that is required for 50% agonism of a biological process, or component of a process, including a protein, subunit, organelle, ribonucleoprotein, etc.

In certain aspects, the term "$EC_{50}$" can be used as shorthand terminology with reference to inactivation (antagonist) activity. Those of skill readily understand that "$EC_{50}$" for an antagonist is intended to be synonymous with "$IC_{50}$" and is intended to refer to the concentration of a substance (e.g., a compound or a drug) that is required to achieve 50% maximal response of a biological process or component of a process.

As used herein, "$IC_{50}$" refers to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance. In a yet further aspect, the inhibition is measured in vitro.

In certain aspects, the term "$IC_{50}$" can be used as shorthand terminology with reference to activation (agonist) activity. Those of skill readily understand that "$IC_{50}$" for an agonist is intended to be synonymous with "$EC_{50}$" and is intended to refer to the concentration of a substance (e.g., a compound or a drug) that is required to achieve 50% maximal response of a biological process or component of a process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$C(O)(CH_2)_8C(O)$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2, 3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1$C(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$—CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ_2$; —C(S)NR$^\circ_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —(C$_{1-4}$ straight or branched)alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, —(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —C(O)SR$^\bullet_3$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

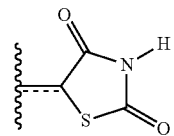

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z)

isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (ee). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

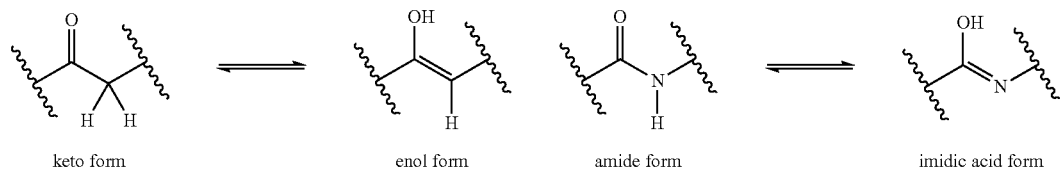 [SMILES: *CC(*)=O ; */C=C(/*)O ; *NC(*)=O ; */N=C(/*)O]

keto form   enol form   amide form   imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

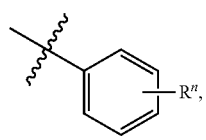

which is understood to be equivalent to a formula:

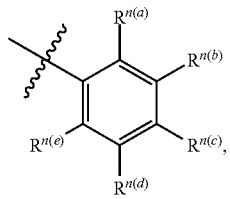

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Compounds described herein contain substituted bicyclic structures potentially giving rise to endo/exo isomers. For the two substituents at a given atom, on a given bicycle, the endo-position represents the location (side) closest to the largest bridge, while the exo-position is the one that places the substituent furthest from the largest bridge. This is illustrated in the figure below for the two isomeric hydrogens: $H_{exo}$ and $H_{endo}$.

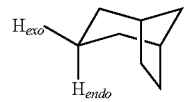

However, a mixture of endo/exo isomers, or a single isomer of undefined configuration, can be represent by various structures, such as those shown here for the [3.2.1] bicycle:

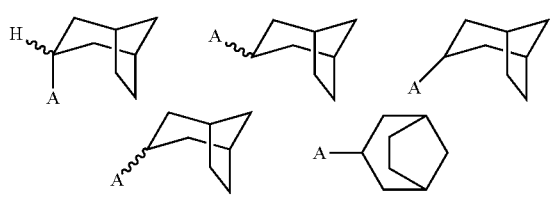

Unless stated to the contrary, the invention includes all such possible isomers, as well as mixtures of such isomers.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds, or pharmaceutically acceptable derivatives thereof, useful as selective activators of the $M_1$ receptor, in this case allosteric agonists, or bitopic agonists. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to compounds having a structure represented by a formula:

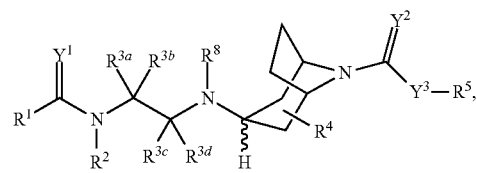

wherein Y $R^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof.

For example, in a further aspect, the invention relates to compounds having a structure represented by a formula:

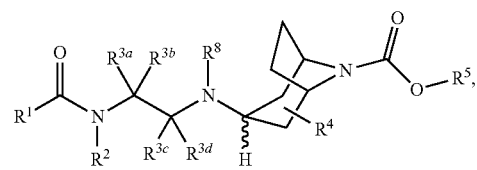

wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ independently comprise hydrogen or optionally substituted organic residue comprising from 1 to 6 carbons; wherein $R^4$ comprises ten substituents independently selected from hydrogen, halogen, hydroxyl, nitrile, nitro, thiol, optionally substituted amino, and optionally substituted organic residue comprising from 1 to 6 carbons; and wherein $R^5$ is an optionally substituted organic residue comprising from 1 to 6 carbons, and wherein $R^8$ is hydrogen, a hydrolysable residue, or an optionally substituted organic residue comprising 1 to 6 carbons; or a pharmaceutically acceptable derivative thereof.

In a further aspect, a compound has a structure represented by a formula:

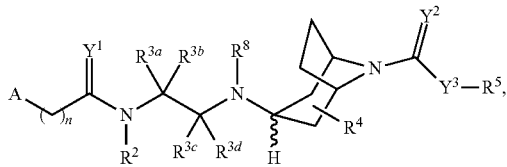

wherein n is 0 or 1; and wherein A is an optionally substituted cyclic organic residue selected from aryl, heteroaryl, cycloalkyl, heterocycloalkyl, cycloalkenyl, and heterocycloalkenyl.

In a further aspect, a compound has a structure represented by a formula:

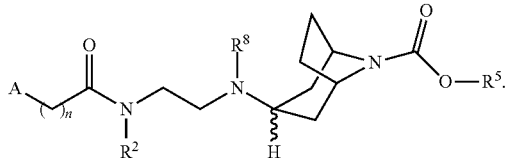

In a further aspect, n is 0. In a further aspect, n is 1. In a further aspect, $R^8$ is hydrogen. In a further aspect, $R^5$ is methyl, ethyl, propyl, or butyl.

In a further aspect, a compound has a structure represented by a formula:

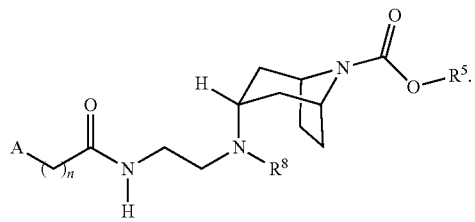

In a further aspect, n is 0. In a further aspect, n is 1. In a further aspect, $R^8$ is hydrogen. In a further aspect, $R^5$ is methyl, ethyl, propyl, or butyl.

In a further aspect, a compound has a structure represented by a formula:

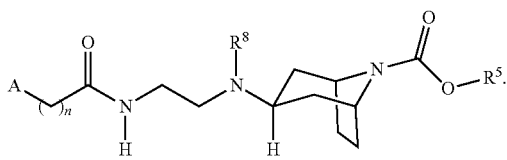

In a further aspect, n is 0. In a further aspect, n is 1. In a further aspect, $R^8$ is hydrogen. In a further aspect, $R^5$ is methyl, ethyl, propyl, or butyl.

In a further aspect, a compound has a structure represented by a formula:

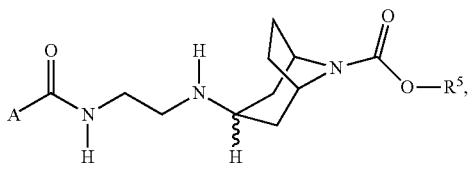

wherein $R^5$ is an optionally substituted organic residue comprising 1 to 4 carbons; and wherein A is an optionally substituted cyclic organic residue selected from aryl, heteroaryl, cycloalkyl, heterocycloalkyl, cycloalkenyl, and heterocycloalkenyl.

In a further aspect, a compound has a structure represented by a formula:

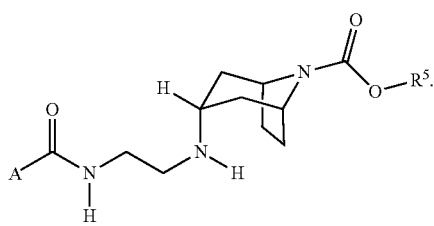

In a further aspect, a compound has a structure represented by a formula:

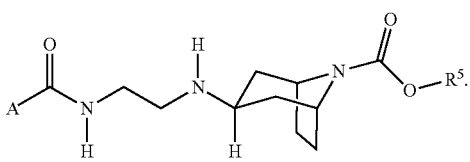

In a further aspect, $R^5$ is an optionally substituted organic residue selected from methyl, ethyl, propyl, or butyl. In a further aspect, $R^5$ is substituted with 0-3 groups selected from fluoro, chloro, bromo, hydroxyl, alkoxyl, nitrile, nitro, thiol, and optionally substituted amino. In a further aspect, A is selected from:

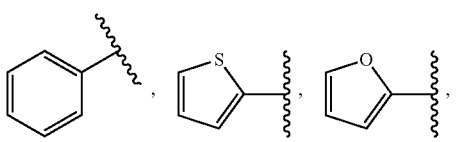

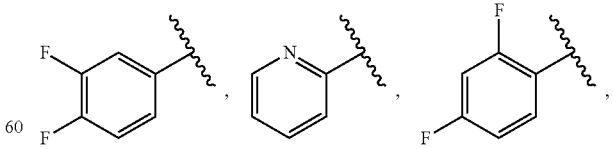

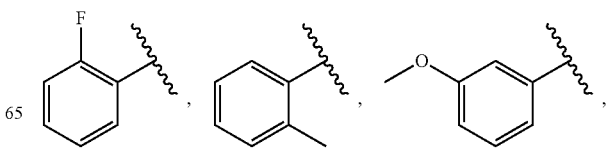

-continued

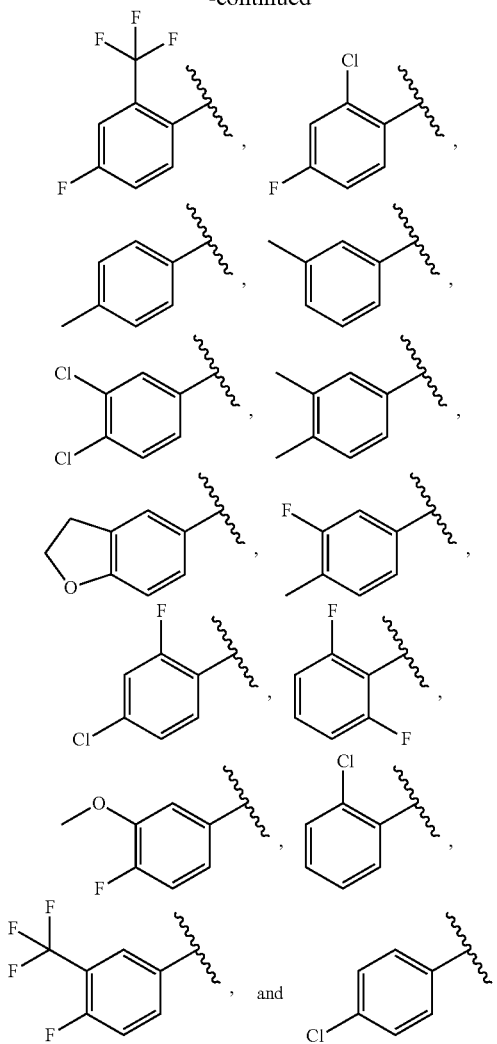

a. Y¹ Groups

In one aspect, $Y^1$ is O or S. For example, in a further aspect, $Y^1$ is O. In a yet further aspect, $Y^1$ is S. In a further aspect, $Y^1$ and $Y^2$ are the same. In a further aspect, both $Y^1$ and $Y^2$ are O. In a further aspect, both $Y^1$ and $Y^2$ are S. In a further aspect, $Y^1$ and $Y^2$ are different. In a further aspect, $Y^1$ is O, and $Y^2$ is S. In a further aspect, $Y^1$ is S, and $Y^2$ is O.

b. Y² Groups

In one aspect, $Y^2$ is O or S. For example, in a further aspect, $Y^2$ is O. In a yet further aspect, $Y^2$ is S. In a further aspect, both $Y^2$ and $Y^3$ are O. In a further aspect, $Y^2$ and $Y^3$ are different. For example, in one aspect, $Y^2$ is S, and $Y^3$ is O. In a further aspect, $Y^2$ is O, and $Y^3$ is a covalent bond. In a further aspect, $Y^2$ is O, and $Y^3$ is N—$R^6$. As a further example, in one aspect, $Y^2$ is S, and $Y^3$ is a covalent bond. In a further aspect, $Y^2$ is S, and $Y^3$ is N—$R^6$.

c. Y³ Groups

In one aspect, $Y^3$ is a covalent bond, O, or N—$R^6$. In a further aspect, $Y^3$ is selected from O and N—$R^6$. In a further aspect, $Y^3$ is a covalent bond. In a further aspect, $Y^3$ is O. In a further aspect, $Y^3$ is N—$R^6$.

In one particular aspect, $Y^1$ is O, $Y^2$ is O, and $Y^3$ is O.

d. R¹ Groups

In one aspect, $R^1$ is an optionally substituted organic residue comprising from 1 to 12 carbons. In a further aspect, $R^1$ is selected from optionally substituted C1-C12 alkyl or C2-C12 alkenyl or C2-C12 alkynyl, optionally substituted C1-C12 heteroalkyl or C2-C12 heteroalkenyl or C2-C12 heteroalkynyl, optionally substituted C3-C12 cycloalkyl or C3-C12 cycloalkenyl, optionally substituted C3-C12 heterocycloalkyl or C3-C12 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, and alkylamine-carbonyl.

In one aspect, $R^1$ is an optionally substituted organic residue comprising 1 to 12 carbons, including methyl, ethyl, propyl, butyl, pentyl, hexyl, heptyl, octyl, nonyl, decyl, undecyl, and dodecyl. In a further aspect, $R^1$ is an optionally substituted organic residue comprising 1 to 10 carbons, including methyl, ethyl, propyl, butyl, pentyl, hexyl, heptyl, octyl, nonyl, and decyl. In a further aspect, $R^1$ is an optionally substituted organic residue comprising 1 to 8 carbons, including methyl, ethyl, propyl, butyl, pentyl, hexyl, heptyl, and octyl. In a further aspect, $R^1$ is an optionally substituted organic residue comprising 1 to 6 carbons, including methyl, ethyl, propyl, butyl, pentyl, and hexyl. In a further aspect, $R^1$ can be an optionally substituted organic residue comprising 1 to 4 carbons, including methyl, ethyl, propyl, and butyl.

In a further aspect, $R^1$ has a structure represented by a formula:

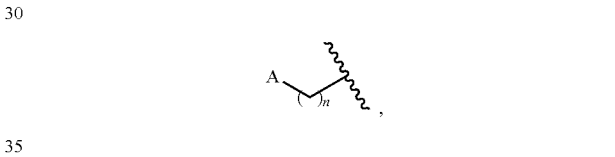

wherein n is 0 or 1; and wherein A is an optionally substituted cyclic organic residue selected from aryl, heteroaryl, cycloalkyl, heterocycloalkyl, cycloalkenyl, and heterocycloalkenyl. In a further aspect, n is 0. In a further aspect, n is 1.

In a further aspect, A is optionally substituted aryl selected from phenyl and naphthyl.

In a further aspect, A is optionally substituted heteroaryl selected from oxazolyl, isoxazolyl, pyrazolyl, furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

In a further aspect, A is optionally substituted cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, A is optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, A is optionally substituted cycloalkenyl selected from cyclobutenyl, cyclopentenyl, cyclopentadienyl, cyclohexenyl, cyclohexadienyl, cycloheptenyl, cycloheptadienyl, cyclooctenyl, cyclooctadienyl, cyclononenyl, and cyclononadienyl.

In a further aspect, A is optionally substituted heterocycloalkenyl comprising pyrazolinone, imidazolinone, or a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, A is selected from:

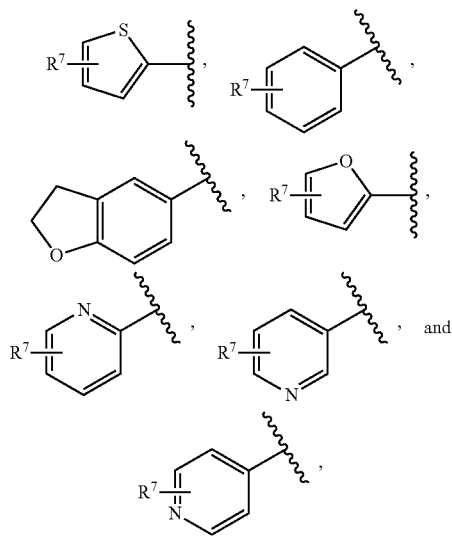

wherein $R^7$ comprises 0-3 groups substituted for hydrogen and independently selected from C1 to C4 alkyl, C1 to C4 haloalkyl, halide, hydroxyl, trifluoromethyl, cyano, C1 to C4 alkoxy, thiol, C1 to C4 alkylsulfonyl, C1 to C4 carboxamide, and C1 to C4 sulfonamide.

In a further aspect, n is 0, and A is selected from:

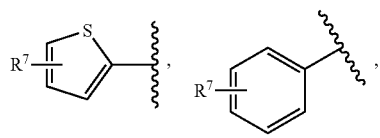

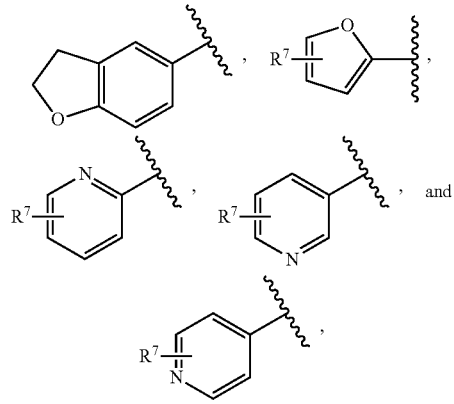

wherein $R^7$ comprises 0-3 groups substituted for hydrogen and independently selected from C1 to C4 alkyl, C1 to C4 haloalkyl, halide, hydroxyl, trifluoromethyl, cyano, C1 to C4 alkoxy, thiol, C1 to C4 alkylsulfonyl, C1 to C4 carboxamide, and C1 to C4 sulfonamide.

In a further aspect, n is 1, and A is selected from:

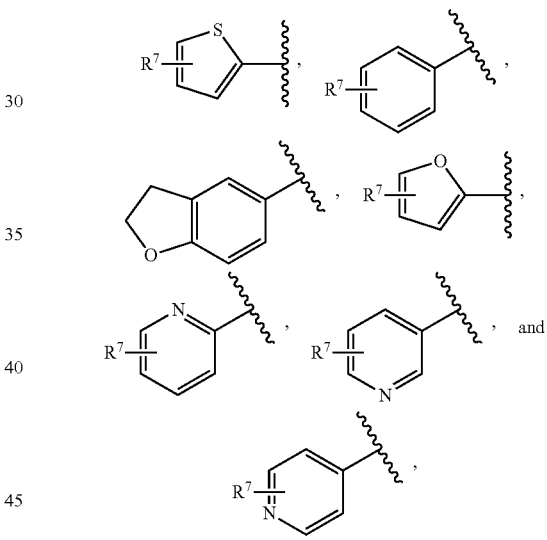

wherein $R^7$ comprises 0-3 groups substituted for hydrogen and independently selected from C1 to C4 alkyl, C1 to C4 haloalkyl, halide, hydroxyl, trifluoromethyl, cyano, C1 to C4 is alkoxy, thiol, C1 to C4 alkylsulfonyl, C1 to C4 carboxamide, and C1 to C4 sulfonamide.

In a further aspect, A is selected from:

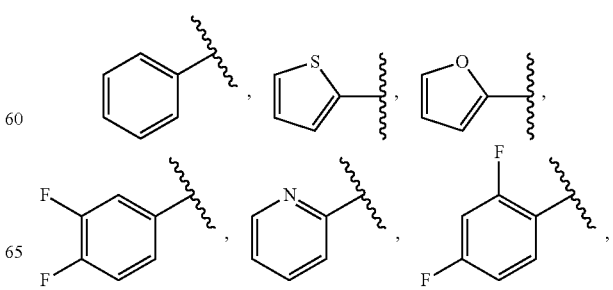

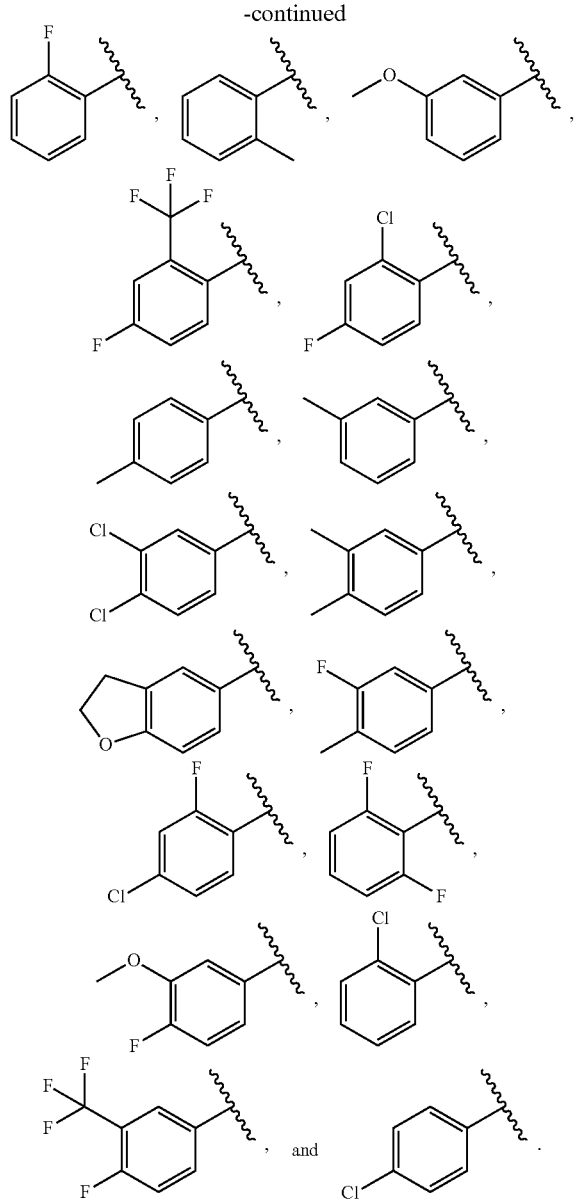
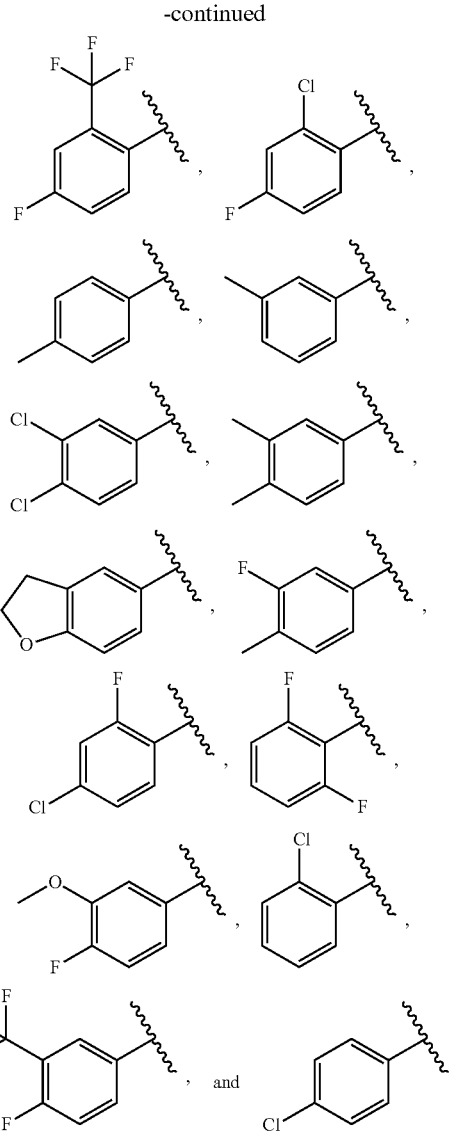
In a further aspect, n is 0, and A is selected from:
In a further aspect, n is 1, and A is selected from:
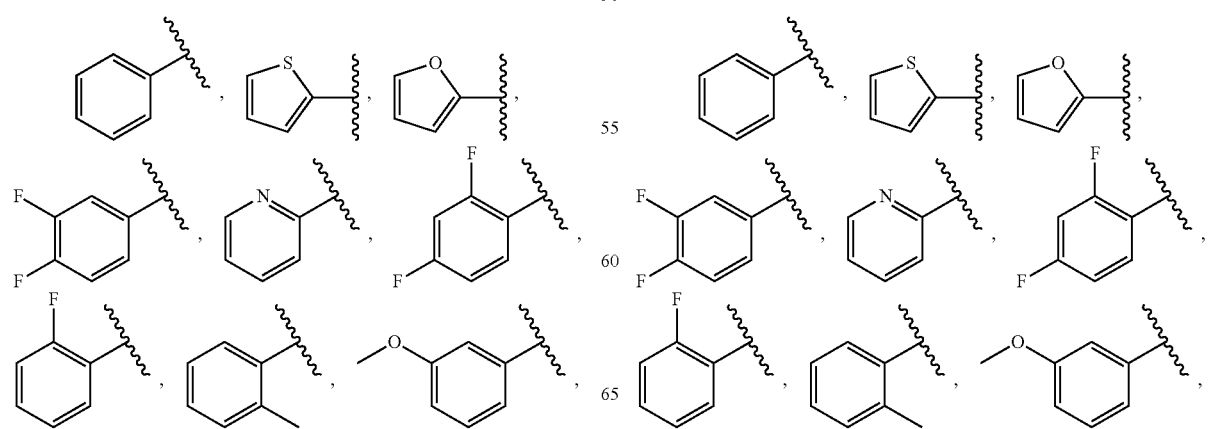

-continued

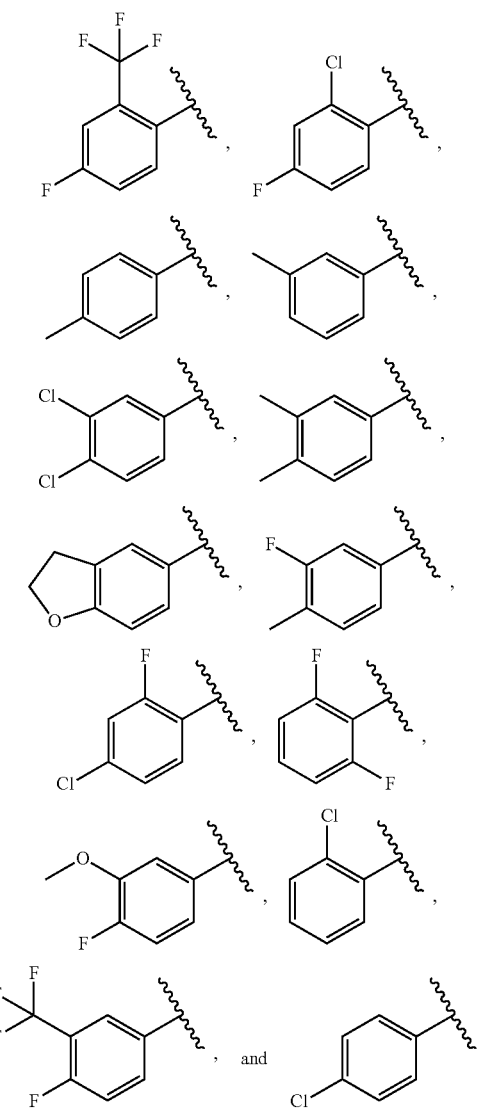

In a further aspect, n is 1, and A is selected from:

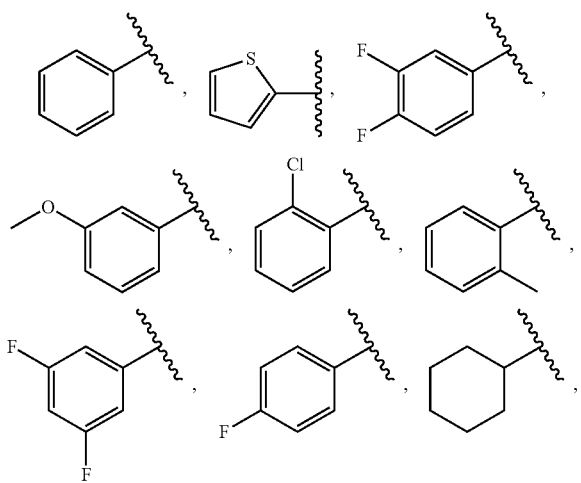

-continued

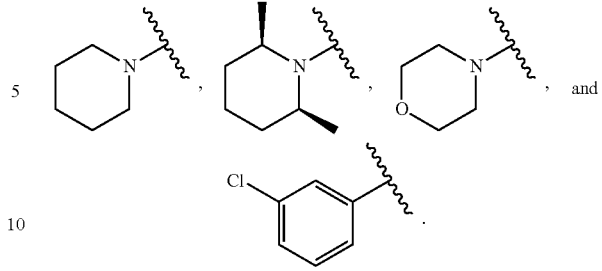

e. R² Groups

In one aspect, R² is hydrogen, a hydrolysable residue, or an optionally substituted organic residue comprising 1 to 6 carbons. In a further aspect, R² is hydrogen. In a further aspect, R² is a hydrolysable residue, for example, a protecting group (e.g., a butuloxycarbonyl group or a silyl protecting group). In a further aspect, R² is an optionally substituted organic residue comprising 1 to 6 carbons, including methyl, ethyl, propyl, butyl, pentyl, and hexyl. In a further aspect, R² can be an optionally substituted organic residue comprising 1 to 4 carbons, including methyl, ethyl, propyl, and butyl.

f. R³ Groups

In one aspect, each R³ is independently hydrogen or optionally substituted organic residue comprising from 1 to 6 carbons. For example, $R^{3a}$ and $R^{3b}$ can be independently selected from optionally substituted C1-C6 alkyl, including methyl, ethyl, propyl, butyl, pentyl, and hexyl. In a further aspect, R³ can be an optionally substituted organic residue comprising 1 to 4 carbons, including methyl, ethyl, propyl, and butyl. In one aspect, $R^{3a}$ and $R^{3b}$ are hydrogen. In one aspect, all of $R^{3a}$, $R^{3b}$, $R^{3c}$, and $R^{3d}$ are hydrogen. In a further aspect, one of $R^{3a}$, $R^{3b}$, $R^{3c}$, and $R^{3d}$ is optionally substituted C1-C6 alkyl and the remaining of $R^{3a}$, $R^{3b}$, $R^{3c}$, and $R^{3d}$ are hydrogen.

g. R⁴ Groups

In one aspect, R⁴ comprises ten substituents independently selected from hydrogen, halogen, hydroxyl, nitrile, nitro, thiol, optionally substituted amino, and optionally substituted organic residue comprising from 1 to 6 carbons. For example, R⁴ can be hydrogen or up to ten (i.e., 0, 1, 2, 3, 4, 5, 6, 7, 8, 9, or 10) groups substituted for hydrogen on the azabicyclo [3.2.1]octane ring.

In a further aspect, all of R⁴ can be hydrogen. In a further aspect, any of R⁴ can be hydrogen. In a further aspect, R⁴ can be hydrogen, halogen, hydroxyl, nitrile, nitro, thiol, or optionally substituted amino. In a further aspect, R⁴ can be an optionally substituted organic residue comprising 1 to 6 carbons, including methyl, ethyl, propyl, butyl, pentyl, and hexyl. In a further aspect, R⁴ can be an optionally substituted organic residue comprising 1 to 4 carbons, including methyl, ethyl, propyl, and butyl.

In one aspect, 0-1 of the ten R⁴ groups are independently present as non-hydrogen substituents. In a further aspect, 0-2 of the ten R⁴ groups are independently present as non-hydrogen substituents. In a further aspect, 0-3 of the ten R⁴ groups are independently present as non-hydrogen substituents. In a further aspect, 0-4 of the ten R⁴ groups are independently present as non-hydrogen substituents. In a further aspect, 0-5 of the ten R⁴ groups are independently present as non-hydrogen substituents. In a further aspect, 1 of the ten R⁴ groups is present as a non-hydrogen substituent. In a further aspect, 1-2 of the ten R⁴ groups are independently present as non-hydrogen substituents. In a further aspect, 1-3 of the ten R⁴ groups are independently present as non-hydrogen substituents. In a further aspect, 1-4 of the ten $R^4$ substituents are independently present as non-hydrogen substituents. In a further aspect, 1-5 of $R^4$ are independently substituted with non-hydrogen substituents.

h. $R^5$ Groups

In one aspect, $R^5$ is an optionally substituted organic residue comprising from 1 to 6 carbons. For example, $R^5$ can be methyl, ethyl, propyl, butyl, pentyl, or hexyl. In a further aspect, $R^5$ can be an optionally substituted organic residue comprising 1 to 4 carbons, including methyl, ethyl, propyl, and butyl. In a further aspect, $R^5$ can be an optionally substituted organic residue comprising 1 to 2 carbons, including methyl, ethyl. In a further aspect, $R^5$ can be an optionally substituted organic residue comprising 2 to 4 carbons, including ethyl, propyl, and butyl. In a further aspect, $R^5$ can be an optionally substituted organic residue comprising 1 to 3 carbons, including methyl, ethyl, and propyl. In a further aspect, $R^5$ can be an optionally substituted organic residue comprising 2 carbons, including ethyl. In a further aspect, $R^5$ can be optionally substituted ethyl. In a further aspect, $R^5$ is ethyl. In a further aspect, $R^5$ is substituted with 0-3 groups selected from fluoro, chloro, bromo, hydroxyl, alkoxyl, nitrile, nitro, thiol, and optionally substituted amino.

In a further aspect, $R^5$ is an optionally substituted cyclic organic residue selected from aryl, heteroaryl, cycloalkyl, heterocycloalkyl, cycloalkenyl, and heterocycloalkenyl.

In a further aspect, $R^5$ is optionally substituted aryl.

In a further aspect, $R^5$ is optionally substituted heteroaryl selected from oxazolyl, isoxazolyl, pyrazolyl, furanyl, pyranyl, imidazolyl, thiophenyl, pyridinyl, pyridazinyl, pyrimidinyl; pyrazinyl, triazinyl, and tetrazinyl.

In a further aspect, $R^5$ is optionally substituted cycloalkyl selected from cyclopropyl, cyclobutyl, cyclopentyl, cyclohexyl, and bicyclo[3.1.0]hexyl.

In a further aspect, $R^5$ is optionally substituted heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^5$ is optionally substituted cycloalkenyl selected from cyclobutenyl, cyclopentenyl, cyclopentadienyl, cyclohexenyl, and cyclohexadienyl.

In a further aspect, $R^5$ is optionally substituted heterocycloalkenyl comprising pyrazolinone, imidazolinone, or a mono-, di- or tri-unsaturated analog of a heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

i. $R^8$ Groups

In one aspect, $R^8$ is hydrogen, a hydrolysable residue, or an optionally substituted organic residue comprising 1 to 6 carbons. In a further aspect, $R^8$ is hydrogen. In a further aspect, $R^8$ is a hydrolysable residue, for example, a protecting group (e.g., a butuloxycarbonyl group or a silyl protecting group). In a further aspect, $R^8$ is an optionally substituted organic residue comprising 1 to 6 carbons, including methyl, ethyl, propyl, butyl, pentyl, and hexyl. In a further aspect, $R^8$ can be an optionally substituted organic residue comprising 1 to 4 carbons, including methyl, ethyl, propyl, and butyl.

j. Example Compounds

In one aspect, a compound can be present as:

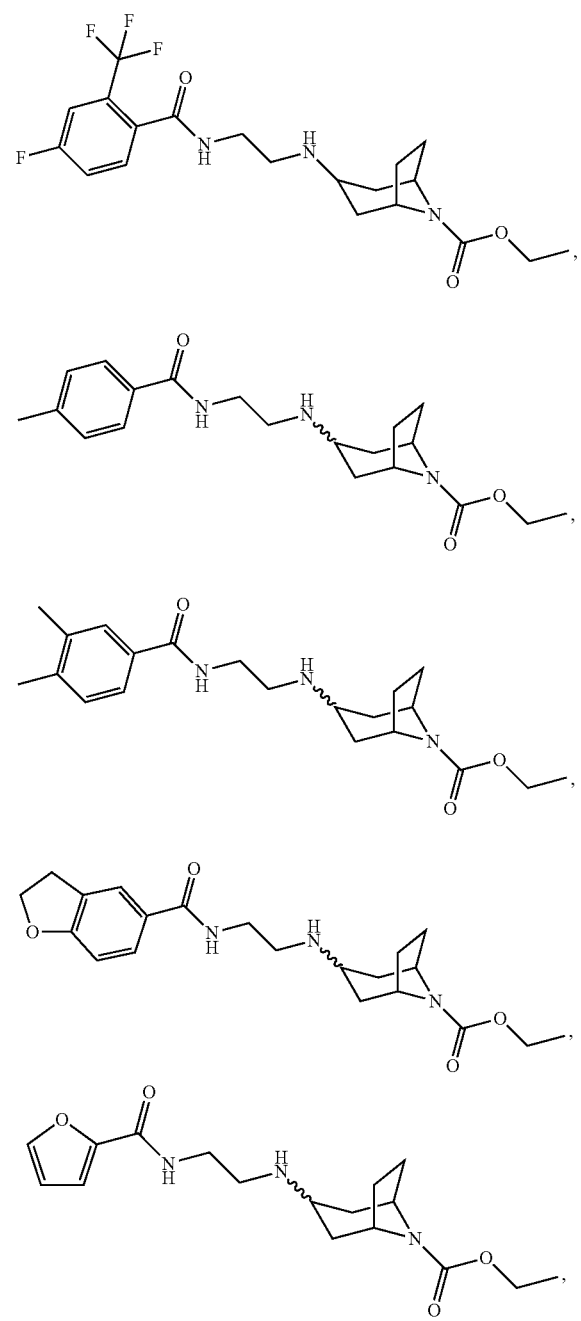

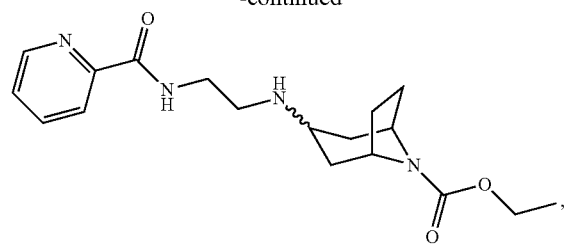
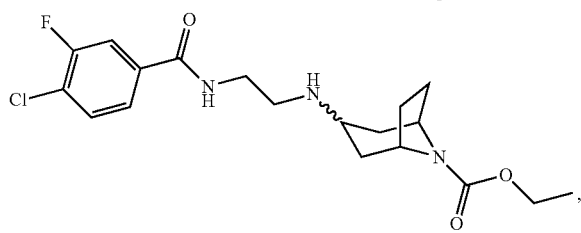
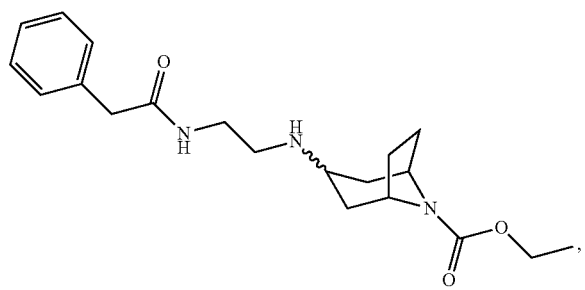
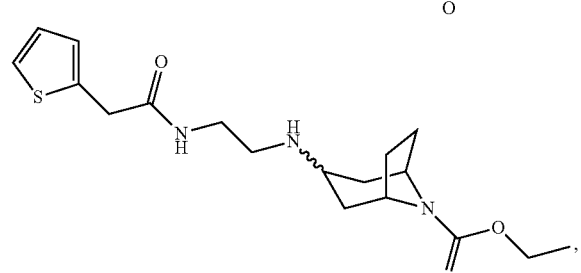
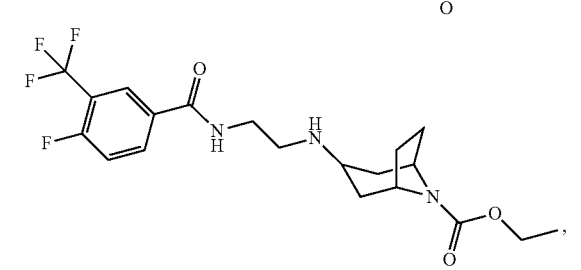
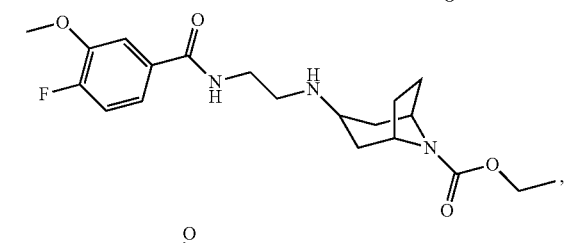
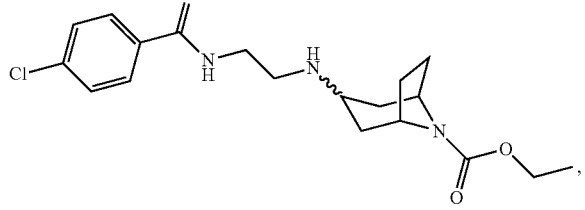
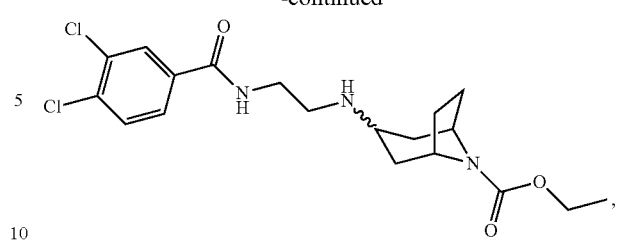
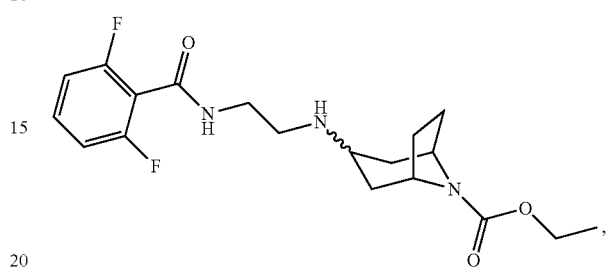
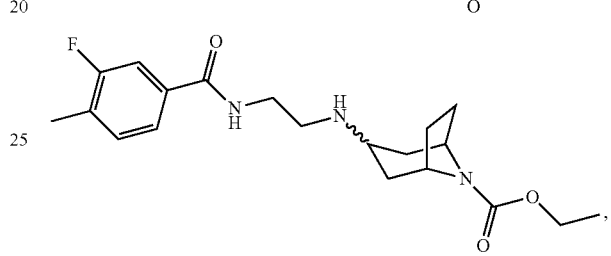
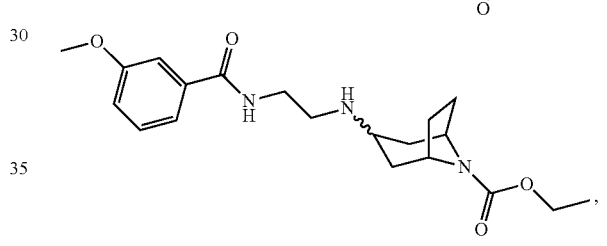
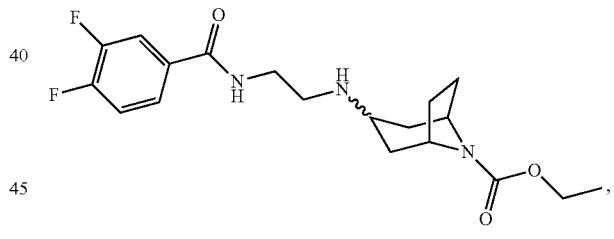
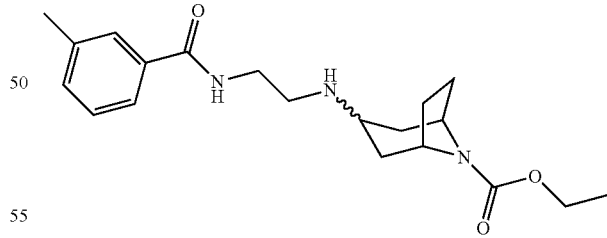
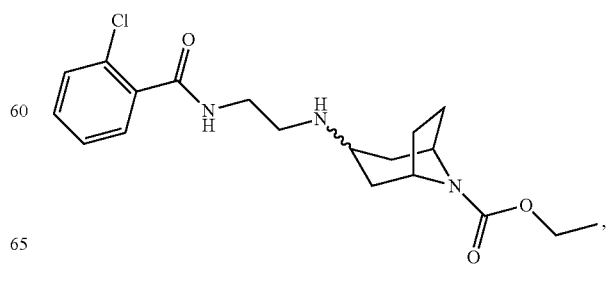

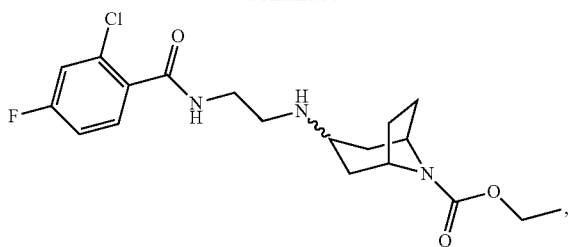
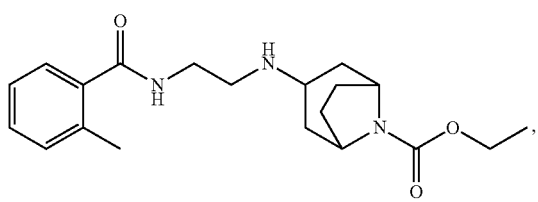
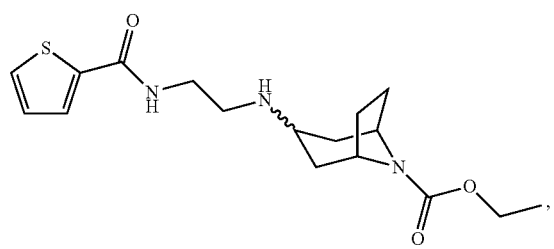
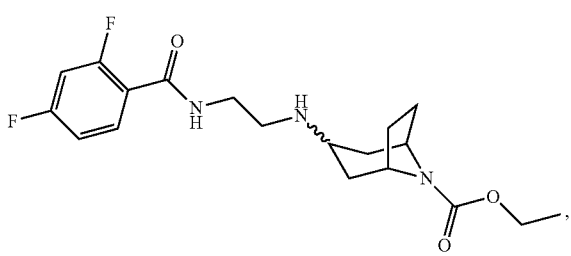
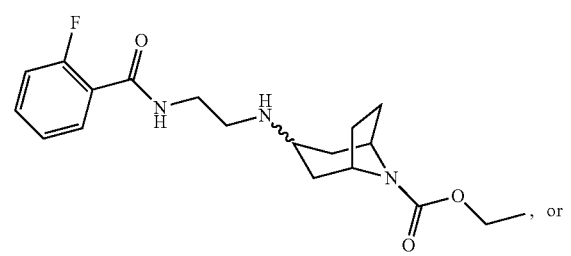
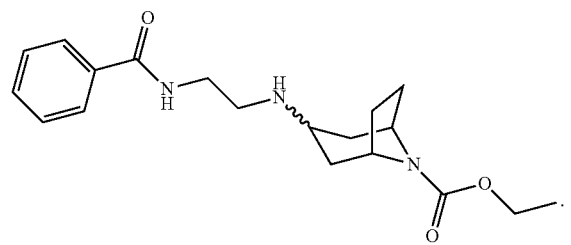
In a further aspect, a compound can be present as:
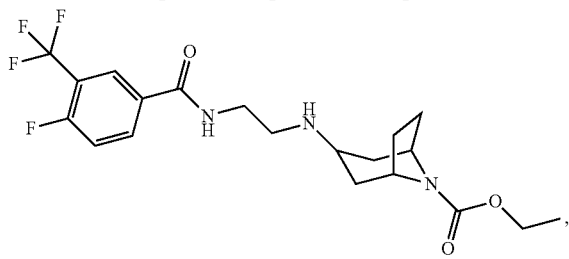
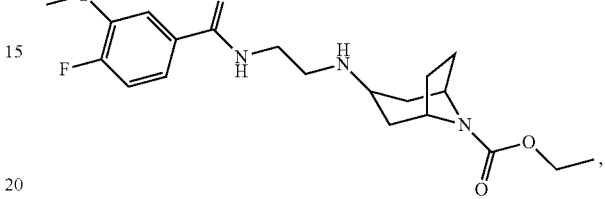
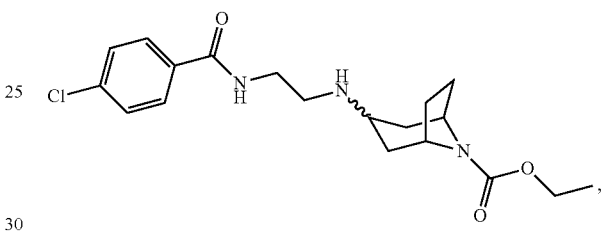
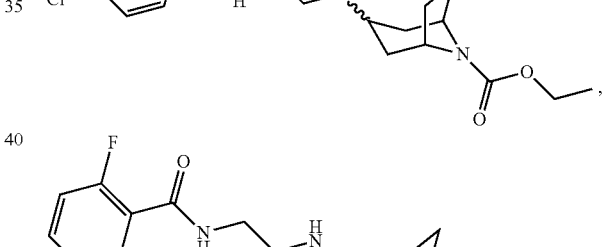
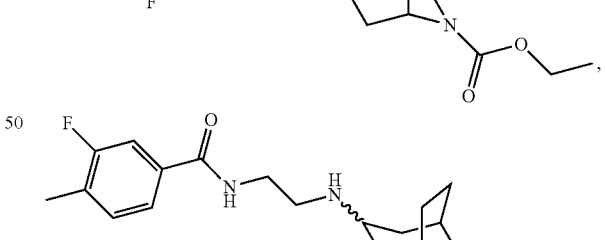
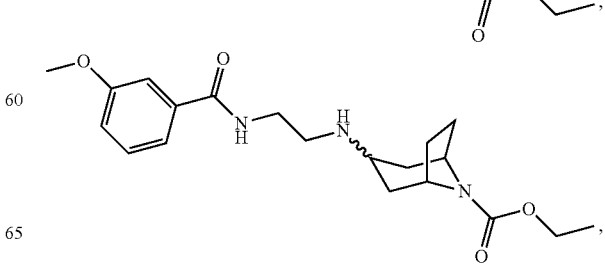

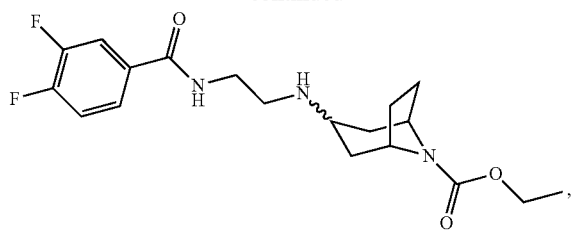
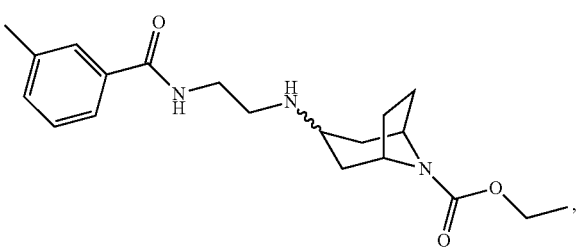
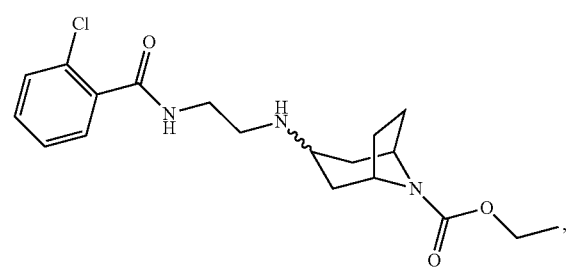
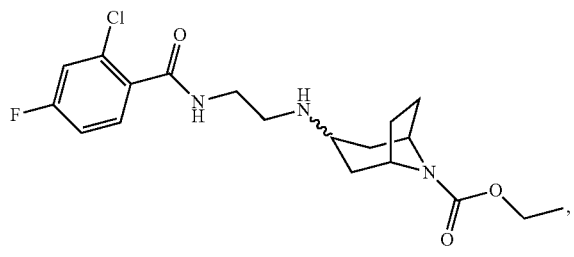
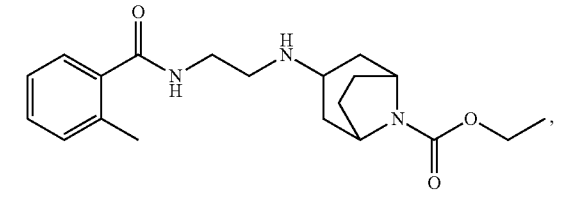
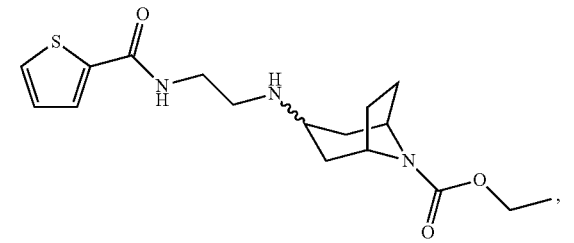
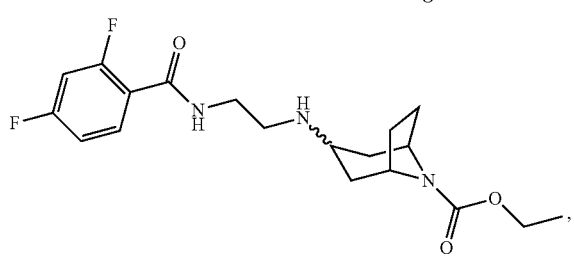
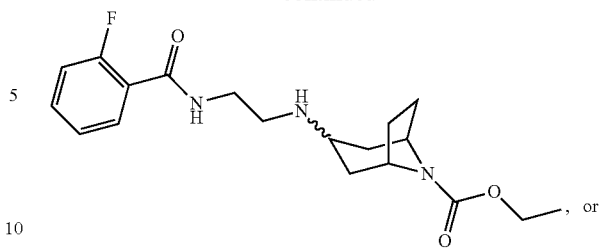
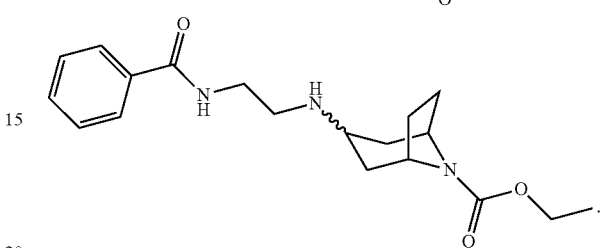
In a further aspect, a compound can be present as:
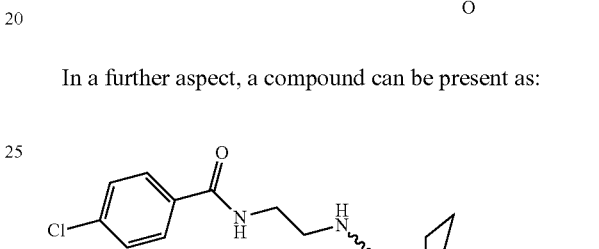
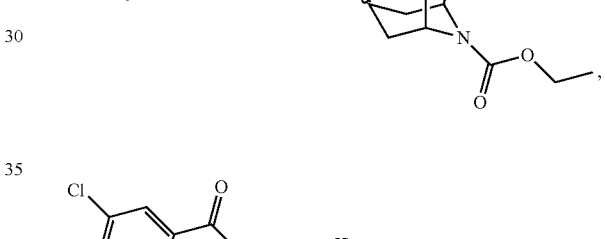
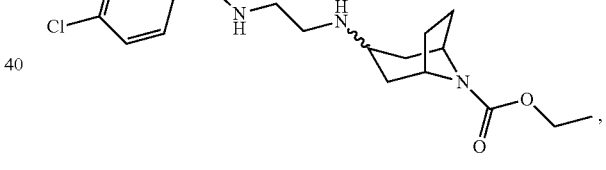
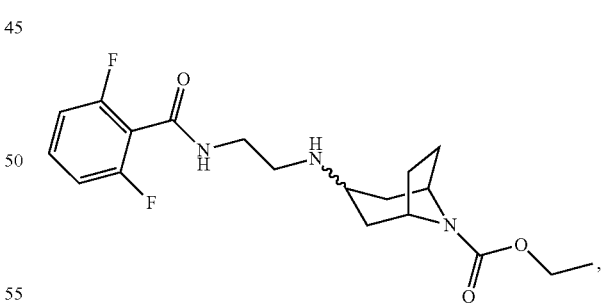
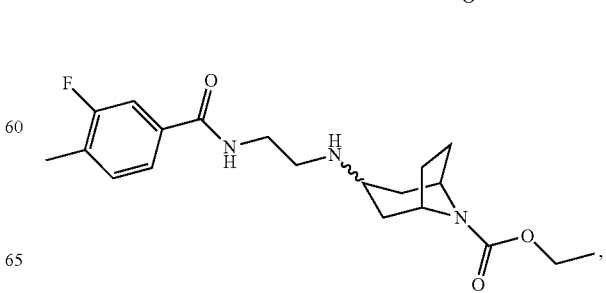

-continued
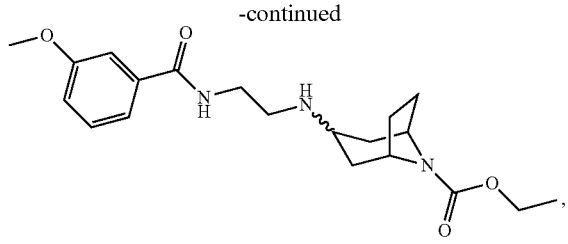
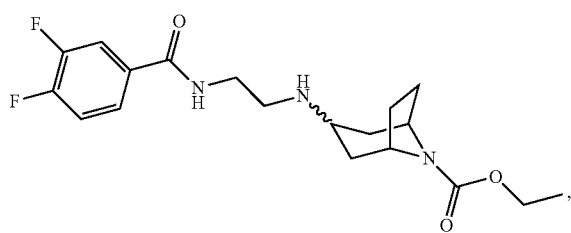
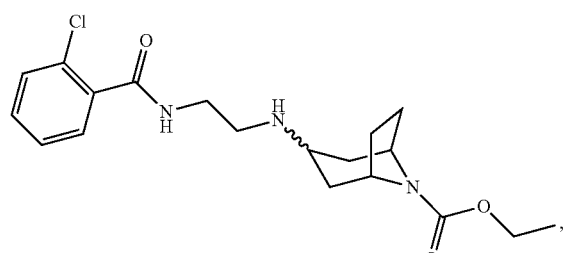
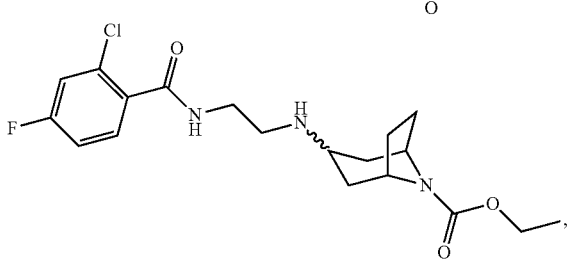
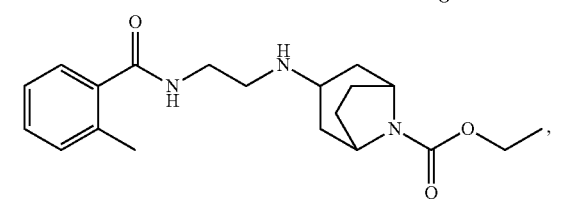
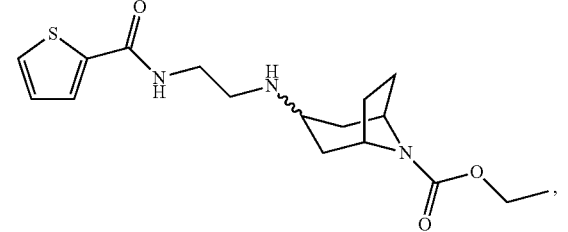
-continued
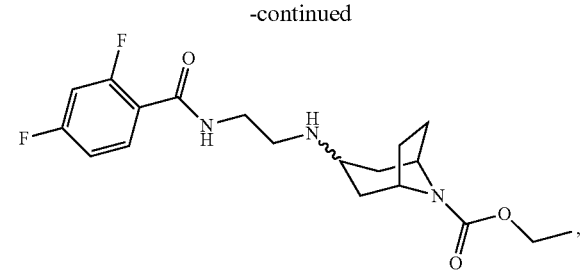
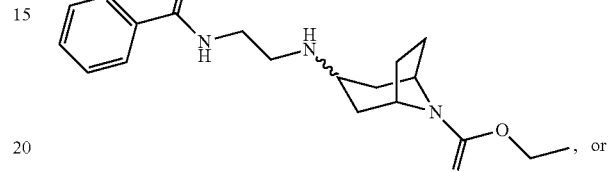,  or
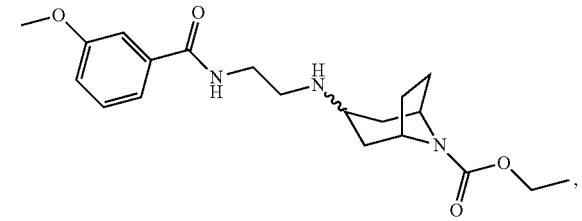.
In a further aspect, a compound can be present as:
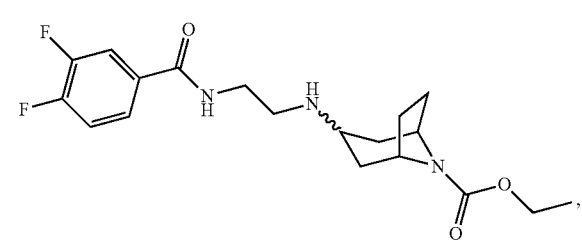
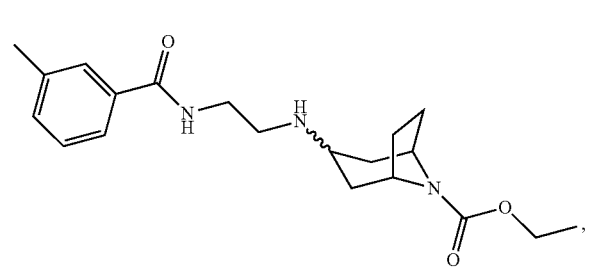

-continued
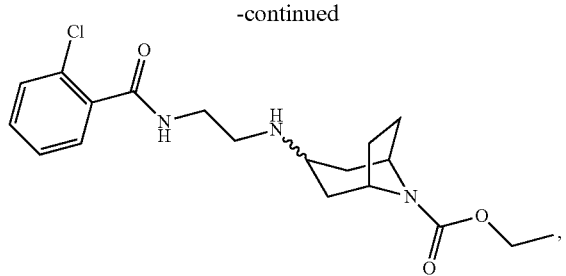
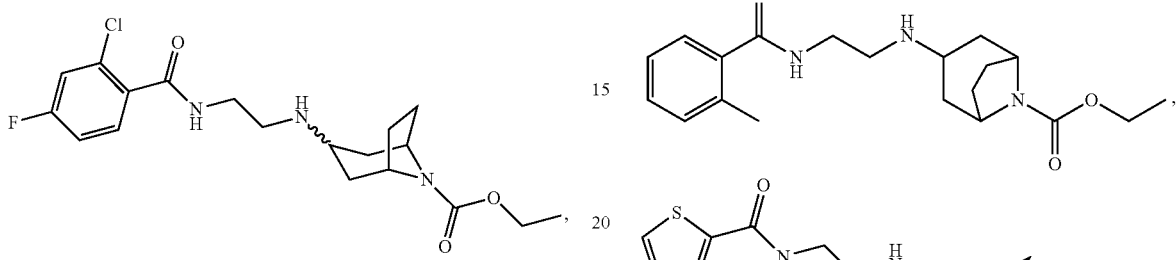
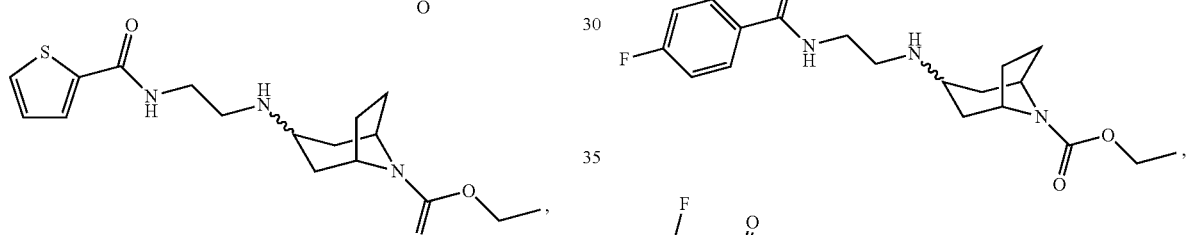
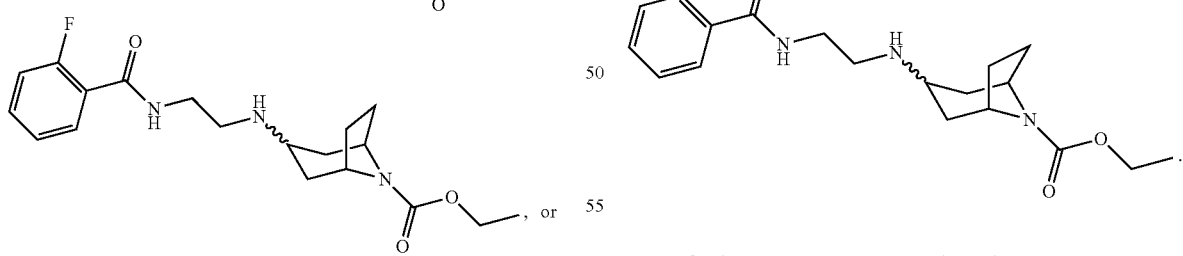
In a further aspect, a compound can be present as:
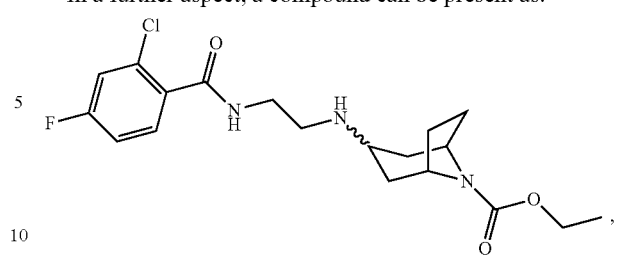
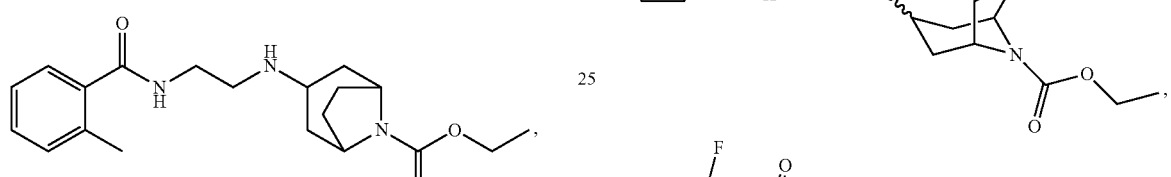
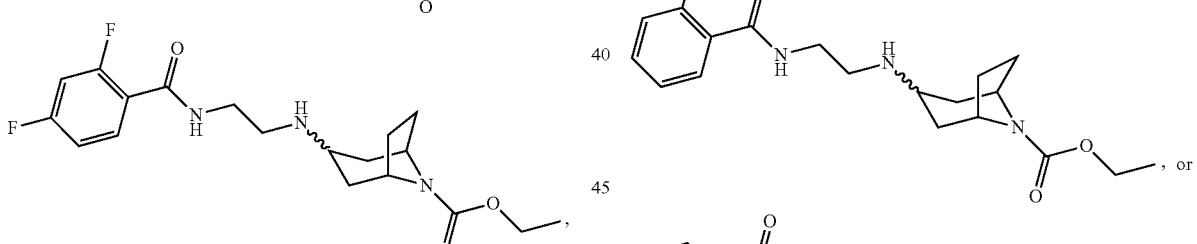
In a further aspect, a compound can be present as:
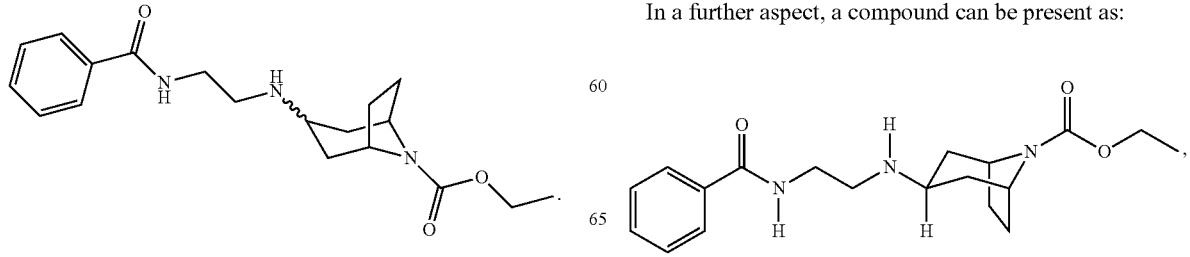

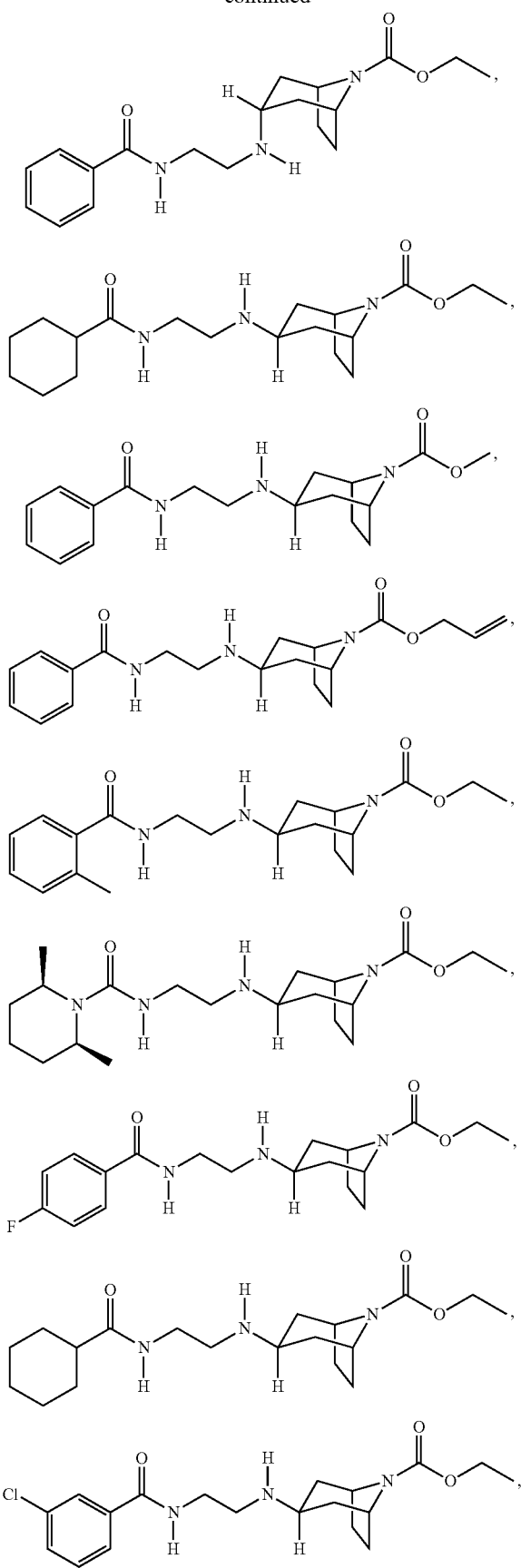
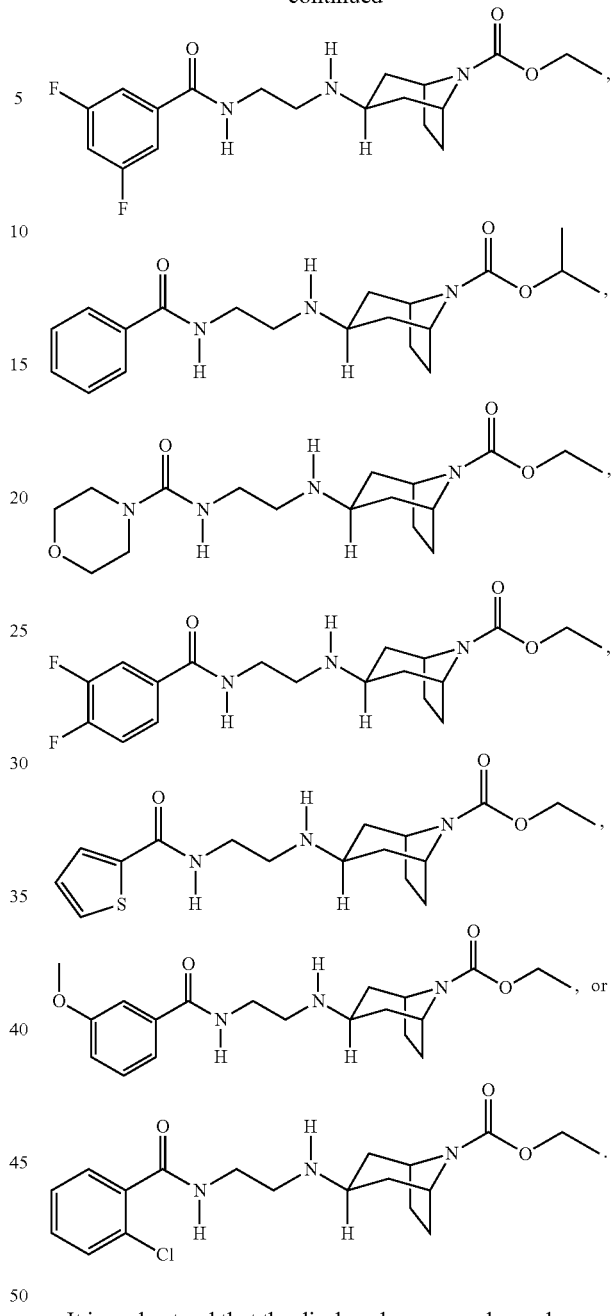

It is understood that the disclosed compounds can be used in connection with the disclosed methods, compositions, kits, and uses.

The pharmaceutical acceptable derivatives of the compounds can include any suitable derivative, such as pharmaceutically acceptable salts as discussed below, isomers, radiolabeled analogs, radioisotopic analogs, tautomers, and the like.

2. $M_1$ Activity and Selectivity

In one aspect, the compound activates $M_1$ response in $M_1$-transfected CHO-K1 cells. For example, the compound can have an $EC_{50}$ of less than about 10 µM, of less than about 5 µM, of less than about 1 µM, of less than about 500 nM, of less than about 100 nM, or of less than about 50 nM.

In various further aspects, the compound activates $M_1$ response in $M_1$-transfected CHO-K1 cells with an $EC_{50}$ less than the $EC_{50}$ for one or more of $M_2$-$M_5$. That is, a disclosed compound can have selectivity for the $M_1$ receptor vis-à-vis one or more of the $M_2$-$M_5$ receptors. For example, in one aspect, a disclosed compound can activate $M_1$ response with an $EC_{50}$ of 5-fold less than that for $M_2$, of 10-fold less than that for $M_2$, of 20-fold less than that for $M_2$, of 30-fold less than that for $M_2$, or of 50-fold less than that for $M_2$. In a further aspect, a disclosed compound can activate $M_1$ response with an $EC_{50}$ of 5-fold less than that for $M_3$, of 10-fold less than that for $M_3$, of 20-fold less than that for $M_3$, of 30-fold less than that for $M_3$, or of 50-fold less than that for $M_3$. In a further aspect, a disclosed compound can activate $M_1$ response with an $EC_{50}$ of 5-fold less than that for $M_4$, of 10-fold less than that for $M_4$, of 20-fold less than that for $M_4$, of 30-fold less than that for $M_4$, or of 50-fold less than that for $M_4$. In a further aspect, a disclosed compound can activate $M_1$ response with an $EC_{50}$ of 5-fold less than that for $M_5$, of 10-fold less than that for $M_5$, of 20-fold less than that for $M_5$, of 30-fold less than that for $M_5$, or of 50-fold less than that for $M_5$. In a further aspect, a disclosed compound can activate $M_1$ response with an $EC_{50}$ of 5-fold less than that for the $M_2$-$M_5$ receptors, of 10-fold less than that for the $M_2$-$M_5$ receptors, of 20-fold less than that for the $M_2$-$M_5$ receptors, of 30-fold less than that for the $M_2$-$M_5$ receptors, or of 50-fold less than that for the $M_2$-$M_5$ receptors.

In various further aspects, the compound activates $M_1$ response in $M_1$-transfected CHO-K1 cells with an $EC_{50}$ of less than about 10 μM and exhibits a selectivity for the $M_1$ receptor vis-à-vis one or more of the $M_2$-$M_5$ receptors. For example, in one aspect, the compound can have an $EC_{50}$ of less than about 10 μM, of less than about 5 μM, of less than about 1 μM, of less than about 500 nM, of less than about 100 nM, or of less than about 50 nM; and the compound can also activate $M_1$ response with an $EC_{50}$ of 5-fold less than that for $M_2$, of 10-fold less than that for $M_2$, of 20-fold less than that for $M_2$, of 30-fold less than that for $M_2$, or of 50-fold less than that for $M_2$. In a further aspect, the compound can have an $EC_{50}$ of less than about 10 μM, of less than about 5 μM, of less than about 1 μM, of less than about 500 nM, of less than about 100 nM, or of less than about 50 nM; and the compound can also activate $M_1$ response with an $EC_{50}$ of 5-fold less than that for $M_3$, of 10-fold less than that for $M_3$, of 20-fold less than that for $M_3$, of 30-fold less than that for $M_3$, or of 50-fold less than that for $M_3$. In a further aspect, the compound can have an $EC_{50}$ of less than about 10 μM, of less than about 5 μM, of less than about 1 μM, of less than about 500 nM, of less than about 100 nM, or of less than about 50 nM; and the compound can also activate $M_1$ response with an $EC_{50}$ of 5-fold less than that for $M_4$, of 10-fold less than that for $M_4$, of 20-fold less than that for $M_4$, of 30-fold less than that for $M_4$, or of 50-fold less than that for $M_4$. In a further aspect, the compound can have an $EC_{50}$ of less than about 10 μM, of less than about 5 μM, of less than about 1 μM, of less than about 500 nM, of less than about 100 nM, or of less than about 50 nM; and the compound can also activate $M_1$ response with an $EC_{50}$ of 5-fold less than that for $M_5$, of 10-fold less than that for $M_5$, of 20-fold less than that for $M_5$, of 30-fold less than that for $M_5$, or of 50-fold less than that for $M_5$. In a further aspect, the compound can have an $EC_{50}$ of less than about 10 μM, of less than about 5 μM, of less than about 1 μM, of less than about 500 nM, of less than about 100 nM, or of less than about 50 nM; and the compound can also activate $M_1$ response with an $EC_{50}$ of 5-fold less than that for the $M_2$-$M_5$ receptors, of 10-fold less than that for the $M_2$-$M_5$ receptors, of 20-fold less than that for the $M_2$-$M_5$ receptors, of 30-fold less than that for the $M_2$-$M_5$ receptors, or of 50-fold less than that for the $M_2$-$M_5$ receptors.

FIGS. 1.0-1.5 and 2.0-2.5 illustrate the selectivity for the $hM_1$ receptor of various disclosed compounds (e.g., ethyl 3-((3-exo)-(2-benzamidoethyl)amino)-8-azabicyclo[3.2.1]octane-8-carboxylate (see Example 26) and ethyl 3-((3-endo)-(2-benzamidoethyl)amino)-8-azabicyclo[3.2.1]octane-8-carboxylate (see Example 27)) vis-à-vis $hM_2$-$hM_5$ receptors. Kinetic data and dose response data for these compounds indicate selectivity for the $hM_1$ receptor.

It is also contemplated that the disclosed methods, uses, compositions, and kits can be employed in connection with one or more compounds having selectivities disclosed above.

C. METHODS OF MAKING THE COMPOUNDS

In one aspect, the invention relates to methods of making compounds useful as selective activators of the $M_1$ receptor, which can be useful in the treatment of disorders associated with $M_1$ receptor activity.

The compounds of this invention can be prepared by employing reactions as shown in the disclosed schemes, in addition to other standard manipulations that are known in the literature, exemplified in the experimental sections or clear to one skilled in the art. For clarity, examples having fewer substituents can be shown where multiple substituents are allowed under the definitions disclosed herein.

An exemplary synthetic route is shown in Scheme 1 below:

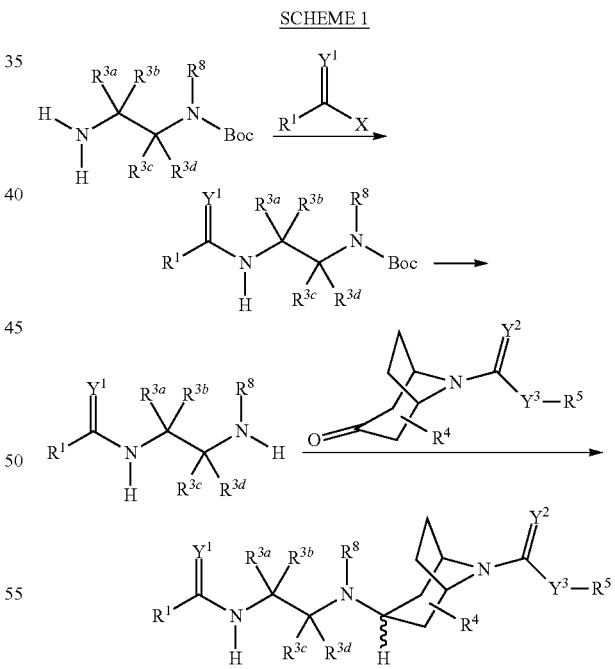

Generally, the disclosed methods can comprise one or both of two chemical transformations. One transformation involves a reductive amination reaction between an amine functionality and carbonyl functionality, as represented in Scheme 2 below:

SCHEME 2

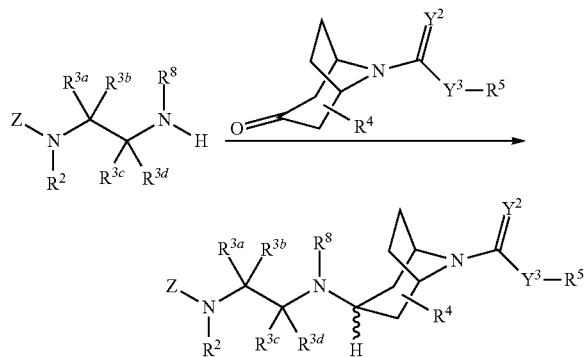

The product of this reaction can, thus, be an amine, which can be isolated or carried into another chemical transformation in unisolated form. In one aspect, Z can be a protecting group, which can be removed subsequent to this reaction as well as before, or concurrently with, further reaction. Both the starting amino compound and the carbonyl compound can be prepared or obtained commercially. Reductive amination reactions, and reagents therefor, are well known to those of skill in the art. Many of such reagents and reaction conditions are described by Richard C. Larock, COMPREHENSIVE ORGANIC TRANSFORMATIONS: A GUIDE TO FUNCTIONAL GROUP PREPARATIONS, 1999 John Wiley & Sons, Inc. It is contemplated that alternate reaction conditions can be employed.

The other transformation involves a reaction between the deprotected amine functionality and an activated carboxyl functionality (e.g., an acid halide), yielding an amide, as represented in Scheme 3 below:

SCHEME 3

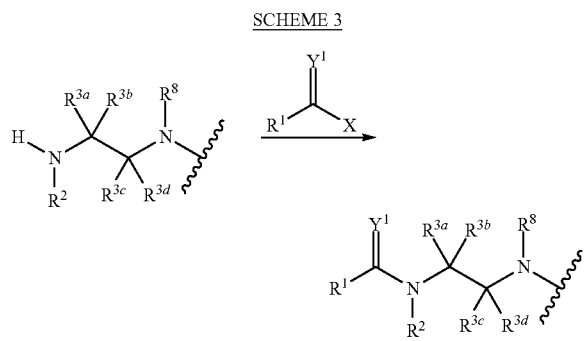

The product of this reaction can, thus, be an amide, which can be isolated or carried into another chemical transformation in unisolated form. In one aspect, the compound can further comprise a protecting group, which can be removed subsequent to this reaction as well as before, or concurrently with, further reaction. Both the starting amino compound and the activated carboxyl compound can be prepared or obtained commercially. Amidation reactions, and reagents therefor, are well known to those of skill in the art. Many of such reagents and reaction conditions are described by Richard C. Larock, COMPREHENSIVE ORGANIC TRANSFORMATIONS: A GUIDE TO FUNCTIONAL GROUP PREPARATIONS, 1999 John Wiley & Sons, Inc. It is contemplated that alternate reaction conditions can be employed.

A specific synthetic example is illustrated in Scheme 4 below:

SCHEME 4

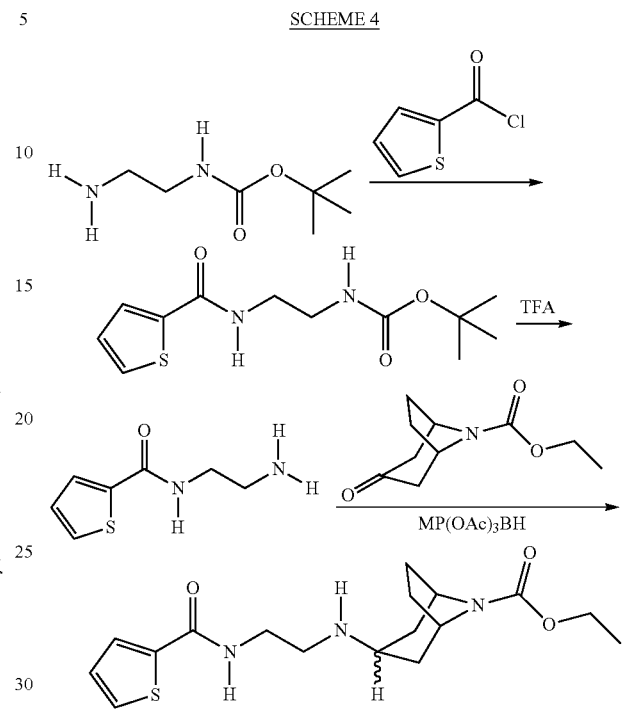

To prepare the amide, tert-butyl 2-aminoethylcarbamate and thiophene-2-carbonyl chloride were mixed in dichloromethane and then treated with PS-DIEA resin. Subsequently, the slurry was treated with MP-Isocyanate resin and PS-Trisamine resin. The intermediate was then treated with trifluoroacetic acid to effect deprotection. After concentration, the free amine was reacted with ethyl 3-oxo-8-azabicyclo[3.2.1]octane-8-carboxylate and reducing agent (e.g., MP(OAc)$_3$BH) to provide ethyl 3-(2-(thiophene-2-carboxamido)ethylamino)-8-azabicyclo[3.2.1]octane-8-carboxylate as the TFA salt. See also, Example 1, supra.

In this specific example, the endo product is produced as the major product in preference to the exo product, which is produced as a minor product, if at all. Without wishing to be bound by theory, it is believed that this specificity during the reduction reaction is due to steric hinderance at the intermediate imine functionality.

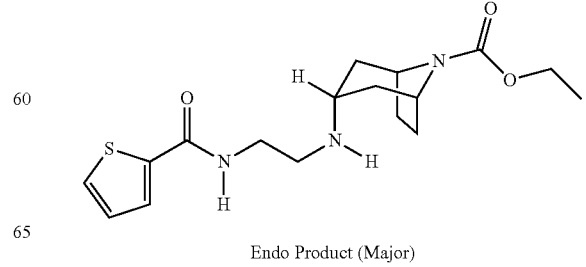

Endo Product (Major)

-continued

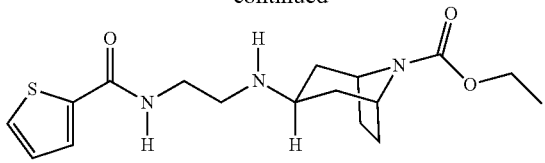

Exo Product (Minor)

Thus, in one aspect, the invention relates to methods for preparing a compound comprising the steps of: a. providing an amino compound having a structure represented by a formula:

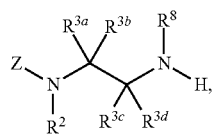

wherein $R^{3a}$, $R^{3b}$, $R^{3c}$, and $R^{3d}$ independently comprise hydrogen or optionally substituted organic residue comprising from 1 to 6 carbons; wherein $R^8$ is hydrogen, a hydrolysable residue, or an optionally substituted organic residue comprising 1 to 6 carbons; wherein $R^2$ is hydrogen, a hydrolysable residue, or an optionally substituted organic residue comprising 1 to 6 carbons; and wherein Z is hydrogen, a protecting group, or a group having a structure represented by a formula:

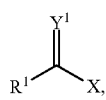

wherein $R^1$ is an optionally substituted organic residue comprising from 1 to 12 carbons, and b. reacting the amino compound with a carboxyl compound having a structure represented by a formula:

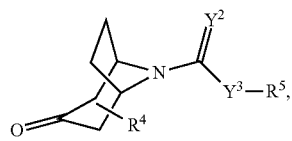

wherein $Y^2$ is O or S; wherein $Y^3$ is a covalent bond, O, S, or N—$R^6$; $R^4$ comprises ten substituents independently selected from hydrogen, halogen, hydroxyl, nitrile, nitro, thiol, optionally substituted amino, and optionally substituted organic residue comprising from 1 to 6 carbons; wherein $R^5$ is an optionally substituted organic residue comprising from 1 to 6 carbons; and wherein $R^6$, when present, is independently selected from hydrogen, a hydrolysable residue, and an optionally substituted organic residue comprising from 1 to 6 carbons. In a further aspect, reacting is through a reductive amination with solid-supported, borohydride-based reducing agents.

In a further aspect, Z is a protecting group, for example, a butyloxycarbonyl group. In a further aspect, Z is a group having a structure represented by a formula:

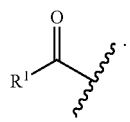

In a further aspect, Z is a group having a structure represented by a formula:

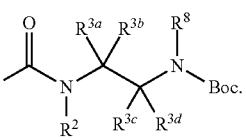

wherein n is 0 or 1; and wherein A is an optionally substituted cyclic organic residue selected from aryl, heteroaryl, cycloalkyl, heterocycloalkyl, cycloalkenyl, and heterocycloalkenyl.

In a further aspect, providing comprises deprotection of a compound having a structure represented by a formula:

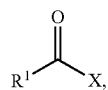

In one aspect, a method further comprises the step of reacting with a compound having a structure represented by a formula:

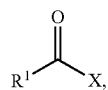

wherein X is a leaving group, for example, halide or pseudohalide.

In a further aspect, the compound has a structure represented by a formula:

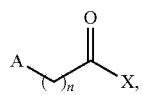

wherein n is 0 or 1; and wherein A is an optionally substituted cyclic organic residue selected from aryl, heteroaryl, cycloalkyl, heterocycloalkyl, cycloalkenyl, and heterocycloalkenyl.

In one aspect, the product has a structure represented by a formula:

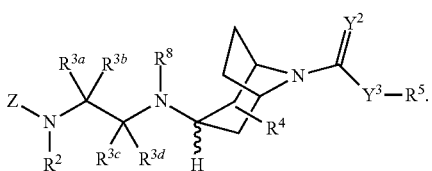

In a further aspect, the product has a structure represented by a formula:

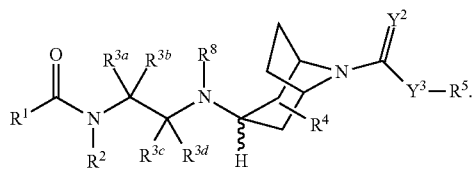

In a further aspect, the product has a structure represented by a formula:

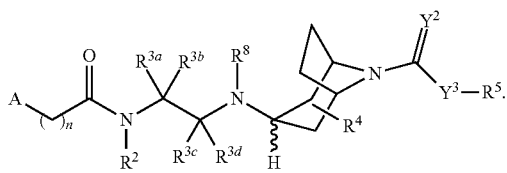

In a further aspect, the product has a structure represented by a formula:

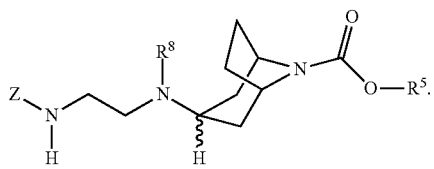

In a further aspect, the product has a structure represented by a formula:

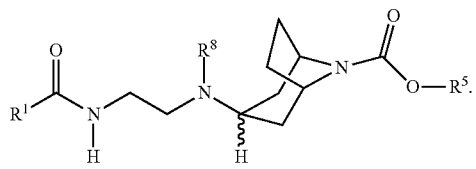

In a further aspect, the product has a structure represented by a formula:

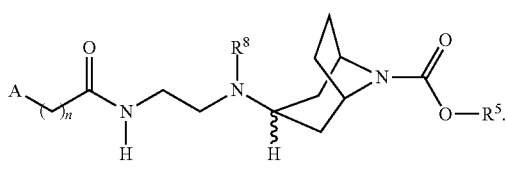

In certain aspects of the above-disclosed formulae, $R^8$ can be hydrogen.

In further aspects, the invention relates to endo/exo selective methods of making compounds useful as selective activators of the $M_1$ receptor. Again, the compounds of this invention can be prepared by employing reactions as shown in the disclosed schemes, in addition to other standard manipulations that are known in the literature, exemplified in the experimental sections or clear to one skilled in the art. For clarity, examples having fewer substituents can be shown where multiple substituents are allowed under the definitions disclosed herein.

An aldehyde intermediate can be readily prepared. A general synthetic route is shown in Scheme 5A below:

SCHEME 5A

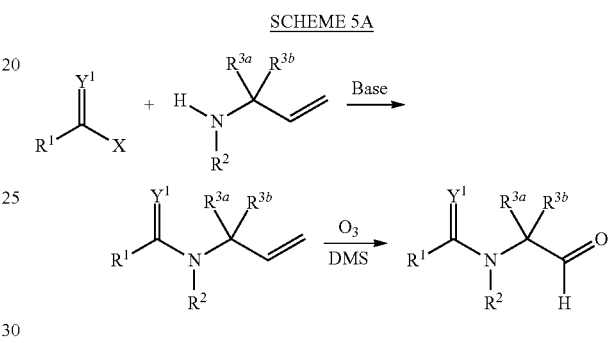

This route involves, inter alia, formation of an amide from reaction of an activated carbonyl compound with an allylic amine. Oxidation of the terminal vinyl group yields the aldehyde. It is contemplated that analogs to benzoyl chloride can be instead employed, thereby providing access to alternative substitution at $R^1$. Further, a specific synthetic example is illustrated in Scheme 5B below:

SCHEME 5B

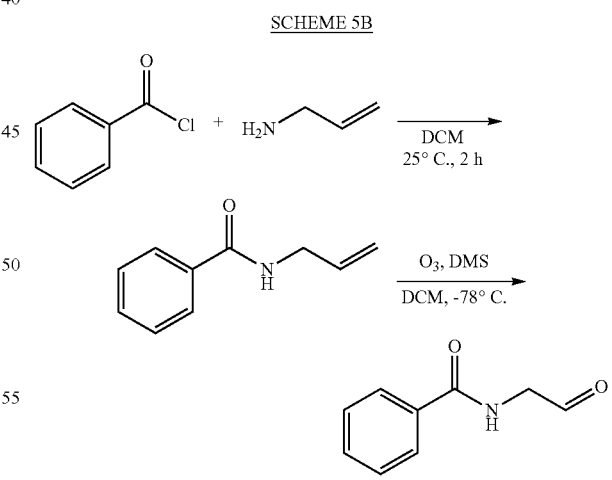

The product of this reaction sequence is, thus, an aldehyde. Benzoyl chloride reacts with allyl amine to form the corresponding amide, which is converted to the desired aldehyde by ozonolysis.

To gain access the exo-amine compounds, an amine intermediate can be readily prepared. A general synthetic route is shown in Scheme 6A below:

SCHEME 6A

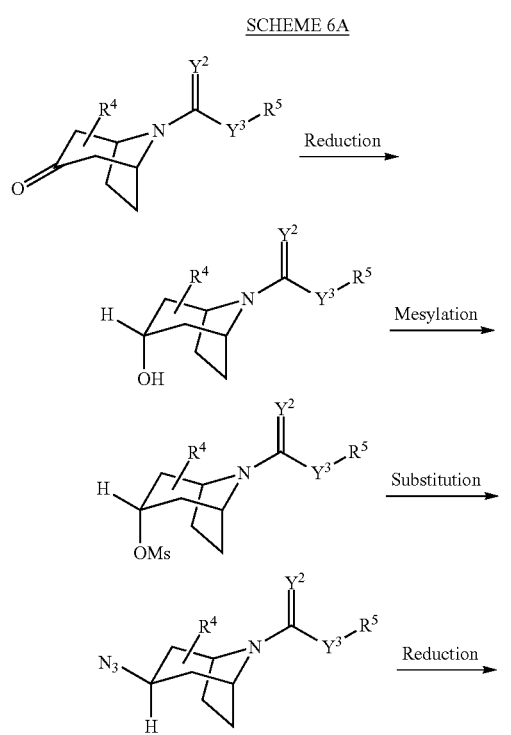

This route involves, inter alia, reduction to the favored endo-alcohol, followed by conversion of the resultant hydroxyl group into a leaving group. Displacement of the leaving group with azide, followed by reduction, provides the exo-amine. Further, a specific synthetic example is illustrated in Scheme 6B below:

SCHEME 6B

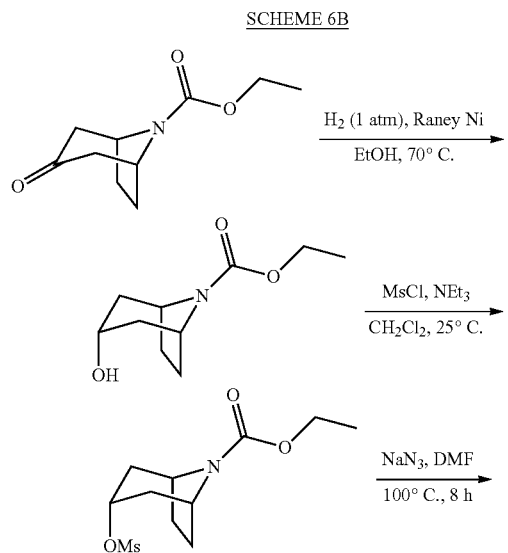

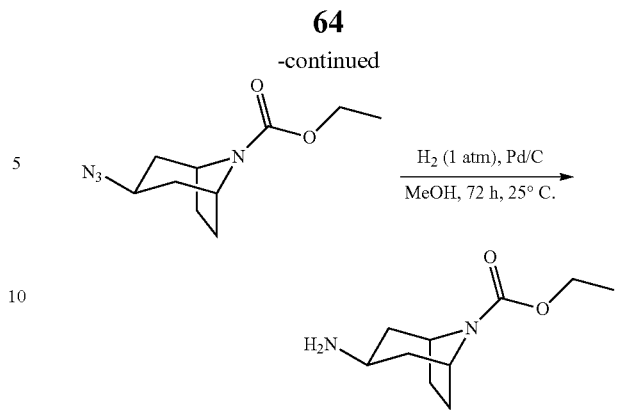

The product of this reaction sequence is, thus, the exo-amine. Ethyl 3-oxo-8-azabicyclo[3.2.1]octane-8-carboxylate can be hydrogenated from the favored carbonyl face to give the preferred endo-alcohol. Conversion to the mesylate and substitution with azide leads to inversion of configuration at that carbon. Reduction to the amine by hydrogenation provides the exo-amine.

The above amine can be used to generate the exo product by reductive amination. A general synthetic route is shown in Scheme 7A below:

SCHEME 7A

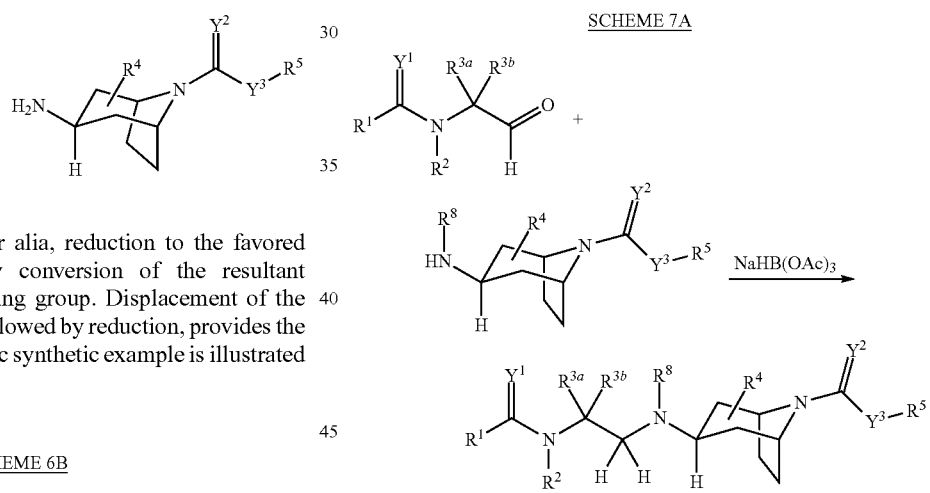

A specific synthetic example is illustrated in Scheme 7B below:

SCHEME 7B

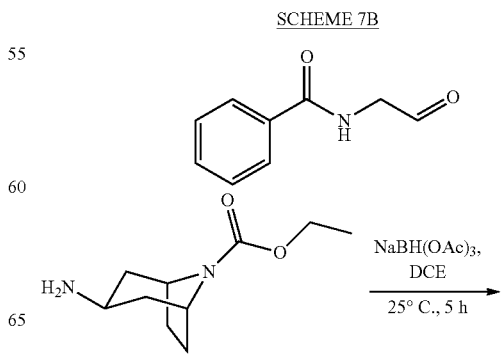

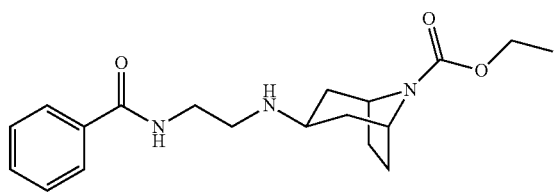

The product of this reaction sequence is, thus, an exo-amine. Reaction of the above amine (Schemes 6A-6B) with a selected aldehyde, prepared e.g. as shown in Schemes 5A-5B, in the presence of a suitable reduction agent (e.g., sodium triacetoxyborohydride), converts the intermediate imine to the desired exo-amine.

To gain access the endo-amine compounds, an amine intermediate can be readily prepared. A general synthetic route is shown in Scheme 8A below:

SCHEME 8A

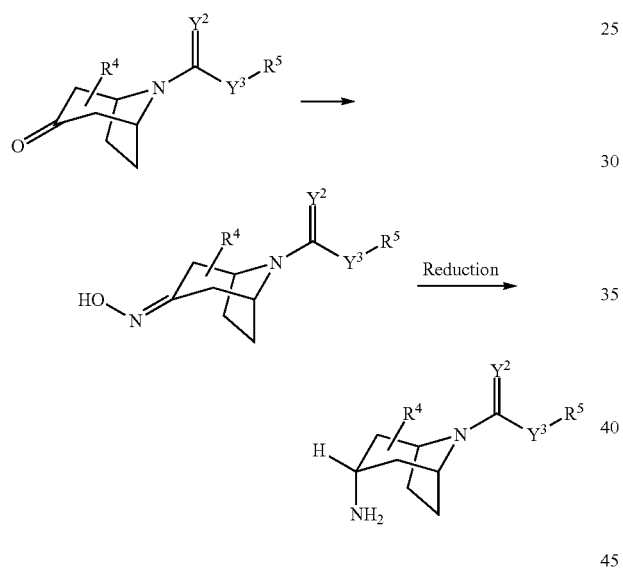

This route involves, inter alia, formation of the corresponding oxime, followed by reduction from the favored carbonyl face. Further, a specific synthetic example is illustrated in Scheme 8B below:

SCHEME 8B

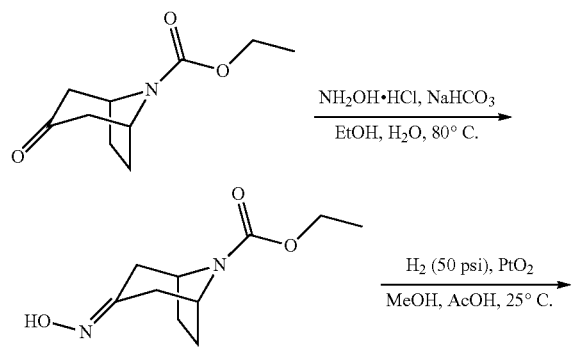

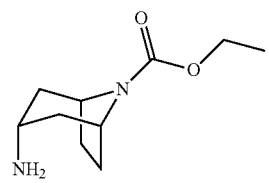

The product of this reaction sequence is, thus, the endo-amine. Ethyl 3-oxo-8-azabicyclo[3.2.1]octane-8-carboxylate readily transformed into ethyl 3-(hydroxyimino)-8-azabicyclo[3.2.1]octane-8-carboxylate. The oxime is then hydrogenated from the favored carbonyl face to give the endo-amine.

The above amine can be used to generate the endo product by reductive amination. A general synthetic route is shown in Scheme 9A below:

SCHEME 9A

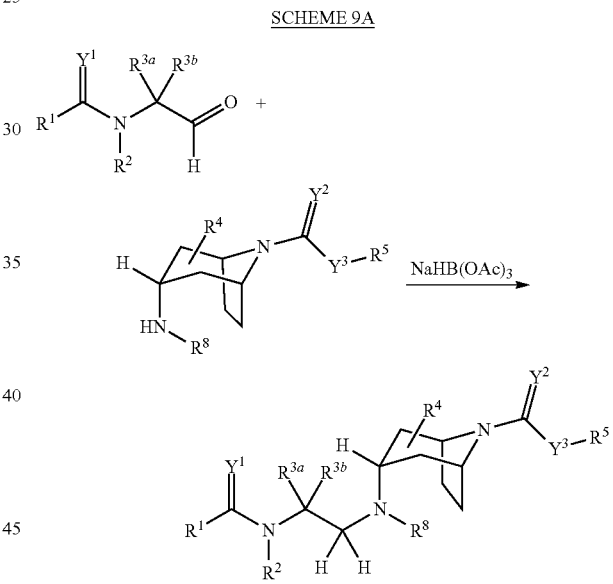

A specific synthetic example is illustrated in Scheme 9B below:

SCHEME 9B

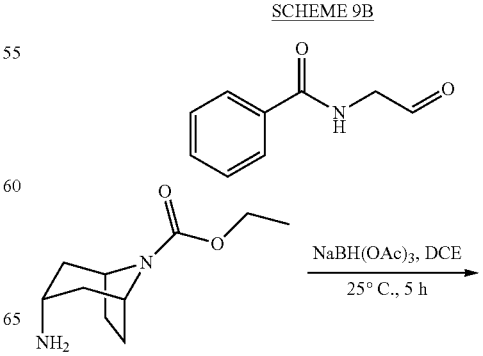

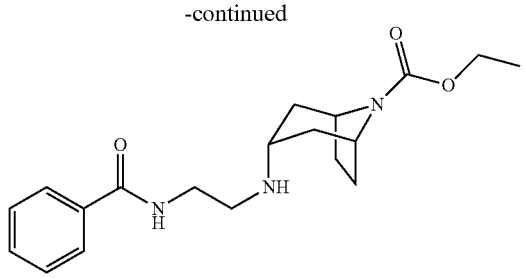

The product of this reaction sequence is, thus, an endo-amine. Reaction of the above amine (Schemes 8A-8B) with a selected aldehyde, prepared e.g. as shown in Schemes 5A-5B, in the presence of a suitable reduction agent (e.g., sodium triacetoxyborohydride), converts the intermediate imine to the desired endo amine.

The nitrogen of the azabicyclo[3.2.1]octane moiety can be further modified. A general synthetic route is shown in Scheme 10A below:

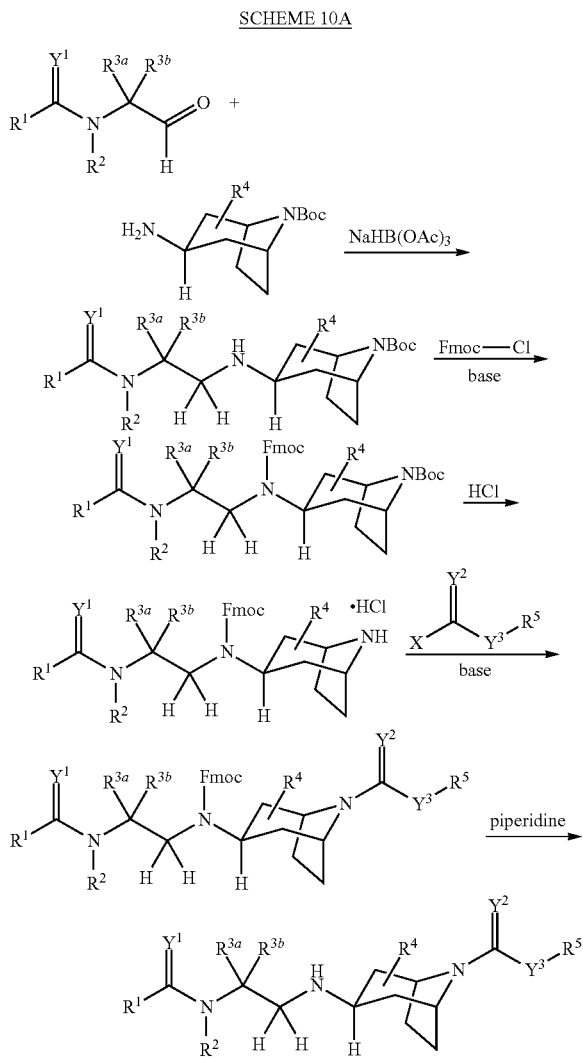

This route involves, inter alia, reductive amination as described above. The resultant amine can then be blocked with a protecting group (e.g., fluorenylmethyloxycarbonyl), which can be removed by chemical reactions orthogonal to those used to remove the protecting group (e.g., butyloxycarbonyl) at the azabicyclo[3.2.1]octane nitrogen. The azabicyclo[3.2.1]octane nitrogen of this doubly protected compound can be then selectively deprotected, and the resultant amine can be reacted with an activated carbonyl compound to form an amide, urea, or urethane. Deprotection of the ethanediamine moiety nitrogen can then be performed to liberate the desired compound. The product of this reaction sequence is, thus, an amide, urea, or urethane at the nitrogen of the azabicyclo[3.2.1]octane moiety.

Further, a specific synthetic example is illustrated in Scheme 10B below:

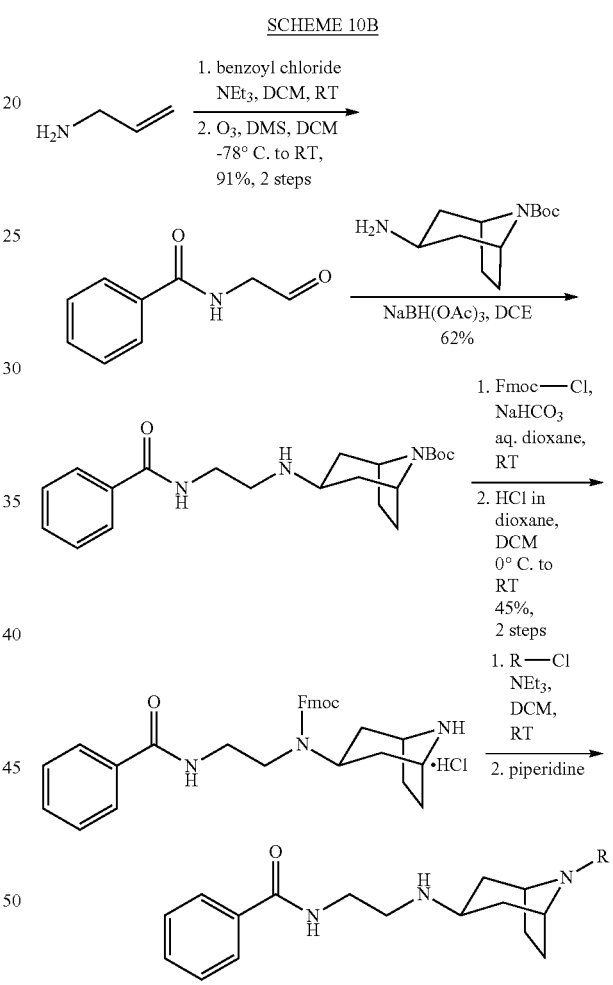

Moreover, the nitrogen of the ethanediamine moiety can be further modified. A general synthetic route is shown in Scheme 10A below:

SCHEME 11A

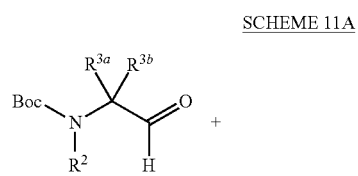

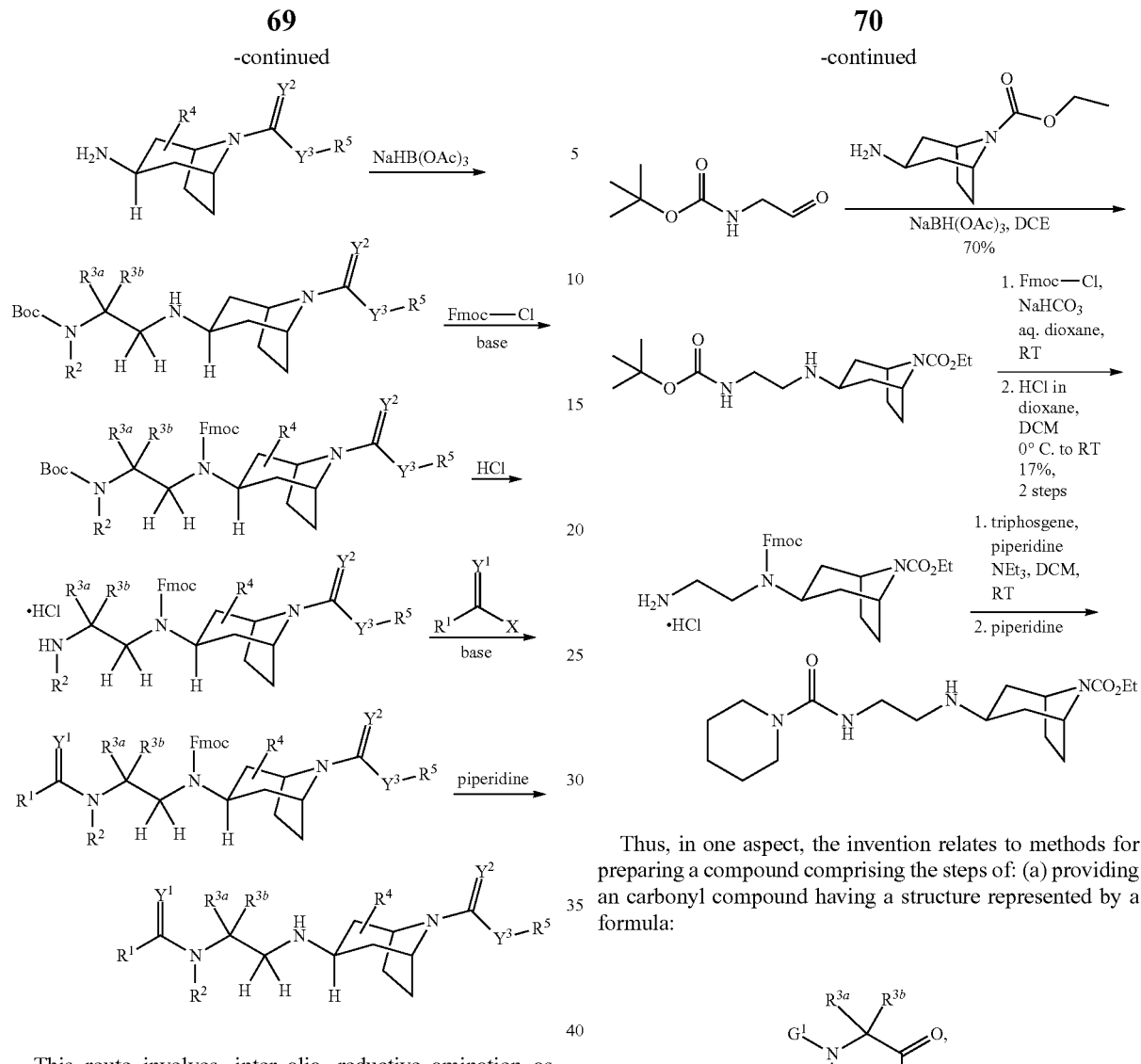

This route involves, inter alia, reductive amination as described above. The resultant amine can then be blocked with a protecting group (e.g., fluorenylmethyloxycarbonyl), which can be removed by chemical reactions orthogonal to those used to remove the protecting group (e.g., butyloxycarbonyl) at ethanediamine moiety nitrogen. The distal nitrogen of this doubly protected compound can be then selectively deprotected, and the resultant amine can be reacted with an activated carbonyl compound to form an amide, urea, or urethane. Deprotection of the ethanediamine moiety nitrogen can then be performed to liberate the desired compound. The product of this reaction sequence is, thus, an amide, urea, or urethane at the nitrogen of the ethanediamine moiety.

Further, a specific synthetic example is illustrated in Scheme 10B below:

SCHEME 11B

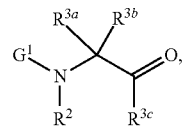

Thus, in one aspect, the invention relates to methods for preparing a compound comprising the steps of: (a) providing an carbonyl compound having a structure represented by a formula:

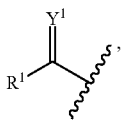

wherein $R^2$ is hydrogen, a hydrolysable residue, or an optionally substituted organic residue comprising 1 to 6 carbons; wherein $R^{3a}$, $R^{3b}$ and $R^{3c}$ comprise four substituents independently selected from hydrogen, or an optionally substituted organic residue comprising from 1 to 6 carbons; and wherein $G^1$ is a protecting group or a moiety having a structure represented by a formula:

wherein $Y^1$ is O or S; and wherein $R^1$ is an optionally substituted organic residue comprising from 1 to 12 carbons, (b) providing an amino compound having a structure represented by a formula:

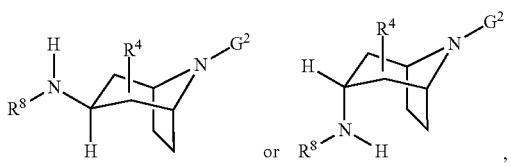

wherein R⁴ comprises ten substituents independently selected from hydrogen, halogen, hydroxyl, nitrile, nitro, thiol, optionally substituted amino, and optionally substituted organic residue comprising from 1 to 6 carbons; wherein R⁸ is hydrogen, a hydrolysable residue, or an optionally substituted organic residue comprising 1 to 6 carbons; and wherein G² is a protecting group orthogonal to G1 or G2 is a moiety having a structure represented by a formula:

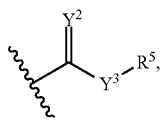

wherein Y² is O or S; wherein Y³ is a covalent bond, O, S, or N—R⁶; and wherein R⁵ is an optionally substituted organic residue comprising from 1 to 6 carbons, (c) reacting the amino compound with the carbonyl compound under reductive amination conditions to provide a compound having a structure represented by a formula:

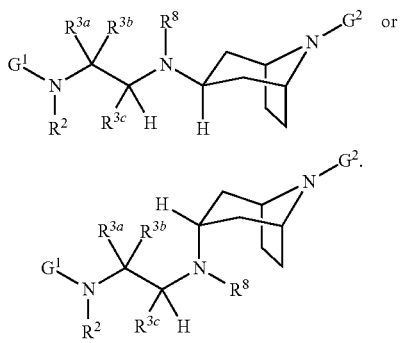

In a further aspect, providing the carbonyl compound comprises ozonolysis of a compound having a structure represented by a formula:

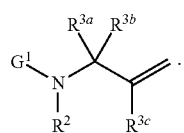

In a further aspect, providing the amino compound comprises the steps of: (a) reduction of a compound having a structure represented by a formula:

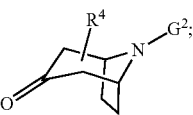

(b) conversion of the resulting hydroxyl group into a leaving group; (c) displacement of the leaving group with azide; and (d) reduction of the azide to form a compound having a structure represented by a formula:

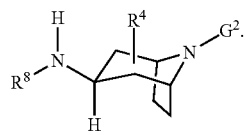

In a further aspect, providing the amino compound comprises the steps of: (a) reaction of a compound having a structure represented by a formula:

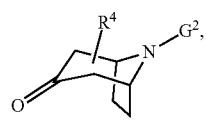

to form an oxime; and (b) reduction of the oxime to form a compound having a structure represented by a formula:

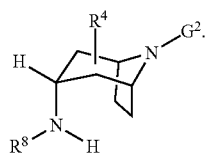

In a further aspect, the method further comprises the step of selectively deprotecting G¹ or G². In a yet further aspect, the method further comprises the step of reacting with a compound having a structure represented by a formula:

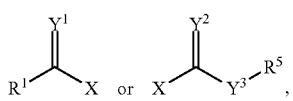

wherein X is a leaving group.

It is understood that the disclosed methods can be used in connection with the disclosed compounds, compositions, kits, and uses.

D. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable derivatives (e.g., salt(s)) thereof) as an active ingredient, a pharmaceutically acceptable carrier, and, optionally, other therapeutic ingredients or adjuvants. The compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The disclosed compounds can be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and can be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions encompass any composition made by admixing a compound of the present invention and a pharmaceutically acceptable carrier.

As used herein, the term "pharmaceutically acceptable salts" refers to salts prepared from pharmaceutically acceptable non-toxic bases or acids. When a disclosed compound is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable derivatives thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Pharmaceutical compositions suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment of conditions which require activation of $M_1$, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The disclosed pharmaceutical compositions can further comprise other therapeutically active compounds, as discussed further herein, which are usually applied in the treatment of the above mentioned pathological conditions.

It is understood that the disclosed compositions can be prepared from the disclosed compounds. It is also understood that the disclosed compositions can be employed in the disclosed methods of using.

E. KITS

In one aspect, the invention relates to kits comprising at least one compound having a structure represented by a formula:

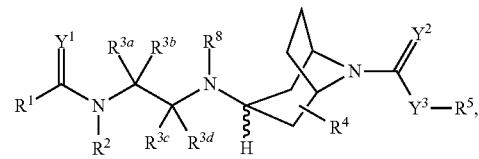

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof, and one or more of: a. at least one agent known to increase $M_1$ receptor activity; b. at least one agent known to decrease $M_1$ receptor activity; c. at least one agent known to treat a cholinergic dysfunction; or d. instructions for treating a disorder associated with cholinergic dysfunction.

For example, in a further aspect, a kit comprises at least one compound having a structure represented by a formula:

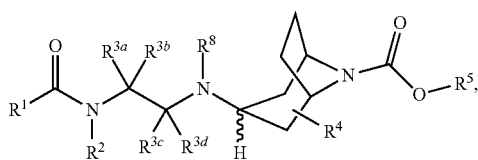

wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ independently comprise hydrogen or optionally substituted organic residue comprising from 1 to 6 carbons; wherein $R^4$ comprises ten substituents independently selected from hydrogen, halogen, hydroxyl, nitrile, nitro, thiol, optionally substituted amino, and optionally substituted organic residue comprising from 1 to 6 carbons; and wherein $R^5$ is an optionally substituted organic residue comprising from 1 to 6 carbons, and wherein $R^8$ is hydrogen, a hydrolysable residue, or an optionally substituted organic residue comprising 1 to 6 carbons; or a pharmaceutically acceptable derivative thereof.

In a further aspect, the at least one compound and the at least one agent are co-formulated. In a further aspect, the at least one compound and the at least one agent are co-packaged.

It is understood that the disclosed kits can be prepared from the disclosed compounds, products, and pharmaceutical compositions. It is also understood that the disclosed kits can be employed in connection with the disclosed methods of using.

F. METHODS OF USING THE COMPOUNDS AND COMPOSITIONS

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In one aspect, the compounds can be coadministered with anti-Alzheimer's agents, beta-secretase inhibitors, gamma-secretase inhibitors, orthosteric muscarinic agonists, muscarinic potentiators, cholinesterase inhibitors, HMG-CoA reductase inhibitors, NSAIDs and anti-amyloid antibodies. In a further aspect, the compounds can be administered in combination with sedatives, hypnotics, anxiolytics, antipsychotics (typical and atypical), selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders associated with selective $M_1$ receptor activation. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders associated with $M_1$ receptor activity in a subject comprising the step of administering to the subject at least one disclosed compound; at least one disclosed pharmaceutical composition; and/or at least one disclosed product in a dosage and amount effective to treat the disorder in the subject.

The invention is directed at the use of described chemical compositions to treat diseases or disorders in patients (preferably human) wherein the $M_1$ receptor is involved, such as Alzheimer's disease (both palliative cognitive and disease-modifying), cognitive impairment, schizophrenia, pain disorders (including acute pain, neuropathic pain and inflammatory pain), and sleep disorders, by administering one or more disclosed compounds or products.

In one aspect, provided is a method for treating or preventing anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool for disorders including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Also provided is a method for the treatment of a disorder in a mammal comprising the step of administering to the mammal at least one disclosed compound, composition, or medicament.

In one aspect, the NMDA receptor is central to a wide range of CNS processes, and plays a role in a variety of disease states in humans or other species. The action of the $M_1$ receptor potentiates NMDA receptor function, which increases activation of the NMDA receptor following glutamate release from the presynaptic terminal. Changes in NMDA-mediated neurotransmission have been implicated in certain neuropsychiatric disorders such as dementia, depression and psychoses, for example schizophrenia, and learning and memory disorders, for example attention deficit disorders and autism.

In one aspect, the disclosed compounds have utility in treating a variety of neurological and psychiatric disorders associated with the $M_1$ receptor, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age-related cognitive decline; anxiety disorders including acute stress disorder, agoraphobia, generalized anxiety disorder, obsessive-compulsive disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

In a specific aspect, the present invention provides a method for treating cognitive disorders, comprising: administering to a patient in need thereof an effective amount of a compound of the present invention. Particular cognitive disorders are dementia, delirium, amnestic disorders and age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources. In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D.C.) provides a diagnostic tool that includes anxiety disorders are generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

In a further specific aspect, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-W-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In a further specific aspect, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse; and tolerance of, dependence on or withdrawal from substances of abuse. At present, the text revision of the fourth edition of the Diagnostic and Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

In a still further aspect, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In a further aspect, the present invention provides a method for treating obesity or eating disorders associated with excessive food intake and complications associated therewith, comprising: administering to a patient in need thereof an effective amount of a compound of the present invention. At present, obesity is included in the tenth edition of the International Classification of Diseases and Related Health Problems (ICD-10) (1992 World Health Organization) as a general medical condition. The text revision of the fourth edition of the Diagnostic and Statistical Manual of Mental Disorders (DSM-IV-TR) (2000, American Psychiatric Association, Washington D.C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-W-TR. The skilled artisan will recognize that there are alternative nomenclatures, nosologies and classification systems for general medical conditions, and that these systems evolve with medical and scientific progress. Thus, the term "obesity or eating disorders associated with excessive food intake" is intended to include like conditions and disorders that are described in other diagnostic sources.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the subject compound can be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, Zolpidem, and salts thereof, and combinations thereof, and the like, or the subject compound can be administered in conjunction with the use of physical methods such as with light therapy or electrical stimulation.

In a further aspect, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In a further aspect, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In one aspect, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In the treatment of conditions which require activation of $M_1$ an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for activating $M_1$ activity in at least one cell, comprising the step of contacting the at least one cell with at least one compound having a structure represented by a formula:

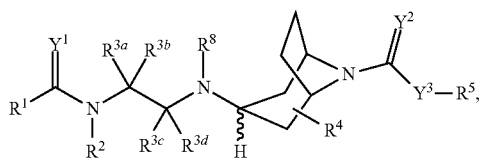

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof, in an amount effective to activate $M_1$ activity response in the at least one cell. In a further aspect, the cell is mammalian, for example human. In a further aspect, the cell has been isolated from a subject prior to the contacting step. In a further aspect, contacting is via administration to a subject.

For example, in a further aspect, the invention relates to methods for activating $M_1$ activity in at least one cell, comprising the step of contacting the at least one cell with at least one compound having a structure represented by a formula:

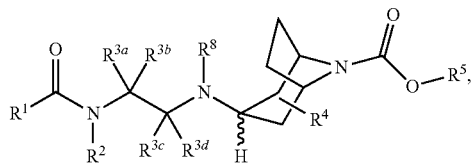

wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ independently comprise hydrogen or optionally substituted organic residue comprising from 1 to 6 carbons; wherein $R^4$ comprises ten substituents independently selected from hydrogen, halogen, hydroxyl, nitrile, nitro, thiol, optionally substituted amino, and optionally substituted organic residue comprising from 1 to 6 carbons; and wherein $R^5$ is an optionally substituted organic residue comprising from 1 to 6 carbons, and wherein $R^8$ is hydrogen, a hydrolysable residue, or an optionally substituted organic residue comprising 1 to 6 carbons; or a pharmaceutically acceptable derivative thereof.

In a further aspect, the invention relates to methods for activating $M_1$ activity in a subject comprising the step of administering to the subject at least one compound having a structure represented by a formula:

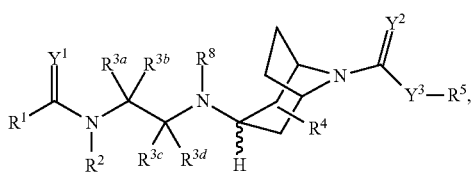

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or an optionally substituted organic residue comprising 1 to 6 carbons, or a pharmaceutically acceptable derivative thereof, in a dosage and amount effective to activate $M_1$ activity in the subject. In a further aspect, the subject is a mammal, for example, human. In a further aspect, the mammal has been diagnosed with a need for $M_1$ receptor agonism prior to the administering step. In a further aspect, the mammal has been diagnosed with a need for $M_1$ activation prior to the administering step. In one aspect, the method further comprises the step of identifying a subject in need of $M_1$ receptor agonism.

For example, in a further aspect, the invention relates to methods for activating $M_1$ activity in a subject comprising the step of administering to the subject at least one compound having a structure represented by a formula:

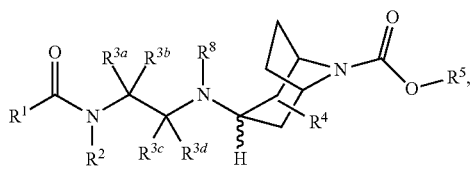

wherein R¹ is an optionally substituted organic residue comprising from 1 to 12 carbons; wherein R² is hydrogen, a hydrolysable residue, or an optionally substituted organic residue comprising 1 to 6 carbons; wherein $R^{3a}$, $R^{3b}$, $R^{3c}$, and $R^{3d}$ independently comprise hydrogen or optionally substituted organic residue comprising from 1 to 6 carbons; wherein R⁴ comprises ten substituents independently selected from hydrogen, halogen, hydroxyl, nitrile, nitro, thiol, optionally substituted amino, and optionally substituted organic residue comprising from 1 to 6 carbons; and wherein R⁵ is an optionally substituted organic residue comprising from 1 to 6 carbons, and wherein R⁸ is hydrogen, a hydrolysable residue, or an optionally substituted organic residue comprising 1 to 6 carbons; or a pharmaceutically acceptable derivative thereof.

In a further aspect, activating M₁ activity comprises treatment of a disorder associated with cholinergic dysfunction in the subject. In a further aspect, the disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In a further aspect, the disorder is Alzheimer's disease. In a further aspect, the disorder is a neurological and/or psychiatric disorder associated with M₁ receptor activity dysfunction.

In a further aspect, the invention relates to methods for the treatment of a disorder associated with cholinergic dysfunction in a mammal comprising the step of administering to the mammal at least one compound having a structure represented by a formula:

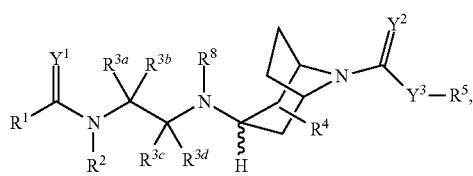

wherein Y¹ and Y² are independently O or S; wherein Y³ is a covalent bond, O, S, or N—R⁶; wherein R¹ is an optionally substituted organic residue comprising from 1 to 12 carbons; wherein R² is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein R⁴ comprises ten substituents independently selected from hydrogen, halogen, hydroxyl, nitrile, nitro, thiol, optionally substituted amino, and an optionally substituted organic residue comprising from 1 to 6 carbons; wherein R⁵ is hydrogen or an optionally substituted organic residue comprising from 1 to 12 carbons, with the proviso that wherein Y³ is a covalent bond, then R⁵ is hydrogen or an optionally substituted organic residue comprising from 1 to 6 carbons; wherein R⁶, when present, is independently selected from hydrogen, a hydrolysable residue, and an optionally substituted organic residue comprising from 1 to 6 carbons; and wherein R⁸ is hydrogen, a hydrolysable residue, or an optionally substituted organic residue comprising 1 to 6 carbons, or a pharmaceutically acceptable derivative thereof, in a dosage and amount effective to treat the disorder in the mammal. In a further aspect, the mammal is a human. In a further aspect, the mammal has been diagnosed with a need for treatment for the disorder prior to the administering step. In one aspect, the method further comprises the step of identifying a subject in need of treatment for the disorder.

For example, in a further aspect, the invention relates to methods for the treatment of a disorder associated with cholinergic dysfunction in a mammal comprising the step of administering to the mammal at least one compound having a structure represented by a formula:

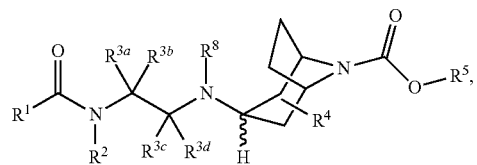

wherein R¹ is an optionally substituted organic residue comprising from 1 to 12 carbons; wherein R² is hydrogen, a hydrolysable residue, or an optionally substituted organic residue comprising 1 to 6 carbons; wherein $R^{3a}$, $R^{3b}$, $R^{3c}$, and $R^{3d}$ independently comprise hydrogen or optionally substituted organic residue comprising from 1 to 6 carbons; wherein R⁴ comprises ten substituents independently selected from hydrogen, halogen, hydroxyl, nitrile, nitro, thiol, optionally substituted amino, and optionally substituted organic residue comprising from 1 to 6 carbons; and wherein R⁵ is an optionally substituted organic residue comprising from 1 to 6 carbons, and wherein R⁸ is hydrogen, a hydrolysable residue, or an optionally substituted organic residue comprising 1 to 6 carbons; or a pharmaceutically acceptable derivative thereof.

In a further aspect, the disorder is selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders. In a further aspect, the disorder is Alzheimer's disease. In a further aspect, the disorder is a neurological and/or psychiatric disorder associated with M₁ receptor activity dysfunction.

It is understood that the disclosed methods can be used in connection with the disclosed compounds, compositions, kits, and uses.

2. Manufacture of a Medicament

The present invention is further directed to a method for the manufacture of a medicament for activating M₁ receptor (e.g., treatment of one or more neurological and/or psychiatric disorder associated with M₁ dysfunction) in mammals (e.g., humans) comprising combining one or more disclosed compounds, products, or compositions with a pharmaceutically acceptable carrier or diluent.

For example, in one aspect, the invention relates to methods for manufacturing a medicament comprising combining at least one compound having a structure represented by a formula:

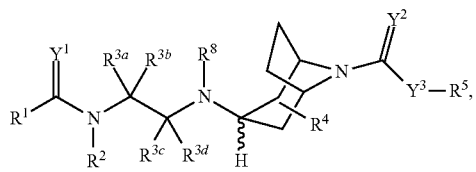

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or a pharmaceutically acceptable derivative thereof, with a pharmaceutically acceptable carrier or diluent.

For example, in a further aspect, the invention relates to methods for manufacturing a medicament comprising combining at least one compound having a structure represented by a formula:

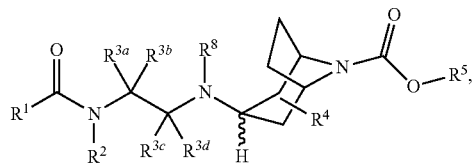

wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ independently comprise hydrogen or optionally substituted organic residue comprising from 1 to 6 carbons; wherein $R^4$ comprises ten substituents independently selected from hydrogen, halogen, hydroxyl, nitrile, nitro, thiol, optionally substituted amino, and optionally substituted organic residue comprising from 1 to 6 carbons; and wherein $R^5$ is an optionally substituted organic residue comprising from 1 to 6 carbons, and wherein $R^8$ is hydrogen, a hydrolysable residue, or an optionally substituted organic residue comprising 1 to 6 carbons; or a pharmaceutically acceptable derivative thereof.

It is understood that the disclosed methods can be performed with the disclosed compounds, products, and pharmaceutical compositions. It is also understood that the disclosed methods can be employed in connection with the disclosed methods of using.

3. Use of Compounds

In one aspect, the invention relates to uses of a compound for $M_1$ receptor activation, the compound having a structure represented by a formula:

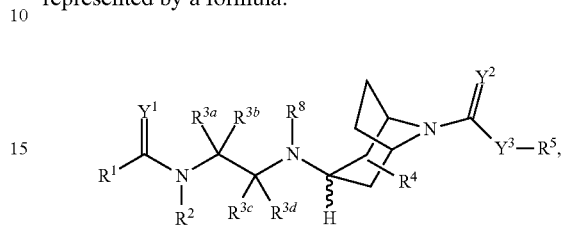

wherein $Y^1$ and $Y^2$ are independently O or S; wherein $Y^3$ is a covalent bond, O, S, or N—$R^6$; wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ comprise four substituents independently selected from hydrogen, halogen or an optionally substituted organic residue comprising from 1 to 6 carbons; wherein $R^4$ comprises ten substituents independently selected from hydrogen, halogen, hydroxyl, nitrile, nitro, thiol, optionally substituted amino, and an optionally substituted organic residue comprising from 1 to 6 carbons; wherein $R^5$ is hydrogen or an optionally substituted organic residue comprising from 1 to 12 carbons, with the proviso that wherein $Y^3$ is a covalent bond, then $R^5$ is hydrogen or an optionally substituted organic residue comprising from 1 to 6 carbons; wherein $R^6$, when present, is independently selected from hydrogen, a hydrolysable residue, and an optionally substituted organic residue comprising from 1 to 6 carbons; and wherein $R^8$ is hydrogen, a hydrolysable residue, or a pharmaceutically acceptable derivative thereof. In a further aspect, the use involves a compound that activates $M_1$ receptor response activity, having an $EC_{50}$ of less than about 10 µM. In a further aspect, the use involves a compound used for the treatment of a disorder associated with cholinergic dysfunction in a mammal.

For example, in a further aspect, the invention relates to uses of a compound for $M_1$ receptor activation, the compound having a structure represented by a formula:

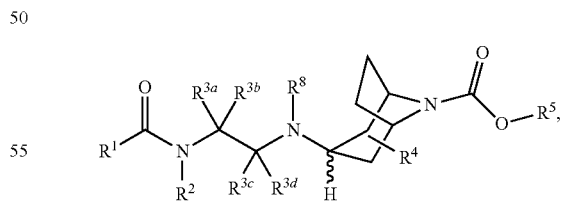

wherein $R^1$ is an optionally substituted organic residue comprising from 1 to 12 carbons; wherein $R^2$ is hydrogen, a hydrolysable residue, or an optionally substituted organic residue comprising 1 to 6 carbons; wherein $R^{3a}$, $R^{3b}$, $R^{3c}$, and $R^{3d}$ independently comprise hydrogen or optionally substituted organic residue comprising from 1 to 6 carbons; wherein $R^4$ comprises ten substituents independently selected from hydrogen, halogen, hydroxyl, nitrile, nitro, thiol, optionally substituted amino, and optionally substituted organic residue comprising from 1 to 6 carbons; and wherein $R^5$ is an optionally substituted organic residue comprising from 1 to 6 carbons, and wherein $R^8$ is hydrogen, a hydrolysable residue, or an optionally substituted organic residue comprising 1 to 6 carbons; or a pharmaceutically acceptable derivative thereof.

It is understood that the disclosed uses can be employed in connection with the disclosed compounds, methods, compositions, and kits.

4. Allosteric and Bitopic Activation of the $M_1$ Receptor

Also provided is a method for allosteric activation (allosteric agonism) of the $M_1$ receptor in at least one cell comprising the step of contacting the at least one cell with at least one disclosed compound in an amount effective to activate $M_1$ receptor activity in the at least one cell. Also provided is a method for bitopic activation (bitopic agonism) of the $M_1$ receptor in at least one cell comprising the step of contacting the at least one cell with at least one disclosed compound in an amount effective to activate $M_1$ receptor activity in the at least one cell. In a further aspect, provided is a method for activation (allosteric agonism or bitopic agonism) of the $M_1$ receptor in a subject, the method comprising the step of administering to the subject a therapeutically effective amount of at least one disclosed compound, in a dosage and amount effective to activate $M_1$ receptor activity in the subject. In a further aspect, the method can be applied to a subject, e.g., a mammal, including, for example, a human.

5. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder treatable by activation of the $M_1$ receptor and/or a need for activation of $M_1$ receptor activity prior to the administering step. In some aspects of the disclosed method, the subject has been diagnosed with anxiety or a related disorder prior to the administering step. In some aspects of the disclosed methods, the subject has been identified with a need for treatment prior to the administering step. In some aspects of the disclosed method, the subject has been identified with a disorder treatable by activation of the $M_1$ receptor and/or or a need for activation/agonism of $M_1$ activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

G. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following examples. Starting materials and the requisite intermediates are in some cases commercially available, or can be prepared according to literature procedures or as illustrated herein. All $^1$H NMR spectra were obtained on instrumentation at a field strength of 300 to 500 MHz.

1. Syntheses of Alkyl 3-((2-amidoethyl)amino)-8-azabicyclo[3.2.1]octane-8-carboxylate Analogs Compounds were prepared according to the following procedures:

a. Example 1

Ethyl 3-(2-(thiophene-2-carboxamido)ethylamino)-8-azabicyclo[3.2.1]octane-8-carboxylate

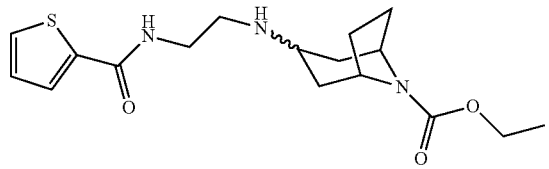 [SMILES: CCOC(=O)N1C2CCC1CC(NCCNC(=O)c1cccs1)C2]

General Procedure: A mixture of tert-butyl 2-aminoethyl-carbamate (40 mg, 0.25 mmol), and thiophene-2-carbonyl chloride (29 µL, 0.275 mmol) in dichloromethane (DCM)(2 mL) was treated with PS-DIEA resin (Biotage 4.0 mmol/g) (100 mg, 0.4 mmol) and gently agitated for an 18 hour period. The slurry was then treated with MP-Isocyanate resin (Biotage, 1.18 mmol/g) (100 mg, 0.118 mmol) and PS-Trisamine resin (Biotage, 3.9 mmol/g) (100 mg, 0.39 mmol) and gently agitated for a four hour period. The resin was then removed by filtration and washed with 1 mL DCM. The combined filtrates were treated with trifluoroacetic acid (1 mL) for a 2 hour period at ambient temperature. The crude mixture was then concentrated under reduced pressure. The crude was then treated with ethyl 3-oxo-8-azabicyclo[3.2.1]octane-8-carboxylate (46 mg, 0.23 mmol), MP(OAc)$_3$BH (Biotage, 2.41 mmol/g) (250 mg, 0.6 mmol) and DMF (1.5 mL). The slurry was gently agitated for a 72 hour period, the resin removed by filtration, washed with DCM (1 mL), and concentrated under reduced pressure. The crude mixture was purified on a preparative C18 column using Acetonitrile 0.1% TFA/H$_2$O 0.1% TFA as a mobile phase. The desired fractions were combined and concentrated under reduce pressure to afford the title compound as the TFA salt. (33 mg, 28%) LC=99% 214 nm, $R_T$=1.67 min, m/z=352 (m+1) $^1$H NMR (CDCl$_3$-d$_1$) 8.2 (m, 1H), 7.6 (m, 1H), 7.5 (m, 1H), 7.0 (m, 1H)

4.3 (m, 1H), 4.1 (q, J=7 Hz, 2H), 3.7 (m, 2H), 3.2 (m, 2H), 3.1 (m, 1H), 2.5 (m, 1H), 2.0 (m, 6H), 1.7 (m, 3H), 1.2 (t, J=7 Hz, 3H).

b. Example 2

Ethyl 3-(2-(2-fluorobenzamido)ethylamino)-8-azabicyclo[3.2.1]octane-8-carboxylate

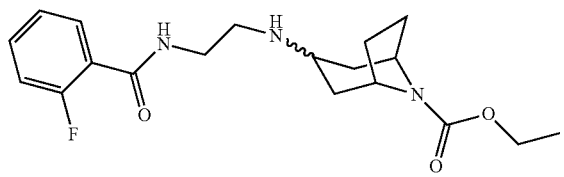 [SMILES: CCOC(=O)N1C2CCC1CC(NCCNC(=O)c1ccccc1F)C2]

Following the General Procedure, tert-butyl 2-aminoethylcarbamate (40 mg, 0.25 mmol), 2-fluorobenzoyl chloride (32 µL, 0.275 mmol), PS-DIEA resin (Biotage 4.0 mmol/g) (100 mg, 0.4 mmol), ethyl 3-oxo-8-azabicyclo[3.2.1]octane-8-carboxylate (46 mg, 0.23 mmol), and MP(OAc)$_3$BH (Biotage, 2.41 mmol/g) (250 mg, 0.6 mmol) afforded the title compound as the TFA salt (45 mg, 37%), LC=98% 214 nm, R$_T$=1.70 min, m/z=364 (m+1) $^1$H NMR (CDCl$_3$-d$_1$) 8.0 (m, 1H), 7.7 (m, 1H), 7.5 (m, 1H), 7.1 (m, 1H), 4.3 (m, 2H), 4.1 (q, J=7 Hz, 2H), 3.7 (m, 2H), 3.3 (m, 2H), 3.2 (m, 1H), 2.4 (m, 1H), 1.9 (m, 6H), 1.6 (m, 3H), 1.2 (t, J=7 Hz, 3H).

C. Examples 3-25

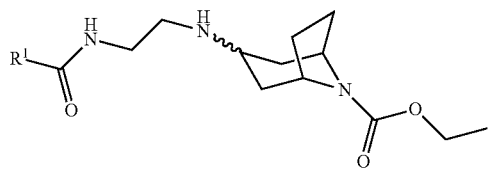

Following the General Procedure, tert-buty 2-aminoethylcarbamate (2 mL of a 0.125 M solution in DCM, 0.25 mmol), R$^1$-substituted acid chloride (0.275 mmol), PS-DIEA resin (Biotage 4.0 mmol/g) (100 mg, 0.4 mmol), ethyl 3-oxo-8-azabicyclo[3.2.1]octane-8-carboxylate (1.5 mL of a 0.158 M solution in DMF, 0.23 mmol), and MP(OAc)$_3$BH (Biotage, 2.41 mmol/g) (250 mg, 0.6 mmol) afforded the title compounds as the TFA salt. The results are compiled in Table 1.

d. Intermediate 1: N-(2-oxoethyl)benzamide

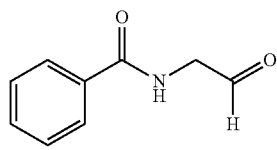 [SMILES: O=CCNC(=O)c1ccccc1]

General Procedure: In a round bottom flask with a stir bar, a solution of allyl amine (10 mL, 133.6 mmol) in dichloromethane (350 mL) was cooled to 0° C. A solution of benzoyl chloride (17.05 mL, 147.0 mmol) in dichloromethane (20 mL) was added dropwise via addition funnel. Once the addition was complete, the solution was stirred at 0° C. for 2 h. The solution was concentrated and the residue was purified on silica gel chromatography (Combiflash. Rf system, 330 g RediSep cartridge) using EtOAc/hexanes as a mobile phase. The desired fractions were collected and concentrated to afford N-allylbenzamide (19.6 g, 91%) as a yellow oil. N-allylbenzamide (1.0 g, 6.21 mmol) was dissolved in dichloromethane (60 mL) and cooled to −78° C. A Tygon tube connected to an ozone generator was fitted with a gas dispersion tube and a stream of ozone was bubbled through the solution at −78° C. Once a pale blue color persisted in the solution, the ozone stream was removed and the solution was treated with dimethyl sulfide (13 mL, 186 mmol) and allowed to warm to ambient temperature over 30 min. The solution was concentrated to give a yellow residue that was subjected to high vacuum for 2 h. The resulting N-(2-oxoethyl)benzamide was used without further purification.

e. Example 26 ethyl 3-((3-exo)-(2-benzamidoethyl)amino)-8-azabicyclo[3.2.1]octane-8-carboxylate

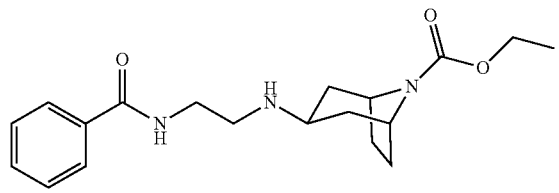 [SMILES: CCOC(=O)N1C2CCC1CC(NCCNC(=O)c1ccccc1)C2]

In a round bottom flask with a stir bar, N-(2-oxoethyl)benzamide (57.4 mg, 0.35 mmol, Intermediate 1) and (3-exo)-ethyl 3-amino-8-azabicyclo[3.2.1]octane-8-carboxylate (70.0 mg, 0.35 mmol, prepared according to: Blackburn, C.; et al. *Bioorg. Med. Chem. Lett.* 2006 (16), 2621) were dissolved in 1,2-dichloroethane (3.5 mL) at room temperature and stirred for 10 minutes. Sodium triacetoxyborohydride (112.2 mg, 0.53 mmol) was added and the reaction was vigorously stirred at room temperature for 5 h. Sodium bicarbonate solution (5 mL) was added and the mixture was diluted with 10 mL of dichloromethane. The biphasic mixture was passed through a phase separator and the organic phase was then concentrated. The residual oil was purified on a preparative Phenomenex Luna-C18 column using 0.1% TFA in H$_2$O/acetonitrile as a mobile phase. The desired fractions were combined and concentrated to afford the title compound. (82.8 mg, 67%) LCMS: R$_T$=0.648 min, >99% @ 254 nm, >99% @ 220 nm; m/z (M+1)$^+$=346. $^1$H NMR (400 MHz, CDCl$_3$, δ (ppm)): 7.9-7.8 (m; 2H), 7.6-7.5 (m; 1H), 7.5-7.4 (m; 2H), 4.4-4.3 (m; 2H), 4.1 (q; J=7 Hz; 2H), 3.8-3.7 (m; 1H) 3.6 (dd; J=6, 6 Hz; 2H), 3.2 (dd; J=6, 6 Hz; 2H), 2.1-1.9 (m; 4H), 1.8-1.6 (m; 4H), 1.3 (t; J=7 Hz; 3H). HRMS calculated for C$_{19}$H$_{28}$N$_3$O$_3$ (M+H)$^+$ m/z: 346.2131, measured: 346.2129.

Alternatively Example 26 can be prepared according to the following procedure: In a round bottom flask with a stir bar, N-(2-oxoethyl)benzamide (756 mg, 4.64 mmol, Intermediate 1) and (3-exo)-tert-butyl 3-amino-8-azabicyclo[3.2.1]octane-8-carboxylate (920 mg, 4.64 mmol, prepared according to: Blackburn, C.; et al. *Bioorg. Med. Chem. Lett.* 2006 (16), 2621) were dissolved in 1,2-dichloroethane (50 mL) at room temperature and stirred for 10 minutes. Sodium triacetoxyborohydride (1.48 g, 6.96 mmol) was added and the reaction was vigorously stirred at room temperature for 5 h. Sodium bicarbonate solution (20 mL) was added and the mixture was diluted with 30 mL of dichloromethane. The biphasic mixture was passed through a phase separator and the organic phase was then concentrated. The residue was then dissolved in 1,4-dioxane (50 mL) at ambient temperature and (9H-fluoren-9-yl)methyl chloroformate (1.2 g, 4.71 mmol) was added followed by a saturated NaHCO$_3$ solution (20 mL). This mixture was stirred at ambient temperature for 3 h. Then, the mixture was diluted with dichloromethane (50 mL) and vigorously stirred for 10 minutes. Next, this mixture was passed through a phase separator and the organic phase was then concentrated. The residue was purified on silica gel chromatography (Combiflash Rf system, EtOAc/hexanes) to yield 1.08 g (42%) of a beige solid. The solid was dissolved in dichloromethane and cooled to 0° C. It was treated with HCl/dioxane solution (2.0 mL, 4N) and stirred at 0° C. for 10 minutes followed by warming to ambient temperature. The solution was concentrated and the residual HCl salt was used without further purification. The amine HCl salt (35 mg, 0.065 mmol) was dissolved in dichloromethane (1.5 ml) and triethylamine (40 µL, 0.29 mmol) was added with stirring at ambient temperature. To the solution was added ethyl chloroformate (6.8 µL, 0.72 mmol). The reaction mixture was stirred for 30 minutes and then piperidine (106 µL, 1.05 mmol) was added. This solution was stirred for an additional 18 h. The reaction mixture was concentrated and the residue was purified on a preparative Phenomenex Luna-C18 column using 0.1% TFA in H$_2$O/acetonitrile as a mobile phase. The desired fractions were combined and concentrated to afford the title compound. (12 mg, 53%)

f. Example 27 ethyl 3-((3-endo)-(2-benzamidoethyl)amino)-8-azabicyclo[3.2.1]octane-8-carboxylate

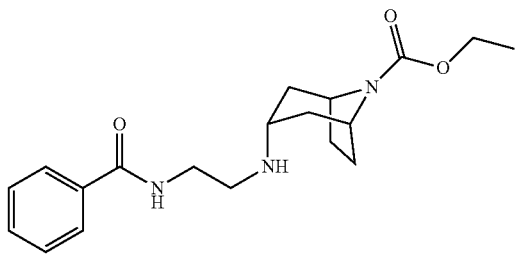 [SMILES: CCOC(=O)N1C2CCC1CC(NCCNC(=O)c1ccccc1)C2]

In a round bottom flask with a stir bar, N-(2-oxoethyl)benzamide (182 mg, 0.92 mmol, Intermediate 1) and (3-endo)-ethyl 3-amino-8-azabicyclo[3.2.1]octane-8-carboxylate (150 mg, 0.92 mmol) were dissolved in 1,2-dichloroethane (12 mL) at room temperature and stirred for 10 minutes. Sodium triacetoxyborohydride (293 mg, 1.38 mmol) was added and the reaction was vigorously stirred at room temperature for 5 h. Sodium bicarbonate solution (15 mL) was added and the mixture was diluted with 10 mL of dichloromethane. The biphasic mixture was passed through a phase separator and the organic phase was then concentrated. The residual oil was purified on a preparative Phenomenex Luna-C18 column using 0.1% TFA in H$_2$O/acetonitrile as a mobile phase. The desired fractions were combined and concentrated to afford the title compound (119.3 mg, 39%) LCMS: R$_T$=0.648 min, >99% @ 254 nm, >99% @ 220 nm; m/z (M+1)$^+$=346. $^1$H NMR (400 MHz, CDCl$_3$, δ (ppm)): 7.8-7.7 (m; 2H), 7.6-7.5 (m; 1H), 7.5-7.4 (m; 2H), 4.2-4.1 (m; 2H), 4.1 (q; J=7 Hz; 2H), 3.5 (dd; J=6, 6 Hz; 2H), 2.9-2.8 (m; 1H), 2.8-2.7 (m; 2H), 2.2-1.9 (m; 4H), 1.9-1.8 (m; 2H), 1.7-1.6 (m; 2H), 1.2 (t; J=7 Hz; 3H). HRMS calculated for C$_{19}$H$_{28}$N$_3$O$_3$ (M+H)$^+$ m/z: 346.2131, measured: 346.2128.

g. Intermediate 2: tert-Butyl (2-oxoethyl)carbamate

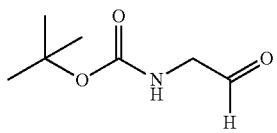

The title compound was prepared by analogy to the preparation of Intermediate 1.

h. Example 28 ethyl 3((3-exo)-(2-(piperidine-1-carboxamido)ethyl)amino)-8-azabicyclo[3.2.1]octane-8-carboxylate

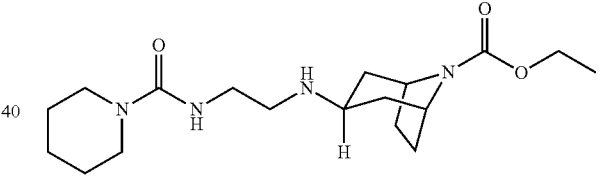

In a round bottom flask with a stir bar, tert-butyl (2-oxoethyl)carbamate (4.1 g, 26 mmol, Intermediate 2) and (3-exo)-ethyl 3-amino-8-azabicyclo[3.2.1]octane-8-carboxylate (5.1 g, 26 mmol, prepared according to: Blackburn, C.; et al. *Bioorg. Med. Chem. Lett.* 2006 (16), 2621) were dissolved in 1,2-dichloroethane (150 mL) at room temperature and stirred for 30 minutes. Sodium triacetoxyborohydride (8.3 g, 39 mmol) was added and the reaction was vigorously stirred at room temperature for 12 h. Sodium bicarbonate solution (60 mL) was added and the mixture was diluted with 100 mL of dichloromethane. The biphasic mixture was passed through a phase separator and the organic phase was then concentrated. The residue was then dissolved in 1,4-dioxane (220 mL) at ambient temperature and (9H-fluoren-9-yl)methyl chloroformate (6.2 g, 24 mmol) was added followed by a saturated NaHCO$_3$ solution (30 mL). This mixture was stirred at ambient temperature for 18 h. The reaction mixture was then diluted with dichloromethane (200 mL) and vigorously stirred for 1 h. Next, the reaction mixture was passed through a phase separator and the organic phase was then concentrated. The residue was purified on silica gel chromatography (Combiflash Rf system, EtOAc/hexanes) to yield 2.53 g (17%) of the desired compound. The solid was dissolved in dichloromethane and cooled to 0° C. This solution was treated with HCl/dioxane solution (2.2 mL, 4N) and stirred at 0° C. for 10 minutes followed by warming to ambient temperature. The solution was concentrated and the residual HCl salt was used without further purification. Triphosgene (8.3 mg, 0.028 mmol) was dissolved in dichloromethane at ambient temperature and piperidine (8.2 µL, 0.084 mmol) was added. The solution was stirred for 5 minutes and then triethylamine (45 µL, 0.032 mmol) was added followed by the amine salt (40 mg, 0.08 mmol). The solution was stirred for 30 minutes and then treated with piperidine (100 µL, 1.05 mmol). After stirring for an additional 2 h at ambient temperate the reaction mixture was concentrated. The residue was purified on a SNAP C18-HS column using 0.1% $NH_4OH$ in $H_2O$/acetonitrile as a mobile phase. The desired fractions were combined and concentrated to afford the title compound. (2.3 mg, 8%) LCMS: $R_T$=0.615 min, >80% by ELSD; m/z $(M+1)^+$=353. $^1H$ NMR (400 MHz, $CDCl_3$, δ (ppm)): 4.3-4.2 (m; 2H), 4.1 (q; J=7 Hz; 2H), 3.5-3.1 (m; 2H), 3.1-2.8 (m; 2H), 2.7-2.6 (m; 2H), 2.4-2.3 (m; 2H), 2.1-1.8 (m; 4H), 1.8-1.7 (m; 2H), 1.7-1.5 (m; 3H), 1.5-1.4 (m; 4H), 1.32-1.26 (m; 2H), 1.26 (t; J=7 Hz; 3H). HRMS calculated for $C_{18}H_{33}N_4O_3$ $(M+H)^+$ m/z: 353.2553, measured: 353.2556.

2. Cell Culture and Uptake Measurements

Cell Culture and Transfections.

Chinese hamster ovary (CHO-K1) cells stably expressing rat $(r)M_1$ were purchased from the American Type Culture Collection and cultured according to their indicated protocol. CHO cells stably expressing human $(h)M_2$, $hM_3$, and $hM_5$ were described previously (Levey et al., 1991); hM1 and hM4 cDNAs were purchased from Missouri S&T cDNA Resource; $rM_4$ cDNA was provided by T. I. Bonner (National Institutes of Health, Bethesda, Md.). hM1, hM4, and rM4 cDNAs were used to stably transfect CHO-K1 cells purchased from the American Type Culture Collection using Lipofectamine2000. To make stable $hM_2$, $hM_4$ and $rM_4$ cell lines for use in calcium mobilization assays, these cells also were stably transfected with a chimeric G-protein $(G_{qi5})$ (provided by B. R. Conklin, University of California, San Francisco) using Lipofectamine 2000. $rM_1$, $hM_3$, and $hM_5$ cells were grown in Ham's F-12 medium containing 10% heat-inactivated fetal bovine serum (FBS), 20 mM HEPES, and 50 µg/mL G418 sulfate. $hM_2$-$G_{qi5}$ and $hM_4$-$G_{qi5}$ cells were grown in the same medium also containing 500 µg/mL Hygromycin B. Stable $rM_4$-$G_{qi5}$ cells were grown in DMEM containing 10% heat-inactivated FBS, 20 mM HEPES, 400 µg/mL G418 sulfate, and 500 µg/mL Hygromycin B. The rat $M_1$ Y381A orthosteric mutant receptor cDNA was generated using the Quik-Change site-directed mutagenesis kit (Stratagene) and verified by sequencing. CHO-K1 cells were stably transfected with this cDNA using Lipofectamine2000 and screened for expression based on calcium mobilization in response to the allosteric $M_1$ agonist N-desmethylclozapine.

Calcium Mobilization Assays.

For low throughput measurement of agonist-evoked increases in intracellular calcium, CHO-K1 cells stably expressing muscarinic receptors were plated in 100 µL of growth medium at $5 \times 10^4$ ($rM_1$, $hM_3$, and $hM_5$) or $6 \times 10^4$ cells per well ($rM_1$ Y381A, $hM_2$, and $rM_4$) in Costar 96-well black-walled, tissue culture (TC)-treated, clear-bottom plates (Fisher). Cells were incubated overnight at 37° C. and 5% $CO_2$. The next day, medium was removed from the cells, and they were incubated with 50 µL of 2 µM Fluo-4/acetoxymethyl ester (Invitrogen, Carlsbad, Calif.) prepared as a 2.3 mM stock in DMSO and mixed in a 1:1 ratio with 10% (w/v) Pluronic F-127 and diluted in assay buffer [HBSS (Invitrogen) supplemented with 20 mM HEPES and 2.5 mM probenecid, pH 7.4] for 1 h at 37° C. and 5% $CO_2$. Dye was removed and replaced with 50 µL of assay buffer. For calcium fluorescence measurements, CRCs of compounds (50 µl, 2×) were added 19 s after the beginning of data collection via a Flexstation II (Molecular Devices, Sunnyvale, Calif.). Fluorescence imaging continued for a total of 130 s acquisition time using an excitation wavelength of 488 nm, an emission wavelength of 525 nm, and a cutoff wavelength of 515 nm. All of the peaks of the calcium response were normalized to the response to a maximally effective concentration of ACh ($EC_{max}$). These normalized peak calcium response values were fit using GraphPad Prism version 4.0 to a four-parameter logistic equation to determine $EC_{50}$ values.

For high throughput measurement of agonist-evoked increases in intracellular calcium, CHO-K1 cells stably expressing muscarinic receptors were plated in growth medium lacking G418 and hygromycin at 15,000 cells/20 µL/well ($hM_1$, $hM_2$-$G_{qi5}$, $hM_3$, $hM_4$-$G_{qi5}$, and $hM_5$) in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with three washes (50 µL) of assay buffer then aspirated to 15 µL. Next, 5 µL of 8 µM Fluo-4/acetoxymethyl ester (Invitrogen, Carlsbad, Calif.) prepared as a 2.3 mM stock in DMSO and mixed in a 1:1 ratio with 10% (w/v) Pluronic F-127 and diluted in assay buffer was added to the wells and the cell plates were incubated for 45 min at 37° C. and 5% $CO_2$. Dye was removed by washing with the ELX 405 (three 50 µL washes of assay buffer) then aspirated to 20 µL. Agonist and compound master plates were formatted in an 11 point CRC format (1:3 dilutions) in 100% DMSO with a starting concentration of 10 mM using the BRAVO liquid handler (Agilent). Test compound CRCs were then transferred to daughter plates (240 mL) using the Echo acoustic plate reformatter (Labcyte, Sunnyvale, Calif.) and then diluted into assay buffer (40 µL) to a 2× stock using a Thermo Fisher Combi (Thermo Fisher Scientific, Waltham, Mass.). Calcium flux was measured using the Functional Drug Screening System (FDSS) 6000 (Hamamatsu Corporation, Tokyo, Japan) as an increase in the fluorescent static ratio. 20 µL of Agonist Compounds were applied to cells using the automated system of the FDSS 6000 at 4 s into the 300 s protocol and the data were collected at 1 Hz. Concentration-response curves were generated using a four-parameter logistical equation in XLfit curve fitting software (IDBS, Bridgewater, N.J.) for Excel (Microsoft, Redmond, Wash.) or Prism (GraphPad Software, Inc., San Diego, Calif.).

3. Potency Results for Exemplary Alkyl 3-((2-amidoethyl)amino)-8-azabicyclo[3.2.1] octane-8-carboxylate Analog M1 Agonists The potency of exemplary disclosed compounds was established using the above-described procedure. The results for potency at the rat $M_1$ receptor are shown in Table 1 and the results for potency at the human $M_1$ receptor are shown in Table 2.

TABLE 1

RAT M₁ POTENCY RESULTS

| Ex. | Structure | Potency (EC$_{50}$, nM) | Efficacy (% Max ACh) | Name | M + H |
|---|---|---|---|---|---|
| 1 | 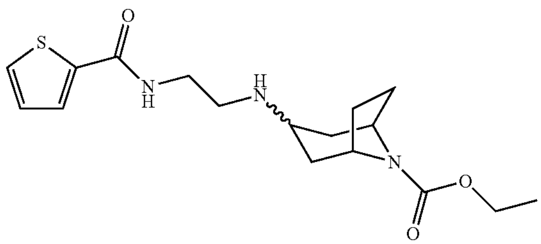 | 74 | 88 | ethyl 3-{[2-(thiophen-2-ylformamido)ethyl]-amino}-8-azabicyclo[3.2.1]octane-8-carboxylate | 352 |
| 2 | 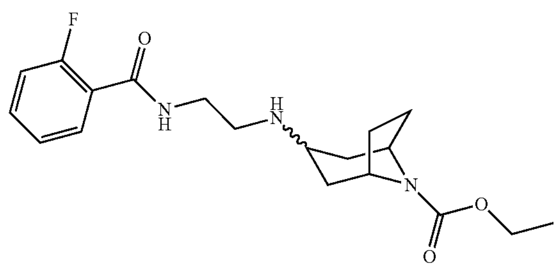 [SMILES: CCOC(=O)N1C2CCC1CC(NCCNC(=O)c1ccccc1F)C2] | 69 | 103 | ethyl 3-({2-[(2-fluorophenyl)formamido]-ethyl}amino)-8-azabicyclo[3.2.1]octane-8-carboxylate | 364 |
| 3 | 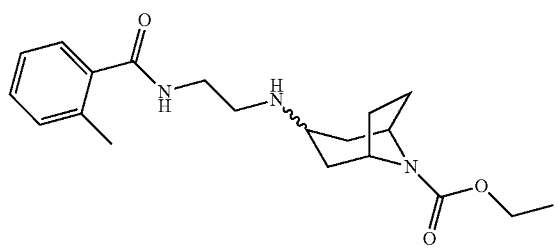 [SMILES: CCOC(=O)N1C2CCC1CC(NCCNC(=O)c1ccccc1C)C2] | 85 | 81 | ethyl 3-({2-[(2-methylphenyl)formamido]-ethyl}amino)-8-azabicyclo[3.2.1]octane-8-carboxylate | 360 |
| 4 | 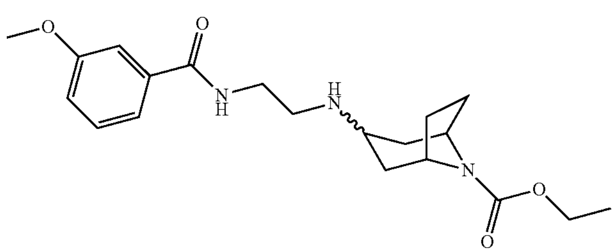 [SMILES: CCOC(=O)N1C2CCC1CC(NCCNC(=O)c1cccc(OC)c1)C2] | 211 | 81 | ethyl 3-({2-[(3-methoxy-phenyl)formamido]-ethyl}amino)-8-azabicyclo[3.2.1]octane-8-carboxylate | 376 |
| 5 | 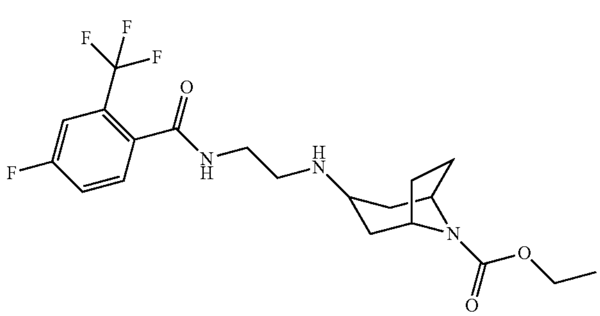 [SMILES: CCOC(=O)N1C2CCC1CC(NCCNC(=O)c1ccc(F)cc1C(F)(F)F)C2] | n.d. | 39 | ethyl 3-[(2-{[4-fluoro-2-(trifluoromethyl)phenyl]-formamido}ethyl)-amino]-8-azabicyclo[3.2.1]octane-8-carboxylate | 432 |

TABLE 1-continued

RAT M₁ POTENCY RESULTS

| Ex. | Structure | Potency (EC$_{50}$, nM) | Efficacy (% Max ACh) | Name | M + H |
|---|---|---|---|---|---|
| 6 | 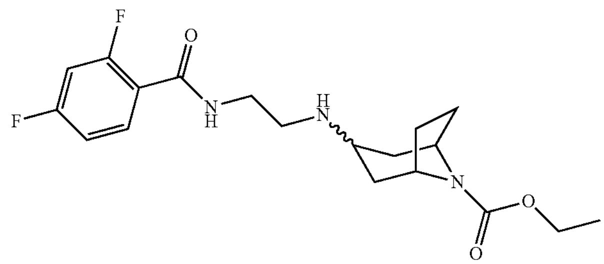 [SMILES: CCOC(=O)N1C2CCC1CC(NCCNC(=O)c1ccc(F)cc1F)C2] | 72 | 82 | ethyl 3-({2-[(2,4-difluorophenyl)formamido]-ethyl}amino)-8-azabicyclo[3.2.1]octane-8-carboxylate | 382 |
| 7 | 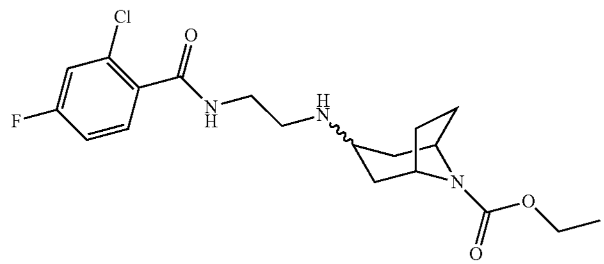 | 96 | 95 | ethyl 3({2-[(2-chloro-4-fluorophenyl)formamido]-ethyl}amino)-8-azabicyclo[3.2.1]octane-8-carboxylate | 398 |
| 8 | 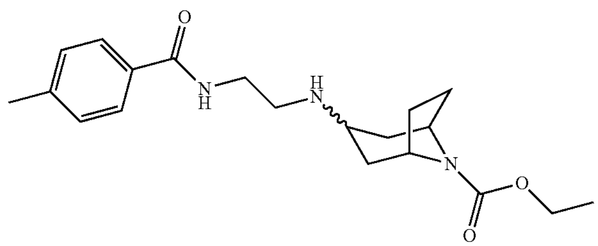 [SMILES: CCOC(=O)N1C2CCC1CC(NCCNC(=O)c1ccc(C)cc1)C2] | n.d. | 47 | ethyl 3-({2-[(4-methylphenyl)formamido]-ethyl}amino)-8-azabicyclo[3.2.1]octane-8-carboxylate | 360 |
| 9 | 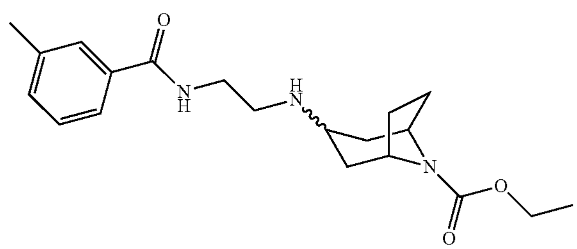 [SMILES: CCOC(=O)N1C2CCC1CC(NCCNC(=O)c1cccc(C)c1)C2] | 115 | 103 | ethyl 3-({2-[(3-methylphenyl)formamido]-ethyl}amino)-8-azabicyclo[3.2.1]octane-8-carboxylate | 360 |
| 10 | 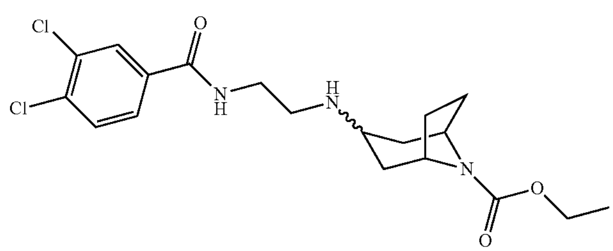 [SMILES: CCOC(=O)N1C2CCC1CC(NCCNC(=O)c1ccc(Cl)c(Cl)c1)C2] | 1020 | 49 | ethyl 3-({2-[(3,4-dichlorophenyl)formamido]-ethyl}amino)-8-azabicyclo[3.2.1]octane-8-carboxylate | 414 |
| 11 | 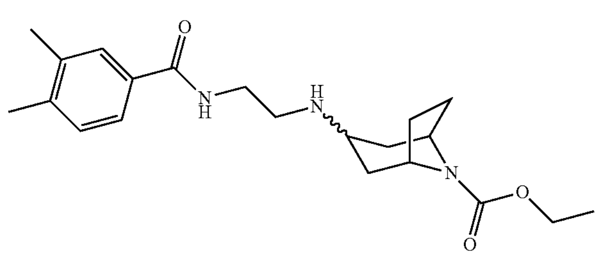 [SMILES: CCOC(=O)N1C2CCC1CC(NCCNC(=O)c1ccc(C)c(C)c1)C2] | n.d. | 48 | ethyl 3-({2-[(3,4-dimethylphenyl)formamido]-ethyl}amino)-8-azabicyclo[3.2.1]octane-8-carboxylate | 374 |

TABLE 1-continued

RAT M₁ POTENCY RESULTS

| Ex. | Structure | Potency (EC$_{50}$, nM) | Efficacy (% Max ACh) | Name | M + H |
|---|---|---|---|---|---|
| 12 | 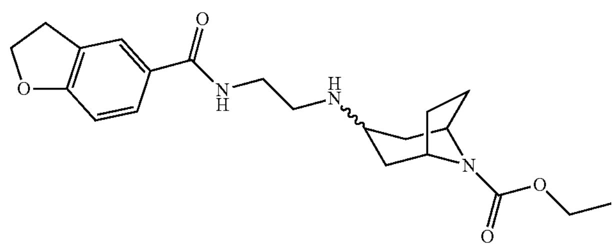 [SMILES: CCOC(=O)N1C2CCC1CC(NCCNC(=O)c1ccc3c(c1)CCO3)C2] | n.d. | 31 | ethyl 3-{[2-(2,3-dihydro-1-benzofuran-5-ylformamido)ethyl]-amino}-8-azabicyclo[3.2.1]octane-8-carboxylate | 388 |
| 13 | 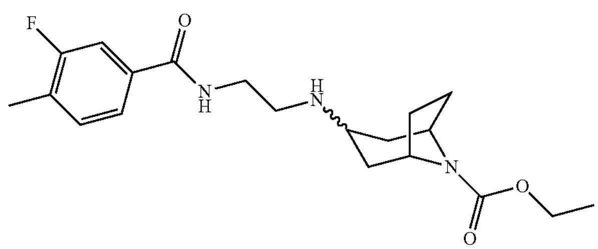 | 631 | 50 | ethyl 3-({2-[(3-fluoro-4-methylphenyl)formamido]-ethyl}amino)-8-azabicyclo[3.2.1]octane-8-carboxylate | 378 |
| 14 | 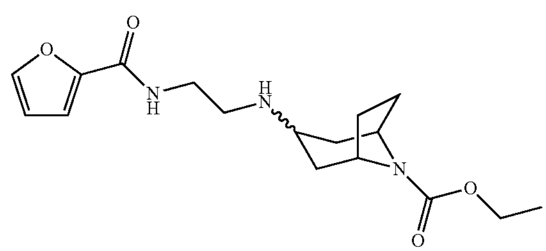 [SMILES: CCOC(=O)N1C2CCC1CC(NCCNC(=O)c1ccco1)C2] | n.d. | 24 | ethyl 3-{[2-(furan-2-ylformamido)ethyl]-amino}-8-azabicyclo[3.2.1]octane-8-carboxylate | 336 |
| 15 | 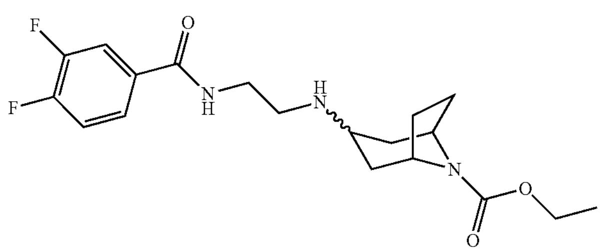 [SMILES: CCOC(=O)N1C2CCC1CC(NCCNC(=O)c1ccc(F)c(F)c1)C2] | 122 | 104 | ethyl 3-({2-[(3,4-difluorophenyl)formamido]-ethyl}amino)-8-azabicyclo[3.2.1]octane-8-carboxylate | 382 |
| 16 | 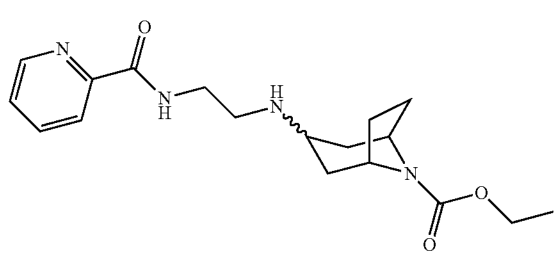 [SMILES: CCOC(=O)N1C2CCC1CC(NCCNC(=O)c1ccccn1)C2] | n.d. | 22 | ethyl 3-{[2-(pyridin-2-ylformamido)ethyl]-amino}-8-azabicyclo[3.2.1]octane-8-carboxylate | 347 |
| 17 | 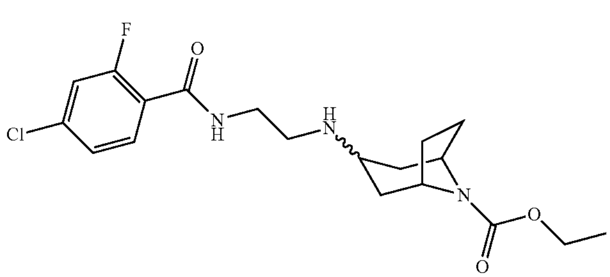 [SMILES: CCOC(=O)N1C2CCC1CC(NCCNC(=O)c1ccc(Cl)cc1F)C2] | n.d. | 20 | ethyl 3-({2-[(4-chloro-2-fluorophenyl)formamido]-ethyl}amino)-8-azabicyclo[3.2.1]octane-8-carboxylate | 398 |

TABLE 1-continued

RAT M₁ POTENCY RESULTS

| Ex. | Structure | Potency (EC$_{50}$, nM) | Efficacy (% Max ACh) | Name | M + H |
|---|---|---|---|---|---|
| 18 | 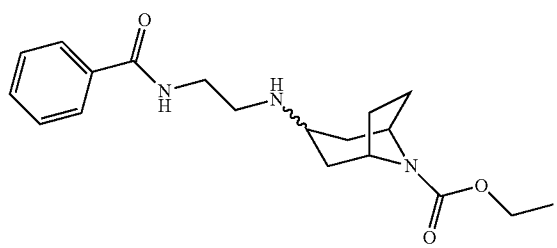 [SMILES: CCOC(=O)N1C2CCC1CC(NCCNC(=O)c1ccccc1)C2] | 67 | 103 | ethyl 3-{[2-(phenylformamido)ethyl]-amino}-8-azabicyclo[3.2.1]octane-8-carboxylate | 346 |
| 19 | 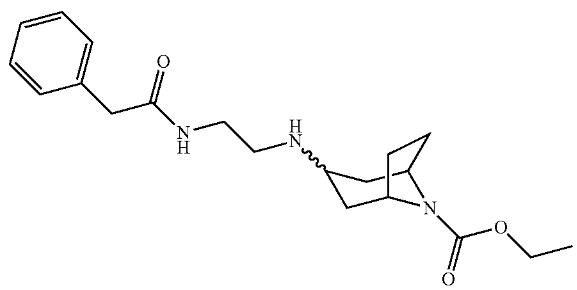 [SMILES: CCOC(=O)N1C2CCC1CC(NCCNC(=O)Cc1ccccc1)C2] | n.d. | 33 | ethyl 3-{[2-(2-phenylacetamido)ethyl]-amino}-8-azabicyclo[3.2.1]octane-8-carboxylate | 360 |
| 20 | 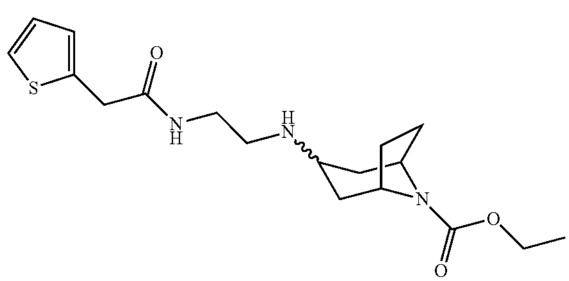 [SMILES: CCOC(=O)N1C2CCC1CC(NCCNC(=O)Cc1cccs1)C2] | n.d. | 51 | ethyl 3-({2-[2-(thiophen-2-yl)acetamido]ethyl}-amino)-8-azabicyclo[3.2.1]octane-8-carboxylate | 366 |
| 21 | 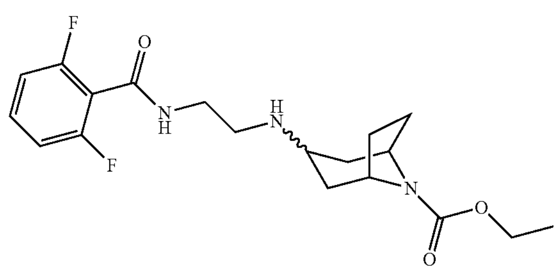 [SMILES: CCOC(=O)N1C2CCC1CC(NCCNC(=O)c1c(F)cccc1F)C2] | 880 | 18 | ethyl 3-({2-[(2,6-difluorophenyl)formamido]-ethyl}amino)-8-azabicyclo[3.2.1]octane-8-carboxylate | 382 |
| 22 | 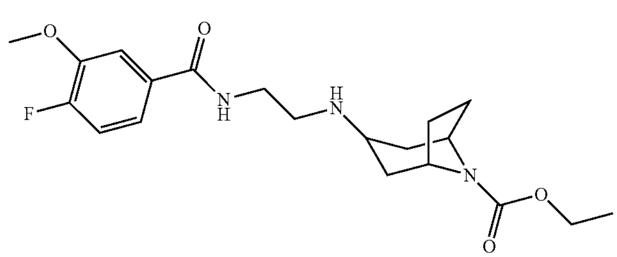 [SMILES: CCOC(=O)N1C2CCC1CC(NCCNC(=O)c1ccc(F)c(OC)c1)C2] | 1463 | 12 | ethyl 3-({2-[(4-fluoro-3-methoxyphenyl)formamido]-ethyl}amino)-8-azabicyclo[3.2.1]octane-8-carboxylate | 394 |

TABLE 1-continued

RAT M₁ POTENCY RESULTS

| Ex. | Structure | Potency (EC$_{50}$, nM) | Efficacy (% Max ACh) | Name | M + H |
|---|---|---|---|---|---|
| 23 | 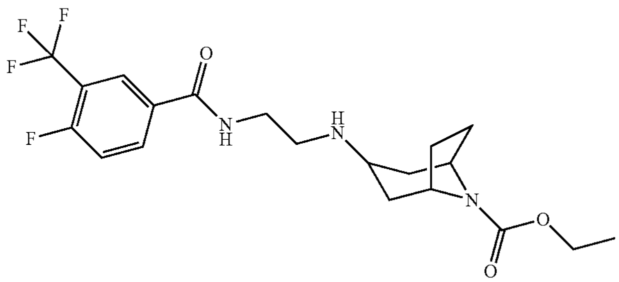 [SMILES: CCOC(=O)N1C2CCC1CC(NCCNC(=O)c1ccc(F)c(C(F)(F)F)c1)C2] | 2717 | 47 | ethyl 3-[(2-{[4-fluoro-3-(trifluoromethyl)phenyl]-formamido}ethyl)amino]-8-azabicyclo[3.2.1]octane-8-carboxylate | 432 |
| 24 | 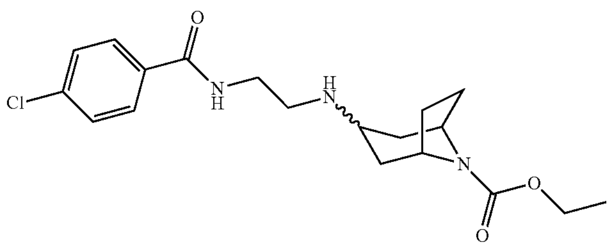 [SMILES: CCOC(=O)N1C2CCC1CC(NCCNC(=O)c1ccc(Cl)cc1)C2] | 1070 | 25 | ethyl 3-({2-[(4-chlorophenyl)formamido]-ethyl}amino)-8-azabicyclo[3.2.1]octane-8-carboxylate | 380 |
| 25 | 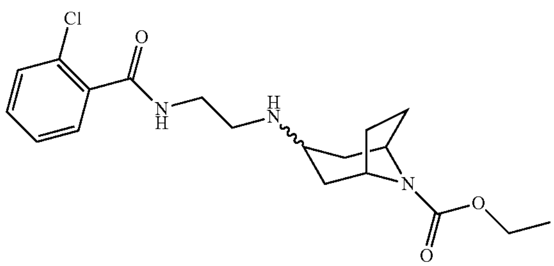 | 112 | 80 | ethyl 3-({2-[(2-chlorophenyl)formamido]-ethyl}amino)-8-azabicyclo[3.2.1]octane-8-carboxylate | 380 |

TABLE 2

HUMAN M₁ POTENCY RESULTS

| Ex. | Structure | Potency (EC$_{50}$, nM) | Efficacy (% Max ACh) | Name | M + H |
|---|---|---|---|---|---|
| 26 | 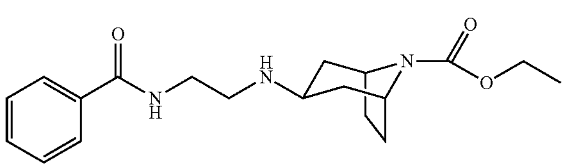 [SMILES: CCOC(=O)N1C2CCC1CC(NCCNC(=O)c1ccccc1)C2] | 1200 | 57 | ethyl 3-((3-exo)-(2-benzamidoethyl)amino)-8-azabicyclo[3.2.1]octane-8-carboxylate | 346 |
| 27 | 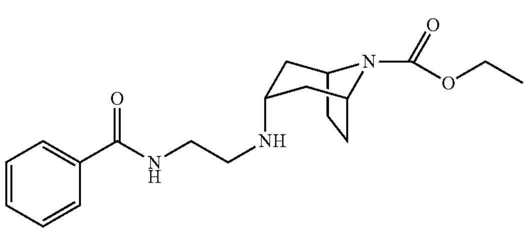 [SMILES: CCOC(=O)N1C2CCC1CC(NCCNC(=O)c1ccccc1)C2] | 210 | 37 | ethyl 3-((3-endo)-(2-benzamidoethyl)amino)-8-azabicyclo[3.2.1]octane-8-carboxylate | 346 |

TABLE 2-continued

HUMAN M₁ POTENCY RESULTS

| Ex. | Structure | Potency (EC$_{50}$, nM) | Efficacy (% Max ACh) | Name | M + H |
|---|---|---|---|---|---|
| 28 | 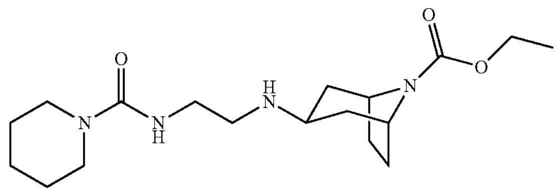 [SMILES: CCOC(=O)N1C2CCC1CC(NCCNC(=O)N1CCCCC1)C2] | 700 | 46 | ethyl 3-((3-exo)-(2-(piperidine-1-carboxamido)ethyl)amino)-8-azabicyclo[3.2.1]octane-8-carboxylate | 353 |
| 29 | 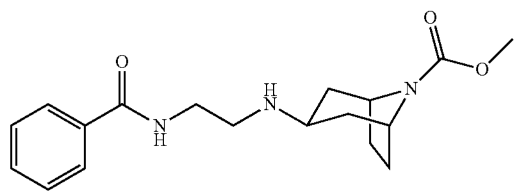 [SMILES: COC(=O)N1C2CCC1CC(NCCNC(=O)c1ccccc1)C2] | n.d. | 7 | methyl 3-((3-exo)-(2-benzamidoethyl)amino)-8-azabicyclo[3.2.1]octane-8-carboxylate | 332 |
| 30 | 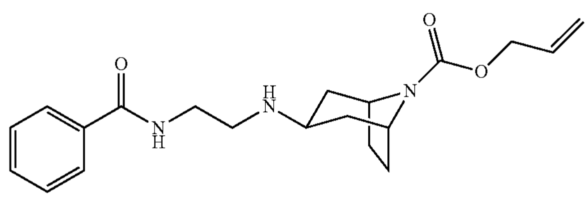 [SMILES: C=CCOC(=O)N1C2CCC1CC(NCCNC(=O)c1ccccc1)C2] | 4200 | 29 | allyl 3-((3-exo)-(2-benzamidoethyl)amino)-8-azabicyclo[3.2.1]octane-8-carboxylate | 358 |
| 31 | 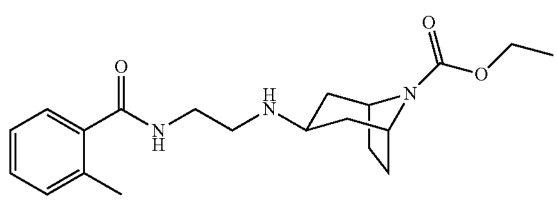 [SMILES: CCOC(=O)N1C2CCC1CC(NCCNC(=O)c1ccccc1C)C2] | 2500 | 38 | ethyl 3-((3-exo)-(2-(2-methylbenzamido)ethyl)-amino)-8-azabicyclo[3.2.1]octane-8-carboxylate | 360 |
| 32 | 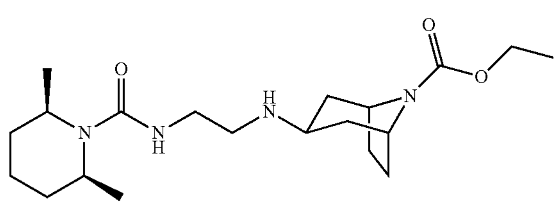 [SMILES: CCOC(=O)N1C2CCC1CC(NCCNC(=O)N1[C@H](C)CCC[C@@H]1C)C2] | 4200 | 26 | ethyl 3-((3-exo)-(2-(cis)-2,6-dimethylpiperidine-1-carboxamido)ethyl)amino)-8-azabicyclo[3.2.1]octane-8-carboxylate | 381 |
| 33 | 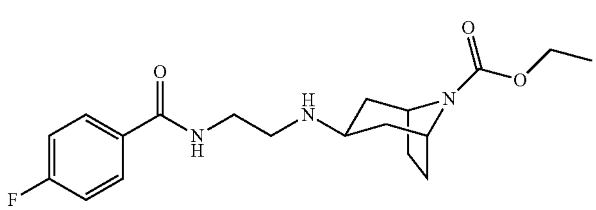 [SMILES: CCOC(=O)N1C2CCC1CC(NCCNC(=O)c1ccc(F)cc1)C2] | 1700 | 48 | ethyl 3-((3-exo)-(2-(4-fluorobenzamido)ethyl)-amino)-8-azabicyclo[3.2.1]octane-8-carboxylate | 364 |
| 34 | 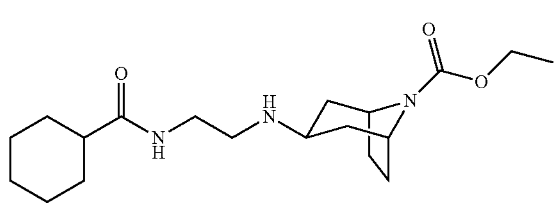 [SMILES: CCOC(=O)N1C2CCC1CC(NCCNC(=O)C1CCCCC1)C2] | 3200 | 25 | ethyl 3-((3-exo)-(2-(cyclohexanecarboxamido)-ethyl)amino)-8-azabicyclo[3.2.1]octane-8-carboxylate | 352 |

TABLE 2-continued

HUMAN M₁ POTENCY RESULTS

| Ex. | Structure | Potency (EC$_{50}$, nM) | Efficacy (% Max ACh) | Name | M + H |
|---|---|---|---|---|---|
| 35 | 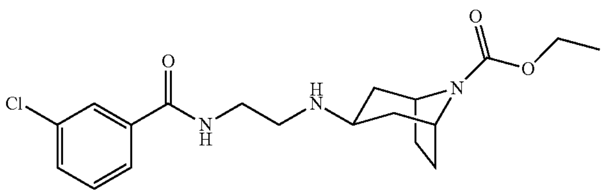 [SMILES: CCOC(=O)N1C2CCC1CC(NCCNC(=O)c1cccc(Cl)c1)C2] | 490 | 57 | ethyl 3-((3-exo)-(2-(3-chlorobenzamido)ethyl)-amino)-8-azabicyclo[3.2.1]octane-8-carboxylate | 380 |
| 36 | 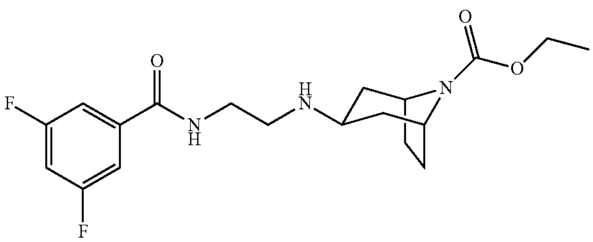 [SMILES: CCOC(=O)N1C2CCC1CC(NCCNC(=O)c1cc(F)cc(F)c1)C2] | 2600 | 37 | ethyl 3-((3-exo)-(2-(3,5-difluorobenzamido)ethyl)-amino)-8-azabicyclo[3.2.1]octane-8-carboxylate | 382 |
| 37 | 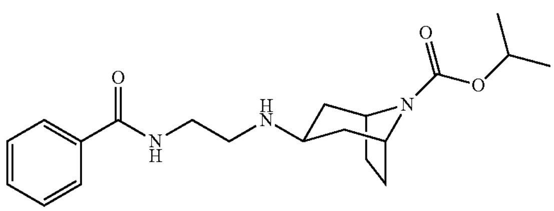 [SMILES: CC(C)OC(=O)N1C2CCC1CC(NCCNC(=O)c1ccccc1)C2] | n.d. | 7 | isopropyl 3-((3-exo)-(2-benzamidoethyl)amino)-8-azabicyclo[3.2.1]octane-8-carboxylate | 360 |
| 38 | 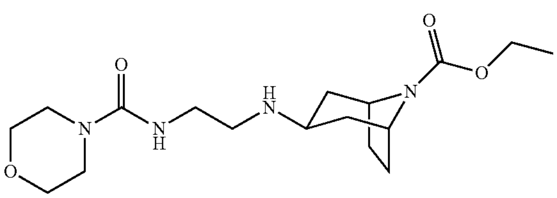 [SMILES: CCOC(=O)N1C2CCC1CC(NCCNC(=O)N1CCOCC1)C2] | 3600 | 37 | ethyl 3-((3-exo)-(2-(morpholine-4-carboxamido)ethyl)-amino)-8-azabicyclo[3.2.1]octane-8-carboxylate | 355 |
| 39 | 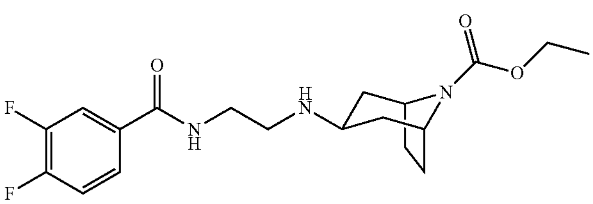 [SMILES: CCOC(=O)N1C2CCC1CC(NCCNC(=O)c1ccc(F)c(F)c1)C2] | 1400 | 46 | ethyl 3-((3-exo)-(2-(3,4-difluorobenzamido)ethyl)-amino)-8-azabicyclo[3.2.1]octane-8-carboxylate | 382 |
| 40 | 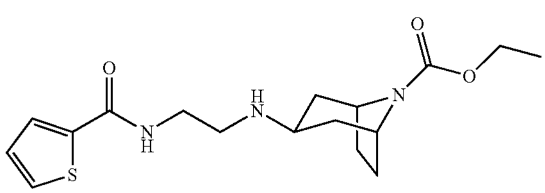 [SMILES: CCOC(=O)N1C2CCC1CC(NCCNC(=O)c1cccs1)C2] | 2100 | 15 | ethyl 3-((3-exo)-(2-(thiophene-2-carboxamido)ethyl)-amino)-8-azabicyclo[3.2.1]octane-8-carboxylate | 352 |
| 41 | 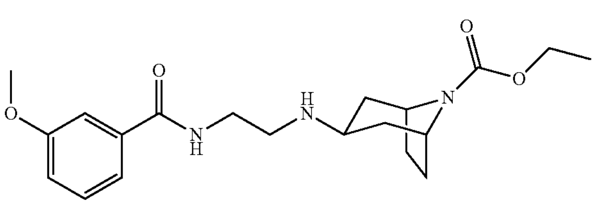 [SMILES: CCOC(=O)N1C2CCC1CC(NCCNC(=O)c1cccc(OC)c1)C2] | n.d. | 19 | ethyl 3-((3-exo)-(2-(3-methoxybenzamido)ethyl)-amino)-8-azabicyclo[3.2.1]octane-8-carboxylate | 376 |

TABLE 2-continued

HUMAN M₁ POTENCY RESULTS

| Ex. | Structure | Potency (EC$_{50}$, nM) | Efficacy (% Max ACh) | Name | M + H |
|-----|-----------|-------------------------|----------------------|------|-------|
| 42 | 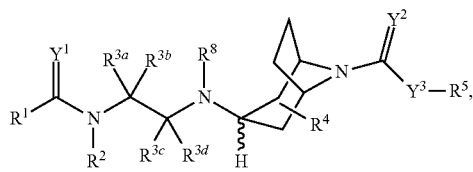 | 4200 | 25 | ethyl 3-((3-exo)-(2-(3-chlorobenzamido)ethyl)-amino)-8-azabicyclo[3.2.1]octane-8-carboxylate | 380 |

Potency was not determined for compounds marked "n.d." Compounds listed in Table 1 and Table 2 are selective agonists for M$_1$ (>20 μM agonist potency (EC$_{50}$) versus M$_2$, M$_3$, M$_4$ and M$_5$) by virtue of receptor activation at an allosteric or bitopic site.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

![formula]

wherein Y$^1$ and Y$^2$ are independently O or S;

wherein Y$^3$ is a covalent bond, O or S;

wherein R$^1$ is an optionally substituted group comprising from 1 to 12 carbons and selected from alkyl, alkenyl, alkenyl, heteroalkyl, heteroalkenyl, heteroalkynyl, cycloalkyl, cycloalkenyl heterocycloalkyl, heterocycloalkenyl, aryl, heteroaryl, alkoxyl, thioalkyl, alkylsulfinyl, alkylsulfonyl, alkylamino, thioamido, amidosulfonyl, alkoxycarbonyl, carboxamide, aminocarbonyl, and alkylamine-carbonyl;

wherein R$^2$ is hydrogen, a protecting group, or an optionally substituted group selected from methyl, ethyl, propyl, butyl, pentyl, or hexyl;

wherein R$^{3a}$, R$^{3b}$, R$^{3c}$, and R$^{3d}$ comprise four substituents independently selected from hydrogen and an optionally substituted C1-C6 alkyl;

wherein R$^4$ comprises ten substituents independently selected from hydrogen, halogen, hydroxyl, nitrile, nitro, thiol, optionally substituted amino, and an optionally substituted group selected from methyl, ethyl, propyl, butyl, pentyl, and hexyl;

wherein R$^5$ is an optionally substituted group comprising from 1 to 6 carbons and selected from methyl, ethyl, propyl, butyl, pentyl, hexyl, aryl, heteroaryl, cycloalkyl, heterocycloalkyl, cycloalkenyl, and heterocycloalkenyl; and wherein R$^8$ is hydrogen, a hydrolysable residue, or an optionally substituted organic residue comprising 1 to 6 carbons, or a pharmaceutically acceptable derivative thereof.

2. The compound of claim 1, wherein R$^1$ has a structure represented by a formula:

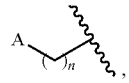

wherein n is 0 or 1; and wherein A is an optionally substituted group selected from aryl, heteroaryl, cycloalkyl, heterocycloalkyl, cycloalkenyl, and heterocycloalkenyl.

3. The compound of claim 1, wherein one of R$^{3a}$, R$^{3b}$, R$^{3c}$, and R$^{3d}$ is optionally substituted C1-C6 alkyl and the remaining of R$^{3a}$, R$^{3b}$, R$^{3c}$, and R$^{3d}$ are hydrogen.

4. The compound of claim 1, wherein R$^{3a}$, R$^{3b}$, R$^{3c}$, and R$^{3d}$ are hydrogen.

5. The compound of claim 1, wherein R$^4$ comprises ten substituents independently selected from hydrogen, halogen, hydroxyl, nitrile, nitro, thiol, optionally substituted amino, and an optionally substituted group selected from methyl, ethyl, propyl, and butyl.

6. The compound of claim 1, wherein R$^4$ comprises ten hydrogens.

7. The compound of claim 1, wherein R$^5$ is an optionally substituted group selected from methyl, ethyl, propyl, butyl, pentyl, and hexyl.

8. The compound of claim 1, wherein R$^5$ is an optionally substituted group selected from aryl, heteroaryl, cycloalkyl, heterocycloalkyl, cycloalkenyl, and heterocycloalkenyl.

9. The compound of claim 1, having a structure represented by a formula:

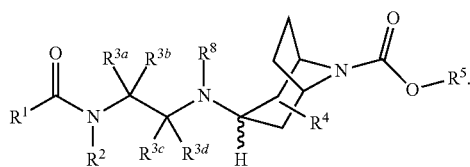

10. The compound of claim 1, having a structure represented by a formula:

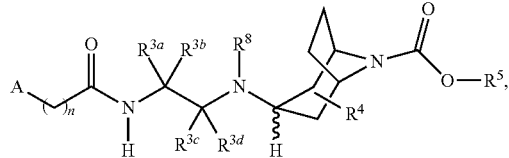

wherein n is 0 or 1; and
wherein A is an optionally substituted group selected from aryl, heteroaryl, cycloalkyl, heterocycloalkyl, cycloalkenyl, and heterocycloalkenyl.

11. The compound of claim 10, having a structure represented by a formula:

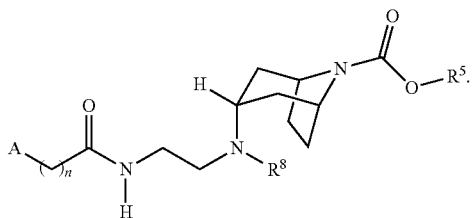

12. The compound of claim 10, having a structure represented by a formula:

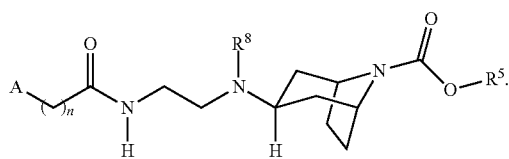

13. The compound of claim 1, wherein the compound activates $M_1$ receptor response in $M_1$-transfected CHO-K1 cells.

* * * * *